US009169468B2

(12) United States Patent
Zhang et al.

(10) Patent No.: US 9,169,468 B2
(45) **Date of Patent: *Oct. 27, 2015**

(54) PENTOSE FERMENTATION BY A RECOMBINANT MICROORGANISM

(71) Applicant: Codexis, Inc., Redwood City, CA (US)

(72) Inventors: Xiyun Zhang, Fremont, CA (US); Ryan C. Fong, Redwood City, CA (US); Ezhilkani Subbian, Mountain View, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/154,488

(22) Filed: Jan. 14, 2014

(65) Prior Publication Data

US 2014/0127780 A1 May 8, 2014

Related U.S. Application Data

(62) Division of application No. 13/429,710, filed on Mar. 26, 2012, now Pat. No. 8,663,962.

(60) Provisional application No. 61/469,505, filed on Mar. 30, 2011, provisional application No. 61/496,152, filed on Jun. 13, 2011.

(51) Int. Cl.
*C12N 9/04* (2006.01)
*C12N 9/02* (2006.01)
*C07H 21/04* (2006.01)
*C07K 1/00* (2006.01)

(52) U.S. Cl.
CPC ....... *C12N 9/0006* (2013.01); *C12Y 101/01307* (2013.01)

(58) Field of Classification Search
CPC ...................... C12Y 101/01307; C12N 9/0006
USPC ................... 435/190, 189; 536/23.2; 530/350
See application file for complete search history.

(56) References Cited

U.S. PATENT DOCUMENTS 4,486,553 A 12/1984 Wesch
5,605,793 A 2/1997 Stemmer
5,811,238 A 9/1998 Stemmer et al.
5,830,721 A 11/1998 Stemmer et al.
5,834,252 A 11/1998 Stemmer et al.
5,837,458 A 11/1998 Minshull et al.
5,928,905 A 7/1999 Stemmer et al.
6,096,548 A 8/2000 Stemmer
6,117,679 A 9/2000 Stemmer
6,132,970 A 10/2000 Stemmer
6,165,793 A 12/2000 Stemmer
6,180,406 B1 1/2001 Stemmer
6,251,674 B1 6/2001 Tobin et al.
6,277,638 B1 8/2001 Stemmer
6,287,861 B1 9/2001 Stemmer et al.
6,287,862 B1 9/2001 delCardayre et al.
6,291,242 B1 9/2001 Stemmer
6,297,053 B1 10/2001 Stemmer
6,303,344 B1 10/2001 Patten et al.
6,309,883 B1 10/2001 Minshull et al.
6,319,713 B1 11/2001 Patten et al.
6,319,714 B1 11/2001 Crameri et al.
6,323,030 B1 11/2001 Stemmer
6,326,204 B1 12/2001 delCardayre et al.
6,335,160 B1 1/2002 Patten et al.
6,335,198 B1 1/2002 delCardayre et al.
6,344,356 B1 2/2002 Stemmer
6,352,859 B1 3/2002 delCardayre et al.
6,355,484 B1 3/2002 Patten et al.
6,358,740 B1 3/2002 Patten et al.
6,358,742 B1 3/2002 Stemmer
6,365,377 B1 4/2002 Patten et al.
6,365,408 B1 4/2002 Stemmer
6,368,861 B1 4/2002 Crameri et al.
6,372,497 B1 4/2002 Stemmer
6,376,246 B1 4/2002 Crameri et al.
6,379,964 B1 4/2002 del Cardayre et al.
6,387,702 B1 5/2002 Stemmer
6,391,552 B2 5/2002 Stemmer
6,391,640 B1 5/2002 Minshull et al.
6,395,547 B1 5/2002 Stemmer
6,406,855 B1 6/2002 Patten et al.
6,406,910 B1 6/2002 Patten et al.
6,413,745 B1 7/2002 Patten et al.
6,413,774 B1 7/2002 Stemmer
6,420,175 B1 7/2002 Stemmer
6,426,224 B1 7/2002 Crameri et al.
6,436,675 B1 8/2002 Welch et al.
6,444,468 B1 9/2002 Stemmer et al.
6,455,253 B1 9/2002 Patten et al.
6,479,652 B1 11/2002 Crameri et al.
6,482,647 B1 11/2002 Stemmer
6,489,146 B2 12/2002 Stemmer et al.
6,506,602 B1 1/2003 Stemmer
6,506,603 B1 1/2003 Stemmer
6,519,065 B1 2/2003 Colbourne et al.

(Continued)

FOREIGN PATENT DOCUMENTS

EP 0 137 280 B1 3/1992
WO 93/03159 A1 2/1993

(Continued)

OTHER PUBLICATIONS

Altschul, S.F., et al., "Gapped BLAST and PSI-BLAST: a new generation of protein database search programs," Nucleic Acids Res., 25(17):3389-3402 [1997].

(Continued)

*Primary Examiner* — Ganapathirama Raghu
(74) *Attorney, Agent, or Firm* — Codexis, Inc.

(57) ABSTRACT

The present invention provides methods and compositions suitable for use in the conversion of xylose to xylitol and xylulose, including nucleic acid constructs, recombinant fungal host cells, and related materials.

3 Claims, 5 Drawing Sheets

(56) References Cited

U.S. PATENT DOCUMENTS 6,521,453 B1 2/2003 Crameri et al.
6,528,311 B1 3/2003 delCardayre et al.
6,573,098 B1 6/2003 Stemmer
6,576,467 B1 6/2003 Stemmer
6,579,678 B1 6/2003 Patten et al.
6,586,182 B1 7/2003 Patten et al.
6,602,986 B1 8/2003 Stemmer et al.
6,613,514 B2 9/2003 Patten et al.
6,653,072 B1 11/2003 Patten et al.
6,716,631 B1 4/2004 delCardayre et al.
6,946,296 B2 9/2005 Patten et al.
6,961,664 B2 11/2005 Selfinov et al.
6,995,017 B1 2/2006 Stemmer
7,024,312 B1 4/2006 Selfinov et al.
7,058,515 B1 6/2006 Selfinov et al.
7,105,297 B2 9/2006 Minshull et al.
7,148,054 B2 12/2006 delCardayre et al.
7,288,375 B2 10/2007 Stemmer et al.
7,430,477 B2 9/2008 Selfinov et al.
7,534,564 B2 5/2009 Patten et al.
7,620,500 B2 11/2009 Mundorff et al.
7,620,502 B2 11/2009 Selfinov et al.
7,629,170 B2 12/2009 delCardayre et al.
7,702,464 B1 4/2010 Emig et al.
7,747,391 B2 6/2010 Gustafsson et al.
7,747,393 B2 6/2010 Fox
7,751,986 B2 7/2010 Gustafsson et al.
7,776,598 B2 8/2010 Patten et al.
7,783,428 B2 8/2010 Gustafsson et al.
7,795,030 B2 9/2010 Minshull et al.
7,853,410 B2 12/2010 Selfinov et al.
7,868,138 B2 1/2011 Stemmer et al.
7,873,499 B2 1/2011 Selfinov et al.
7,904,249 B2 3/2011 Selfinov et al.
7,957,912 B2 6/2011 Selfinov et al.
7,960,152 B2 6/2011 Taylor et al.
8,663,962 B2 * 3/2014 Zhang et al. .................. 435/190
2008/0220990 A1 9/2008 Fox
2009/0312196 A1 12/2009 Colbeck et al.

FOREIGN PATENT DOCUMENTS

WO 95/22625 A1 8/1995
WO 96/00787 A1 1/1996
WO 97/00078 A1 1/1997
WO 97/35966 A1 10/1997
WO 98/27230 A1 6/1998
WO 98/31837 A1 7/1998
WO 00/04190 A1 1/2000
WO 01/75787 A2 10/2001
WO 2007/136762 A2 11/2007
WO 2009/152336 A1 12/2009
WO 2010/144103 A1 12/2010
WO 2011/006138 A2 1/2011

OTHER PUBLICATIONS

Blaiseau, P-L., et al., "Primary structure of a chitinase-encoding gene (chi1) from the filamentous fungus Aphanociadium album: similarity: to bacterial chitinases," Gene, 120:243-248 [1992].

Boel, E., et al., "Two different types of intervening sequences in the glucoamylase gene from Aspergillus niger," EMBO J., 3:1581-85 [1984].

Botstein, D., et al., "Strategies and Applications ofin Vitro Mutagenesis," Science, 229(4719):1193-1201 [1985].

Brat, D., et al., "Functonal Expression of a Bacterial Xylose Isomerase in Saccharomyces cerevisiae," Appl. Environ. Microbiol. 75(8):2304-2311 [Feb. 13, 2009].

Carter, P., "Site-directed mutagenesis," Biochem. J., 237:1-7 [1986].

Case, M.E. et al., "Efficient transformation of Neurospora crassa by utilizing hybrid plasmid DNA," Proc. Natl. Acad. Sci. USA, 76(10):5259-5263 [1979].

Christians, F.C., et al., "Directed evolution of thymidine kinase for AZT phosphoiylation using DNA family shuffling," Nat. Biotechnol., 17:259-264 [1999].

Crameri, A., et al., "DNA shuffling of a family of genes from diverse species accelerates directed evolution," Nature, 391:288-291 [1998].

Crameri, A., et al., "improved green fluorescent protein by molecular evolution using DNA shuffling," Nat. Biotechnol., 14:315-319 [1996].

Crameri, A., et al., "Molecular evolution of an arsenate detoxification pathway by DNA shuffling," Nat. Biotechnol., 15:436-438 [1997].

Dale, S.J., et al., "Oligonucleotide-Directed Random Mutagenesis Using the Phosphorothioate Method," Meth. Mol, Biol., 57:369-74 [1996].

Dayhoff, M.O. et al., in Atlas of Protein Sequence and Structure, "A model of evolutionary change in proteins," vol. 5, Suppl. 3, Natl. Biomed. Res. Round, Washington D.C. [1978], pp. 345-352.

Dupont, A.-L, et al., "Comprehensive characterisation of cellulose- and lignocellulosedegradation products in aged papers: Capillary zone electrophoresis of low-molar mass organic adds, carbohydrates, and aromatic lignin derivatives," Carbohydr. Polym., 68:1-16 [2007].

Henaut and Danchin in Neidhardt et al. [eds,]. *Escherichia coli*and *Salmonella*, " Analysis and predictions from *Escherichia coli* Sequences, or *E. coli* in silico," ASM Press, Washington D,C., [1987], pp. 2047-2066.

Henikoff, S., et al., "Amino add substitution matrices from protein blocks," Proc. Natl. Acad. Sci, USA, 89:-10915-10919 [1992].

Henriksen, A.L.S., et al.,"Study of the glucoamylase promoter in Aspergillius niger using green fluorescent protein," Microbiol., 145:729-34 [1999].

Hjersted, J.L., et al., "Genome-Scale Analysis of Saccharomyces cerevisiae Metabolism and Ethanol Productionin Fed-Batch Culture," Biotechnol. Bioengineer., 97(5):1190-1204 [2007].

Johnstone, I.L., et al., "Cloning an Aspergillus nidulans developmental gene by transformation," EMBO J.,4(5):1307-1311 [1985].

Kelly, J.M., et al., "Transformation of Asoergillus niger by the amdS gene of Aspergillus nidulans," EMBO J., 4(2):475-479 [1985].

Kinsey, J.A., et al., "Transformation of *Neurospora crassa* with the Cloned am (Glutamate Dehydrogenase) Gene," Mol. Cell. Biol., 4:117-122 [1984].

Kramer, B., et aL, "Different base/base mismatches are corrected with different efficiencies by the methyl-directed DNA mismatch-repair system of *E. coli*," Cell, 38:879-887 [1984].

Kuyper, M., et al., "Metabolic engineerng of a xylose-isomerase-expressingSaccharomyces cerevisiae strain for rapid anaerobic xylose fermentation," FEMS Yeast Res., A445:399-409 [2005].

Limon, C., et al., "Primary structure and expression pattern of the 33-kDa chitinase gene from the nucoparasitic fungus Trichocherma harzianum," Curr. Genet., 28:478-83 [1995].

Ling, M.M., et al., "Approaches to Dna Mutagenesis: An Overview," Anal. Biochem., 254(2):157-78 [1997].

Manivasakam, P., et al., "Nonhomologous End Joining during Restriction Enzyme-Mediated DNA Integration in Saccharomyces cerevisiae," Mol. Cell Biol., 18(3):1738-1745 [1998].A46.

Matsushika, A., et al., "Expression of protein engineered NADP+-dependent xylitol dehydrogenase increases ethanol production from xylose in recombinant Saccharomyces cerevisiae," Appl. Environ Microbiol., 81(2):243-55 [2008].

Matsushika, A., et al., "Ethanol production from xylose in engineered Saccharomyces cerevisiae strains: current state and perspectives," Appl. Microbiol. Biotechnol., 84:37-53 [2009].

Minshull, J., et al., "Protein evolution by molecular breeding," Curr. Op. Chem. Biol., 3:284-290 [1999].

Nakamura, Y., et al., "Codon usage tabulated from international DNA sequence databaes: status for the year 2000," Nucl. Acids Res., 28:292 [2000 ].

Numberg, J.H., et al., "Molecular Cloning and Characterization of the Glucoamylase Gene of Aspergillus awamori," Mol. Cell Biol., 4(11):2306-2315 [1984].

Oldenburg, K.R., et al., "Recombination-mediated PCR-directed plasmid construction in vivo in yeast," Nucl. Acids Res., 25(2):451-452 [1997].

McInerney, J.O., "GCUA: general codon usage analysis," Bioinformatics, 14(4):372-73 (1998).

(56) References Cited

OTHER PUBLICATIONS

Park J.B., et al., "The human glutaredoxin gene: determination of its organization, transcription start point, and promoter analysis," Gene, 197:189-93 [1997].
Romanos M.A., et al., "Foreign Gene Expression in Yeast: a Review," Yeast 8:423-488 [1992].
Runquist, D. et al.,"Comparison of heteroloaous xylose transporters in recombinant Saccharomyces cerevisiae," Biotechnol. Biofuels, 3(5):1-7 [2010].
Sauer, U., "Evolutionary Engineering of Industrially Important Microbial Phenotypes," Adv. Biochem. Engineer. Biotechnol., 73:129-169 [2001].
Sedlak, M., et al., "Characterization of the effectiveness of hexose transporters for transporting xylose during glucoseand xylose co-fermentation by a recombinant Saccharomyces yeast,"Yeast 21:671-684 [2004].
Sheir-Neiss, G., et al., "Characterization of the secreted cellulases of Trichoderma reesei wild type and mutants during controlled fermentations," Appl. Micriobiol. Biotechnol., 20:46-53 [1984].
Smith, M., "In Vitro Mutagenesis," Ann. Rev. Genet., 19:423-462 [1985].
Sonderegger, M., et al., "Molecular Basis for Anaerobic Growth of Saccharomyces cerevisiae on Xylose, Investigated by Global Gene Expression and Metabolic Flux Analysis," Appl. Environ. Microbiol., 70(4):2307-2317 [2004].
Stemmer, W.P.C., "DNA shuffling by random fragmentation and reassembly: In vitro recombination for molecular evolution," Proc. Nat. Acad. Sci. USA, 91:10747-10751 [1994].
Stemmer, W.P.C., "Rapid evolution of a protein in vitro by DNA shuffling," Nature, 370:389-391 [1994].
Stenico, M., et al., "Codon usage in Caenorhabditis elegans: delineation of translational selection and mutational biases," Nucl. Acids Res. 22(13):2437-46 [1994].
Teixiera, M.C., et al., "Genome-Wide Identification of Saccharomyces cerevisiae Genes Required for Maximal Tolerance to Ethanol," Appl. Environ. Microbiol., 75(18):5761-5772 [2009].
Tilburn, J., et al., "Transformation by integration in Aspergillus nidulans," Gene 26:205-221 [1983].
Tiwari, S., et al., "Prediction of probable genes by Fourieranalysis of genomic sequences," Comput. Appl. Biosci. 13(3):263-270 [1997].
Uberbacher, E.C., et al., "Discovering and Understanding Genes in Human DNA Sequence Using GRAIL," Methods Enzymol., 266:259-281 [1996].
Wada, K., et al., "Codon usage tabulated from the GenBank genetic sequence data," Nucl. Acids Res., 20:2111-2118 [1992].
Wells, J.A., et al., "Cassette mutagenesis: an efficient method for generation of multiple mutations at defined sites," Gene, 34:315-323 [1985].
Wenger, J.W., et al., "Bulk Segregant Analysis by High-Throughput Sequencing Reveals a Novel Xylose Utilization Gene from *Saccharomyces cerevisiae*," PLoS Genet., 6(5):1-17 [2010].
Wisselink, H.W., et al., "Novel Evolutionary Engineering Approach for Accelerated Utilization of Glucose, Xylose, and Arabinose Mixtures by Engineered Saccharomyces cerevisiae Strains," Appl. Environ. Microbiol., 75(4):907-914 [2009].
Wright, A., et al., "Diverse Plasmid DNA Vectors by Directed Molecular Evolution of Cytomegalovirus Promoters," Hum. Gene Ther., 16:881-892 [2005].
Wright, F., "The 'effective number of codons' used in a gene," Gene 87:23-29 [1990].
Yelton, M.M., et al., "Transformation of Aspergillus nidulans by using a trpC plasmid," Proc. Natl. Acad. Sci. USA, 81:1480-1474 [1984].
Zhang, J.-H., et al., "Directed evolution of a fucosidase from a galactosidase by DNA shuffling and screening" Proc. Nat. Acad. Sci. U.S.A., 94:4504-4509 [1997].
Zhu, T., et al., "Construction of two Gateway vectors for gene expression in fungi," Plasmid 62:128-33 [2009].
Broun, P., et al., "Catalytic Plasticity of Fatty Acid Modification Enzymes Underlying Chemical Diversity of Plant Lipids," Science, 282:1315-1317 [1998].
Devos, D., et al., "Practical limits of function prediction," Proteins: Structure, Function, and Genetics, 41:98-107 [2007].
Seffernick, J.L., et al., "Melamine Deaminase and Atrazine Chlorohydrolase: 98 Percent Identical but Functionally Different," J. Bacteriology, 183(8):2405-2410 [2001].
Whisstock, J., et al., "Prediction of protein function from protein sequence and structure," Quarterly Reviews of Biophysics, 36(3):307-340 [2003].
Witkowski, A., et al., "Conversion of a beta-ketoacyl synthase to a malonyl decarboxylase by replacement of the active-site cysteine with glutamine," Biochemistry, 38:11643-11650 [1999].
Liang, L., et al., "Altering coenzyme specificity of Pichia stipitis xylose reductase by the semi-rational approach CASTing," Microb Cell Fact, 6:36 [2007].
Watanabe, S., et al., "Ethanol production from xylose by recombinant Saccharomyces cerevisiae expressing protein-engineered NADH-preferring xylose reductase from Pichia stipitis," Microbiology, 153:3044-3054 [2007].

* cited by examiner

PENTOSE FERMENTATION BY A RECOMBINANT MICROORGANISM

The present application is a Divisional of U.S. patent application Ser. No. 13/429,710, filed on Mar. 26, 2012, now U.S. Pat. No. 8,663,962, and also claims priority to U.S. Pat. Appln. Ser. No. 61/469,505, filed on Mar. 30, 2011, and U.S. Pat. Appln. Ser. No. 61/496,152, filed on Jun. 13, 2011, each of which is incorporated by reference in their entirety herein.

FIELD OF THE INVENTION

The present invention provides methods and compositions suitable for use in the conversion of xylose to xylitol and xylulose, including nucleic acid constructs, recombinant fungal host cells, and related materials.

BACKGROUND

Ethanol and ethanol fuel blends are widely used in Brazil and in the United States as a transportation fuel. Combustion of these fuels is believed to produce fewer of the harmful exhaust emissions (e.g., hydrocarbons, nitrogen oxide, and volatile organic compounds [VOCs]) that are generated by the combustion of petroleum. Bioethanol is a particularly favored form of ethanol because the plant biomass from which it is produced utilizes sunlight, an energy source that is renewable. In the United States, ethanol is used in gasoline blends that are from 5% to 85% ethanol. Blends of up to 10% ethanol (E10) are approved for use in all gasoline vehicles in the U.S. and blends of up to 85% ethanol (E85) can be utilized in specially engineered flexible-fuel vehicles (FFV). The Brazilian government has mandated the use of ethanol-gasoline blends as a vehicle fuel, and the mandatory blend has been 25% ethanol (E25) since 2007.

Bioethanol is currently produced by the fermentation of hexose sugars that are obtained from carbon feedstocks. Currently, only the sugar from sugar cane and starch from feedstock such as corn can be economically converted. There is, however, much interest in using lignocellulosic feedstocks where the cellulose part of a plant is broken down to sugars and subsequently converted to ethanol. Lignocellulosic biomass is made up of cellulose, hemicelluloses, and lignin. Cellulose and hemicellulose can be hydrolyzed in a saccharification process to sugars that can be subsequently converted to ethanol via fermentation. The major fermentable sugars from lignocelluloses are glucose and xylose. For economical ethanol yields, a strain that can effectively convert all the major sugars present in cellulosic feedstock would be highly desirable.

SUMMARY OF THE INVENTION

The present invention provides methods and compositions suitable for use in the conversion of xylose to xylitol and xylulose, including nucleic acid constructs, recombinant fungal host cells, and related materials.

In some embodiments, the present invention provides recombinant nucleic acid constructs comprising at least one polynucleotide sequence that encodes at least one xylose reductase, wherein the polynucleotide is selected from: (a) a polynucleotide that encodes a polypeptide comprising an amino acid sequence having at least about 70% identity to SEQ ID NO:2, wherein the amino acid sequence comprises at least one substitution set forth herein; and (b) a polynucleotide that hybridizes under stringent hybridization conditions to the complement of a polynucleotide that encodes a polypeptide having the amino acid sequence of SEQ ID NO:2, and wherein the amino acid sequence comprises at least one substitution set forth herein. In some embodiments, the polynucleotide sequence encodes a polypeptide comprising an amino acid sequence at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:2, wherein the amino acid sequence comprises at least one substitution set forth herein. In some alternative embodiments, the polynucleotide sequence encodes a polypeptide comprising a portion of the amino acid sequence set forth in SEQ ID NO:2, wherein the amino acid sequence comprises at least one substitution set forth herein. In some further embodiments, the polynucleotide sequence encodes a polypeptide having an amino acid sequence that comprises at least one substitution at position 2, 3, 7, 11, 14, 17, 23, 24, 33, 36, 46, 47, 49, 56, 62, 68, 89, 97, 102, 108, 114, 116, 123, 132, 134, 143, 152, 155, 157, 162, 168, 184, 206, 219, 224, 225, 226, 228, 246, 231, 232, 233, 236, 240, 242, 245, 246, 249, 252, 255, 261, 266, 267, 275, 276, 279, 281, 282, 283, 285, 297, 301, 302, 303, and/or 318, wherein the positions are numbered by correspondence with the amino acid sequence of *P. stipitis* xylose reductase set forth in SEQ ID NO:2. In some additional embodiments, the polynucleotide sequence encodes a polypeptide having an amino acid sequence that comprises at least one substitution selected from P2, S3, N7, D11, A14, F17, D23, V24, R33, K36, E46, D47, A49, A56, I62, K68, E89, S97, D102, L108, T114, K116, K123, K132, D134, I143, K152, K155, G157, I162, P168, S184, R206, Q219, L224, N225, Q226, R228, A246, N231, T232, S233, F236, T240, K242, A245, A246, G249, P252, V255, S261, A266, I267, P275, R276, E279, K281, D282, V283, S285, A297, I301, N302, L303, and/or V318, wherein the positions are numbered by correspondence with the amino acid sequence of *P. stipitis* xylose reductase set forth in SEQ ID NO:2. In yet some additional embodiments, the polynucleotide sequence encodes a polypeptide having an amino acid sequence that comprises at least one substitution selected from P2T, S3H, S3R, S3W, N7L, D11K, A14V, F17W, D23E, V24G, R33L, R22V, K36Q, E46K, D47G, D47N, A49G, A56E, A56Y, 162V, K68G, K68M, K68R, E89N, E89V, S97R, S97T, D102T, L108Y, T114S, K116Q, K123C, K132A, K132N, D134E, D134H, D134V, I143L, K152A, K152E, K152H, K152Q, K155A, K155D, K155I, K155R, K155Y, G157R, I162L, P168S, S184A, R206S, R206V, Q219H, Q219L, Q219T, L224A, L224S, L224V, N225D, N225E, N225K, N225S, N225Y, Q226D, Q226E, Q226S, Q226V, R228T, N231G, N231H, N231L, N231S, T232A, T232C, T232S, T232V, S233C, S233F, S233G, S233I, S233K, S233V, F236L, T240V, K242L, A245S, A246L, A246S, G249D, P252C, V255I, S261A, S261C, S261N, S261T, A266V, A266C, 1267V, P275A, R276M, R276W, E279Q, K281L, K281V, D282C, D282G, D282R, V283H, S285E, S285T, A297H, A297S, I301C, I301Y, N302D, N302G, N302S, L303I, L303V, and/or V318C, wherein the positions are numbered by correspondence with the amino acid sequence of *P. stipitis* xylose reductase set forth in SEQ ID NO:2. In some embodiments, the polynucleotide sequence is at least about 80%, about 85%, about 90%, or at least 95% identical to SEQ ID NO:1, and wherein the polynucleotide sequence comprises at least one mutation set forth herein. In some additional embodiments, the polynucleotide sequence comprises at least one mutation selected from t82a, t99a, g156a, c201t, a280c, c306t, t354g, t358c, a378t, c408t, a426t, c438t, a478c, t511c, a585g, t670c, t688c, t703c, t747c, t751a, t766c, t811a, c816t, a826c, c849g, c855t, and/or c906t, wherein the nucleotide position is determined by alignment with SEQ ID NO:1. In some additional embodiments, the present invention provides nucleic acid constructs comprising SEQ ID NO:3 and/or SEQ ID NO:4.

The present invention also provides isolated xylose reductase variants, wherein the variants have xylose reductase activity and comprise a substitution at one or more positions selected from 2, 3, 7, 11, 14, 17, 23, 24, 33, 36, 46, 47, 49, 56, 62, 68, 89, 97, 102, 108, 114, 116, 123, 132, 134, 143, 152, 155, 157, 162, 168, 184, 206, 219, 224, 225, 226, 228, 246, 231, 232, 233, 236, 240, 242, 245, 246, 249, 252, 255, 261, 266, 267, 275, 276, 279, 281, 282, 283, 285, 297, 301, 302, 303, and/or 318, wherein the positions are numbered by correspondence with the amino acid sequence of *P. stipitis* xylose reductase set forth in SEQ ID NO:2. In some embodiments, the variant has xylose reductase activity and comprises a substitution at one or more positions selected from P2, S3, N7, D11, A14, F17, D23, V24, R33, K36, E46, D47, A49, A56, I62, K68, E89, S97, D102, L108, T114, K116, K123, K132, D134, I143, K152, K155, G157, I162, P168, S184, R206, Q219, L224, N225, Q226, R228, A246, N231, T232, S233, F236, T240, K242, A245, A246, G249, P252, V255, S261, A266, I267, P275, R276, E279, K281, D282, V283, S285, A297, I301, N302, L303, and/or V318, wherein the positions are numbered by correspondence with the amino acid sequence of *P. stipitis* xylose reductase set forth in SEQ ID NO:2. In some additional embodiments, the variant has xylose reductase activity and comprises a substitution at one or more positions selected from P2T, S3H, S3R, S3W, N7L, D11K, A14V, F17W, D23E, V24G, R33L, R22V, K36Q, E46K, D47G, D47N, A49G, A56E, A56Y, 162V, K68G, K68M, K68R, E89N, E89V, S97R, S97T, D102T, L108Y, T114S, K116Q, K123C, K132A, K132N, D134E, D134H, D134V, I143L, K152A, K152E, K152H, K152Q, K155A, K155D, K155I, K155R, K155Y, G157R, I162L, P168S, S184A, R206S, R206V, Q219H, Q219L, Q219T, L224A, L224S, L224V, N225D, N225E, N225K, N225S, N225Y, Q226D, Q226E, Q226S, Q226V, R228T, N231G, N231H, N231L, N231S, T232A, T232C, T232S, T232V, S233C, S233F, S233G, S233I, S233K, S233V, F236L, T240V, K242L, A245S, A246L, A246S, G249D, P252C, V255I, S261A, S261C, S261N, S261T, A266V, A266C, 1267V, P275A, R276M, R276W, E279Q, K281L, K281V, D282C, D282G, D282R, V283H, S285E, S285T, A297H, A297S, I301C, I301Y, N302D, N302G, N302S, L303I, L303V, and/or V318C, wherein the positions are numbered by correspondence with the amino acid sequence of *P. stipitis* xylose reductase set forth in SEQ ID NO:2. In some further embodiments, the isolated xylose reductase variants comprise the sequence set forth in SEQ ID NO:41, 43, 45, and/or 47. The present invention also provides isolated nucleic acid sequences comprising SEQ ID NO:3, 4, 40, 42, 44, and/or 46.

The present invention also provides recombinant nucleic acid constructs comprising at least one polynucleotide sequence that encodes a xylitol dehydrogenase, wherein the polynucleotide is selected from: (a) a polynucleotide that encodes a polypeptide comprising an amino acid sequence having at least 70% identity to SEQ ID NO:6, wherein the amino acid sequence comprises at least one substitution set forth herein; and (b) a polynucleotide that hybridizes under stringent hybridization conditions to the complement of a polynucleotide that encodes a polypeptide having the amino acid sequence of SEQ ID NO:6, wherein the amino acid sequence comprises at least one substitution set forth herein. The present invention further provides nucleic acid constructs, wherein the polynucleotide sequence encodes a polypeptide comprising an amino acid sequence at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:6, wherein the amino acid sequence comprises at least one substitution set forth herein. In some embodiments, the polynucleotide sequence encodes a polypeptide comprising at least a portion of the amino acid sequence set forth in SEQ ID NO:6, wherein the amino acid sequence comprises at least one substitution set forth herein. In some further embodiments, the polynucleotide sequence encodes a polypeptide having an amino acid sequence that comprises at least one substitution at position 5, 13, 19, 49, 81, 149, 187, 189, 202, 205, 206, 210, 215, 218, 226, 227, 228, 229, 230, 231, 235, 239, 241, 251, 252, 256, 260, 286, 287, 296, 307, 327, 350, and/or 352, wherein the positions are numbered by correspondence with the amino acid sequence of *P. stipitis* xylitol dehydrogenase set forth in SEQ ID NO:6. In some additional embodiments, the polynucleotide sequence encodes a polypeptide having an amino acid sequence that comprises at least one substitution selected from P5, D13, T19, A49, S81, H149, V187, L189, G202, V205, V206, I208, F209, D210, N211, M215, D218, F226, N227, S228, K229, T230, G231, E235, A239, G241, C251, T252, P256, L260, T286, V287, F296, K307, D327, A350, and/or K352, wherein the positions are numbered by correspondence with the amino acid sequence of *P. stipitis* xylitol dehydrogenase set forth in SEQ ID NO:6. In some further embodiments, the polynucleotide sequence encodes a polypeptide having an amino acid sequence that comprises at least one substitution selected from P5E, P5R, D13G, T19L, T19Q, A49Q, S81G, H149R, V187M, L189C, G202D, V205C, V205H, V206A, I208R, F209S, D210W, N211K, N211R, N211S, M215A, M215C, D218R, F226V, N227T, S228P, K229R, T230V, G231A, G231H, E235K, E235Q, A239C, G241W, C251G, C251T, T252S, P256A, P256Q, L260Q, T286V, V287L, F296R, K307R, D327A, A350D, and/or K352E, wherein the positions are numbered by correspondence with the amino acid sequence of *P. stipitis* xylitol dehydrogenase set forth in SEQ ID NO:6. In some still further embodiments, the polynucleotide sequence is at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:5, and wherein the polynucleotide sequence comprises at least one mutation set forth herein. In some embodiments, the polynucleotide sequence comprises mutations at at least one position selected from t24g, c630t, a732g, a768t, a780g, wherein nucleotide position is determined by alignment with SEQ ID NO:5. In some additional embodiments, the nucleic acid construct comprises SEQ ID NO:7 and/or SEQ ID NO:8. In some further embodiments, the present invention provides an isolated nucleic acid sequence comprising SEQ ID NO:7, 8, and/or 48.

The present invention also provides isolated xylitol dehydrogenase variants comprising the sequence set forth in SEQ ID NO:49. In some additional embodiments, the present invention provides isolated xylitol dehydrogenase variants, wherein the variants have xylitol dehydrogenase activity and comprise a substitution at one or more positions selected from 5, 13, 19, 49, 81, 149, 187, 189, 202, 205, 206, 210, 215, 218, 226, 227, 228, 229, 230, 231, 235, 239, 241, 251, 252, 256, 260, 286, 287, 296, 307, 327, 350, and/or 352, wherein the positions are numbered by correspondence with the amino acid sequence of *P. stipitis* xylitol dehydrogenase set forth in SEQ ID NO:6. In some embodiments, the xylitol dehydrogenase variant have xylitol dehydrogenase activity and comprise a substitution at one or more positions selected from P5, D13, T19, A49, S81, H149, V187, L189, G202, V205, V206, I208, F209, D210, N211, M215, D218, F226, N227, S228, K229, T230, G231, E235, A239, G241, C251, T252, P256, L260, T286, V287, F296, K307, D327, A350, and/or K352, wherein the positions are numbered by correspondence with the amino acid sequence of *P. stipitis* xylitol dehydrogenase set forth in SEQ ID NO:6. In some further embodiments, the isolated xylitol dehydrogenase variant has xylitol dehydrogenase activity and comprises a substitution at one or more positions selected from P5E, P5R, D13G, T19L, T19Q, A49Q, S81G, H149R, V187M, L189C, G202D, V205C, V205H, V206A, I208R, F209S, D210W, N211K, N211R, N211S, M215A, M215C, D218R, F226V, N227T, S228P, K229R, T230V, G231A, G231H, E235K, E235Q, A239C, G241W, C251G, C251T, T252S, P256A, P256Q, L260Q, T286V, V287L, F296R, K307R, D327A, A350D, and/or K352E, wherein the positions are numbered by correspondence with the amino acid sequence of *P. stipitis* xylitol dehydrogenase set forth in SEQ ID NO:6. The present invention also provides recombinant nucleic acid constructs comprising SEQ ID NO:11 and/or SEQ ID NO:12.

The present invention also provides recombinant nucleic acid constructs comprising polynucleotide sequences encoding at least one xylose reductase and at least one xylitol dehydrogenase, wherein the polynucleotide sequences are selected from SEQ ID NOS:1, 3, 4, 40, 42, 44, and 46; and SEQ ID NOS:5, 7, 8, 48.

The present invention further provides recombinant nucleic acid constructs further comprising at least one polynucleotide sequence encoding at least one xylulokinase, wherein the polynucleotide sequence comprises SEQ ID NO:11 and/or SEQ ID NO:12. In some embodiments, the recombinant nucleic acid constructs comprise at least one sequence selected from SEQ ID NOS:1, 3, 4, 5, 7, 8, 11, 12, 40, 42, 44, 46, and 48. In some further embodiments, the constructs comprise SEQ ID NO:46 and/or 48. In some additional embodiments, the nucleic acid constructs further comprise at least one genetic element that facilitates stable integration into a fungal host genome. In some additional embodiments, the nucleic acid constructs further comprise a genetic element that facilitates stable integration into a fungal host genome. In some embodiments, the genetic element facilitates integration into a fungal host genome by homologous recombination. In yet some additional embodiments, the nucleic acid constructs comprise a fungal origin of replication. In some embodiments, the fungal origin of replication is a yeast origin of replication. In some further embodiments, the polynucleotide sequence is operatively linked to a promoter sequence that is functional in a fungal cell. In some embodiments, the promoter sequence is a fungal promoter sequence. In some additional embodiments, the fungal promoter sequence is a yeast promoter sequence. In still some further embodiments, the polynucleotide sequence is operatively linked to a transcription termination sequence that is functional in a fungal cell. In some embodiments, the polynucleotide sequence contains codons optimized for expression in a yeast cell. In some further embodiments, the polynucleotide sequence comprises SEQ ID NO:3, 4, 7, 8, 11, and/or 12.

The present invention also provides recombinant fungal host cells comprising at least one polynucleotide sequence encoding at least one xylose reductase, wherein the polynucleotide sequences comprise at least one mutation relative to SEQ ID NO:1, as set forth herein. In some embodiments, the recombinant fungal host cell comprises at least one polynucleotide sequence selected from SEQ ID NOS:3, 4, 40, 42, 44, and 46. In some embodiments, the recombinant fungal host cells comprise at least one polynucleotide sequence encoding at least one xylitol dehydrogenase, wherein the polynucleotide sequence comprises at least one mutation relative to SEQ ID NO:5, as set forth herein. In some embodiments, at least one polynucleotide sequence is selected from SEQ ID NOS:7, 8, and 48.

The present invention also provides recombinant fungal host cells comprising at least one polynucleotide sequence encoding at least one xylulokinase, wherein the polynucleotide sequences comprise at least one mutation relative to SEQ ID NO:9. In some embodiments, at least one polynucleotide sequence is selected from SEQ ID NOS:11 and 12.

The present invention also provides recombinant fungal host cells comprising at least one polynucleotide sequence encoding at least one xylose reductase, wherein the polynucleotide sequence comprises SEQ ID NO:1, 3, 4, 40, 42, 44, and/or 46; and at least one polynucleotide encoding at least one xylitol dehydrogenase, wherein the polynucleotide sequence comprises SEQ ID NO:5, 7, 8, and/or 48. In some embodiments, the recombinant fungal host cells further comprise at least one polynucleotide encoding at least one xylulokinase, wherein the polynucleotide comprises SEQ ID NO:11 and/or 12. In some embodiments, at least one polynucleotide is integrated into the host cell genome. In some additional embodiments, the host cell is a yeast cell. In some embodiments, the host cell has had one or more native genes deleted from its genome. In some further embodiments, the deletion results in one or more phenotypes selected from increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced production of by products, wherein comparison is made with respect to the corresponding host cell without the deletion(s). In some additional embodiments, the host cell is altered to overexpress one or more polynucleotides. In some further embodiments, overexpression results in one or more phenotypes selected from increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced product of by products, wherein comparison is made to the corresponding unaltered host cell. In still some further embodiments, the host cell comprises at least one xylose reductase variant and at least one xylitol dehydrogenase variant. In some additional embodiments, the recombinant fungal host cells further comprise at least one xylulokinase. In some embodiments, the xylulokinase is encoded by SEQ ID NO:11 and/or 12. In some additional embodiments, the recombinant fungal host cell is transformed using nucleic acid constructs comprising from about two to about fifty copies of at least one xylose reductase and/or xylitol dehydrogenase and/or xylulokinase. It is not intended that the present invention be limited to any particular copy number of xylose reductase and/or xylitol dehydrogenase genes and/or xylulokinase, as any suitable number finds use in the present invention. In some embodiments, the nucleic acid constructs comprise any combination of wild-type and/or variant xylose reductase and/or xylitol dehydrogenase and/or xylulokinase. Furthermore, any suitable method for introducing multiple copies of either xylose reductase and/or xylitol dehydrogenase and/or xylulokinase find use in the present invention.

The present invention also provides processes for producing a fermentation product, comprising: (a) providing at least one recombinant fungal host cell provided herein; (b) providing a fermentation medium comprising; and (c) contacting the fermentation medium with the recombinant fungal host cell under conditions suitable for generating the fermentation product. In some embodiments, the process further comprises (d) recovering the fermentation product. In some additional embodiments, the fermenting step is carried out under conditions selected from microaerobic or aerobic conditions. In some embodiments, the fermenting step is carried out under anaerobic conditions. In some further embodiments, the fermentation product is selected from an alcohol, a fatty acid, lactic acid, acetic acid, 3-hydroxypropionic acid, acrylic acid, succinic acid, citric acid, malic acid, fumaric acid, succinic acid, an amino acid, 1,3-propanediol, ethylene, glycerol, and a β-lactam. In some additional embodiments, the fermentation product is an alcohol selected from ethanol and butanol. In some embodiments, the fermentation product is ethanol. In some embodiments, the fermentation medium comprises product from a saccharification process. In some further embodiments, the fermentation medium comprises hemicellulosic feedstock.

DESCRIPTION OF THE FIGURES

FIG. 2A depicts the pentose phosphate pathway (PPP). The substrates and products are shown. The enzymes are represented by numbers as follows: 6. Ribulose-5-phosphate 3-epimerase; 7. Transketolase (TKL1); 8. Transaldolase (TAL1); 9. Ribose-5-phosphate ketoisomerase (RKI1); 10. 6-phosphogluconate dehydrogenase (GND1); 11. 6-phosphogluconalactonase (SOL3); and 12. Glucose-6-phosphate-1-dehydrogenase (ZWF).

FIG. 2B depicts the pathway of glycolysis. The substrates and products are shown. The enzymes are represented by numbers as follows: 13. Hexokinase; 14. Phosphoglucose isomerase; 15. Phosphofructokinase; 16. Aldolase; 17. Triose phosphate isomerase; 18. Glyceraldehyde 3-phosphate dehydrogenase; 19. 3-Phosphoglycerate kinase; 20. Phosphoglyceromutase; 21. Enolase; and 22. Pyruvate kinase.

FIG. 2C depicts the metabolic pathway for converting pyruvate to ethanol. The substrates and products are shown. The enzymes are represented by numbers as follows: 23. Pyruvate decarboxylase; 24. Aldehyde dehydrogenase; and 25. Alcohol dehydrogenase.

DESCRIPTION OF THE INVENTION

Figure 1:
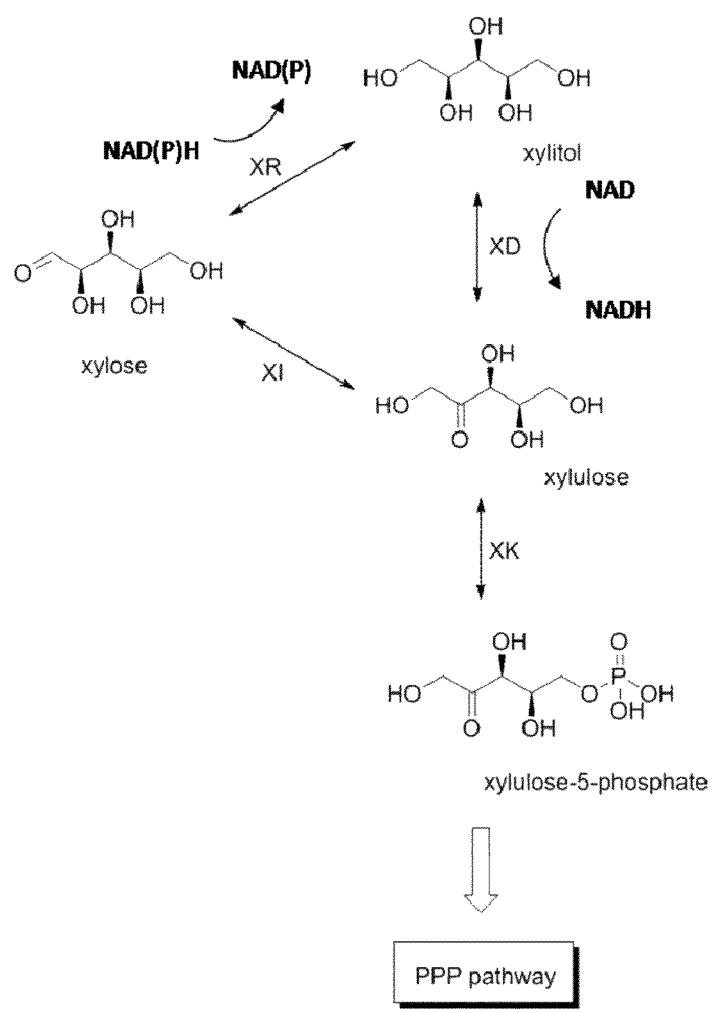
FIG. 1 depicts xylose conversion pathways. In yeast and filamentous fungi, D-xylose is initially reduced to xylitol by NAD(P)H-dependent xylose reductase ("XR"). Xylitol is subsequently oxidized to D-xylulose by NAD+-dependent xylitol dehydrogenase ("XDH" or "XD"). Xylulokinase ("XK") subsequently phosphorylates D-xylulose to produce D-xylulose 5-phosphate, which is then further metabolized through the pentose phosphate pathway ("PPP"). In bacteria, D-xylose is directly converted to D-xylulose by a xylose isomerase ("XI").

The present invention provides methods and compositions suitable for use in the conversion of xylose to xylitol and xylulose, including nucleic acid constructs, recombinant fungal host cells, and related materials.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the terms "isolated" and "purified" are used to refer to a molecule (e.g., an isolated nucleic acid, polypeptide, etc.) or other component that is removed from at least one other component with which it is naturally associated.

As used herein, the term "reference enzyme" refers to an enzyme to which a variant enzyme of the present invention is compared in order to determine the presence of an improved property in the variant enzyme being evaluated, including but not limited to improved thermoactivity, improved thermostability, or improved stability. In some embodiments, a reference enzyme is a wild-type enzyme (e.g., wild-type xylose reductase or xylitol dehydrogenase). In some embodiments, a reference enzyme is another variant enzyme (e.g., another variant xylose reductase or xylitol dehydrogenase enzyme of the present invention).

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. A recombinant cell contains a recombinant polynucleotide or polypeptide.

As used herein, the terms "enzyme variant" and "variant enzyme" are used in reference to enzymes that are similar to a reference enzyme, particularly in their function, but have mutations in their amino acid sequence that make them different in sequence from the wild-type or another reference enzyme. Enzyme variants (e.g., "xylose reductase variants" and/or "xylitol dehydrogenase variants") can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagensis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. After the variants are produced, they can be screened for the desired property (e.g., high or increased; or low or reduced activity, increased thermal and/or alkaline stability, etc.).

As used herein, "combinatorial variant" refers to any variant that has a combination of two or more mutations (e.g., substitutions). In some embodiments, the combination of mutations results in changes in enzyme activity (e.g., improved thermostability, improved thermoactivity, improved specific activity, etc.).

As used herein, the term "overexpress" is intended to encompass increasing the expression of a protein to a level greater than the cell normally produces. It is intended that the term encompass overexpression of endogenous, as well as heterologous proteins.

For clarity, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, the ability to utilize xylose as a carbon source, etc.

A nucleic acid construct, nucleic acid (e.g., a polynucleotide), polypeptide, or host cell is referred to herein as "recombinant" when it is non-naturally occurring, artificial or engineered.

The terms "xylose reductase" and "xylose reductase polypeptide" are used interchangeably herein to refer to an enzyme that is capable of catalyzing xylose to xylitol. The ability to catalyze xylose to xylitol is referred to herein as "xylose reductase activity".

The terms "protein" and "polypeptide" are used interchangeably herein to refer to a polymer of amino acid residues. The term "xylose reductase polynucleotide" refers to a polynucleotide that encodes a xylose reductase polypeptide.

In some embodiments, xylose reductase polynucleotides employed in the practice of the present invention encode a polypeptide comprising an amino acid sequence that is at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:2, wherein the sequence comprises at least one substitution set forth herein. In some embodiments, the xylose reductase polynucleotide encodes a polypeptide having an amino acid sequence comprising SEQ ID NO:41, 43, 45, and/or 47.

In some embodiments, xylose reductase polynucleotides employed in the practice of the present invention comprise polynucleotide sequences that are at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1, 3 and/or 4.

The terms "xylitol dehydrogenase" and "xylitol dehydrogenase polypeptide" are used interchangeably herein to refer to an enzyme that is capable of catalyzing xylitol to xylulose. The ability to catalyze xylitol to xylulose is referred to herein as "xylitol dehydrogenase activity". Also, as used herein, the term "xylitol dehydrogenase polynucleotide" refers to a polynucleotide that encodes a xylitol dehydrogenase polypeptide.

In some embodiments, xylitol dehydrogenase polynucleotides employed in the practice of the present invention encode polypeptides comprising amino acid sequences that are at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:6, wherein SEQ ID NO:6 further comprises at least one substitution as set forth herein. In some embodiments, the xylitol dehydrogenase polynucleotide encodes a polypeptide having an amino acid sequence comprising SEQ ID NO:6 and/or 49, wherein SEQ ID NO:6 further comprises at least one substitution as set forth herein In some embodiments, xylulokinase polynucleotides employed in the practice of the present invention comprise polynucleotides sequence that are at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:9, 11 and/or 12, wherein SEQ ID NO:9 further comprises at least one substitution.

The terms "percent identity," "% identity", "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/accurate pairwise optimal alignments—DNA/Protein Gap Open Penalty: 15/10; DNA/Protein Gap Extension Penalty: 6.66/0.1; Protein weight matrix: Gonnet series; DNA weight matrix: Identity; Toggle Slow/Fast pairwise alignments=SLOW or FULL Alignment; DNA/Protein Number of K-tuple matches: 2/1; DNA/Protein number of best diagonals: 4/5; DNA/Protein Window size: 4/5.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art (See, e.g., Dayhoff et al., in Dayhoff [ed.], *Atlas of Protein Sequence and Structure*," Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g., Altschul et al., supra).

The present invention also provides a recombinant nucleic acid construct comprising a xylose reductase polynucleotide sequence that hybridizes under stringent hybridization conditions to the complement of a polynucleotide which encodes a polypeptide having the amino acid sequence of SEQ ID NO:2, wherein the polypeptide is capable of catalyzing the xylose to xylitol, and the polypeptide comprises at least one substitution set forth herein.

In some embodiments, the polynucleotide that hybridizes to the complement of a polynucleotide which encodes a polypeptide having the amino acid sequence of SEQ ID NO:2, wherein the polypeptide comprises at least one substitution as set forth herein, does so under high or very high stringency conditions to the complement of a reference sequence having the sequence of SEQ ID NO:1 (e.g., over substantially the entire length of the reference sequence). In some embodiments, the polynucleotide that hybridizes to the complement of a polynucleotide which encodes a polypeptide having the amino acid sequence of SEQ ID NO:2, wherein the polypeptide comprises at least one substitution as set forth herein, does so under high or very high stringency conditions to the complement of a reference sequence having the sequence of SEQ ID NO:3 (e.g., over substantially the entire length of the reference sequence). In some embodiments, the polynucleotide that hybridizes to the complement of a polynucleotide which encodes a polypeptide having the amino acid sequence of SEQ ID NO:2, wherein the amino acid sequence comprises at least one substitution as set forth herein, does so under high or very high stringency conditions to the complement of a reference sequence having the sequence of SEQ ID NO:4 (e.g., over substantially the entire length of the reference sequence).

The present invention also provides a recombinant nucleic acid construct comprising a xylitol dehydrogenase polynucleotide sequence that hybridizes under stringent hybridization conditions to the complement of a polynucleotide which encodes a polypeptide having the amino acid sequence of SEQ ID NO:6, wherein the polypeptide comprises at least one substitution set forth herein, and wherein the polypeptide is capable of catalyzing xylitol to xylulose.

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology-Hybridization with Nucleic Acid Probes*," Part 1, Chapter 2, Elsevier, New York, [1993], which is incorporated herein by reference). For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The terms "corresponding to", "reference to" and "relative to" when used in the context of the numbering of a given amino acid or polynucleotide sequence refers to the numbering of the residues of a specified reference sequence when the given amino acid or polynucleotide sequence is compared to the reference sequence.

The "position" is denoted by a number that sequentially identifies each amino acid in the reference sequence based on its position relative to the N-terminus. Owing to deletions, insertions, truncations, fusions, and the like that must be taken into account when determining an optimal alignment, in general the amino acid residue number in a test sequence determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position the reference sequence. In the case of truncations or fusions there can be stretches of amino acids in either the reference or aligned sequence that do not correspond to any amino acid in the corresponding sequence.

As used herein, the terms "transformed" and "transformation" used in reference to a cell refer to a cell that has a non-native nucleic acid sequence integrated into its genome or has an episomal plasmid that is maintained through multiple generations.

As used herein, the term "by-product" refers to an organic molecule that is an undesired product of a particular fermentation process.

As used herein, the term "xylose pathway" refers to the steps of conversion of xylose to xylulose phosphate which is then metabolized through the pentose phosphate pathway. In some embodiments, this involves the reduction of xylose to xylitol, oxidation of xylitol to xylulose and subsequent conversion of xylulose to xylulose phosphate. In some other embodiments the xylose is directly converted to xylulose which is then phosphorylated to xylulose phosphate.

As used herein the term "xylose pathway enzymes" refers to the enzymes that catalyze the conversion of xylose to xylulose-phosphate. In some embodiments, these enzymes comprise xylose reductase, xylitol dehydrogenase and/or xylulose kinase. In some other embodiments, the enzymes comprise xylose isomerase and xylulose kinase.

DETAILED DESCRIPTION OF THE INVENTION

The present invention provides methods and compositions suitable for use in the conversion of xylose to xylitol and xylulose, including nucleic acid constructs, recombinant fungal host cells, and related materials.

The initial metabolic pathways for xylose utilization in fungi and bacteria differ. In most fungi, including xylose-fermenting yeasts (e.g., *Pichia stipitis, Pachysolen tannophilus*, and *Candida shehatae*), D-xylose is converted to D-xylulose by two oxidoreductases involving cofactors NAD(P)H and NAD(P)+. (See, Matsushika et al., Appl. Microbiol. Biotechnol., 84:37-53 [2009]). In these organisms, D-xylose is initially reduced to xylitol by NAD(P)H-dependent xylose reductase ("XR") (EC 1.1.1.21). Xylitol is subsequently oxidized to D-xylulose by NAD+-dependent xylitol dehydrogenase ("XDH" or "XD") (EC 1.1.1.9). Xylulokinase ("XK") (EC 2.7.1.17) subsequently phosphorylates D-xylulose to produce D-xylulose 5-phosphate ("X5P"), which is then further metabolized through the pentose phosphate pathway ("PPP"). FIG. 1 provides a schematic of the pathway.

However, most strains of *S. cerevisiae* cannot utilize xylose even though the genes encoding XR, XDH, and XK are present in its genome, as the expression levels of these enzymes are too low to allow xylose utilization (See, Matsushika et al., supra). Some strains have been shown to natively utilize xylose but at very low rates and fermentation to ethanol has not been detected (See, Wenger et al., PLoS Genet., 6(5):e1000942 [2010]). Even when the endogenous genes are overexpressed in *S. cerevisiae*, only slow growth on xylose has been observed (See, Matsushika et al. supra).

In contrast, most bacteria (e.g., *Escherichia coli* and *Streptomyces* species) can isomerize D-xylose directly to D-xylulose by using a xylose isomerase ("XI") (EC 5.3.1.5) (See, Matsushika et al., supra). In bacteria, as in fungi, the D-xylulose is phosphorylated to D-xylulose 5-phosphate by XK, which is then further metabolized through the pentose phosphate pathway.

Figure 2A:
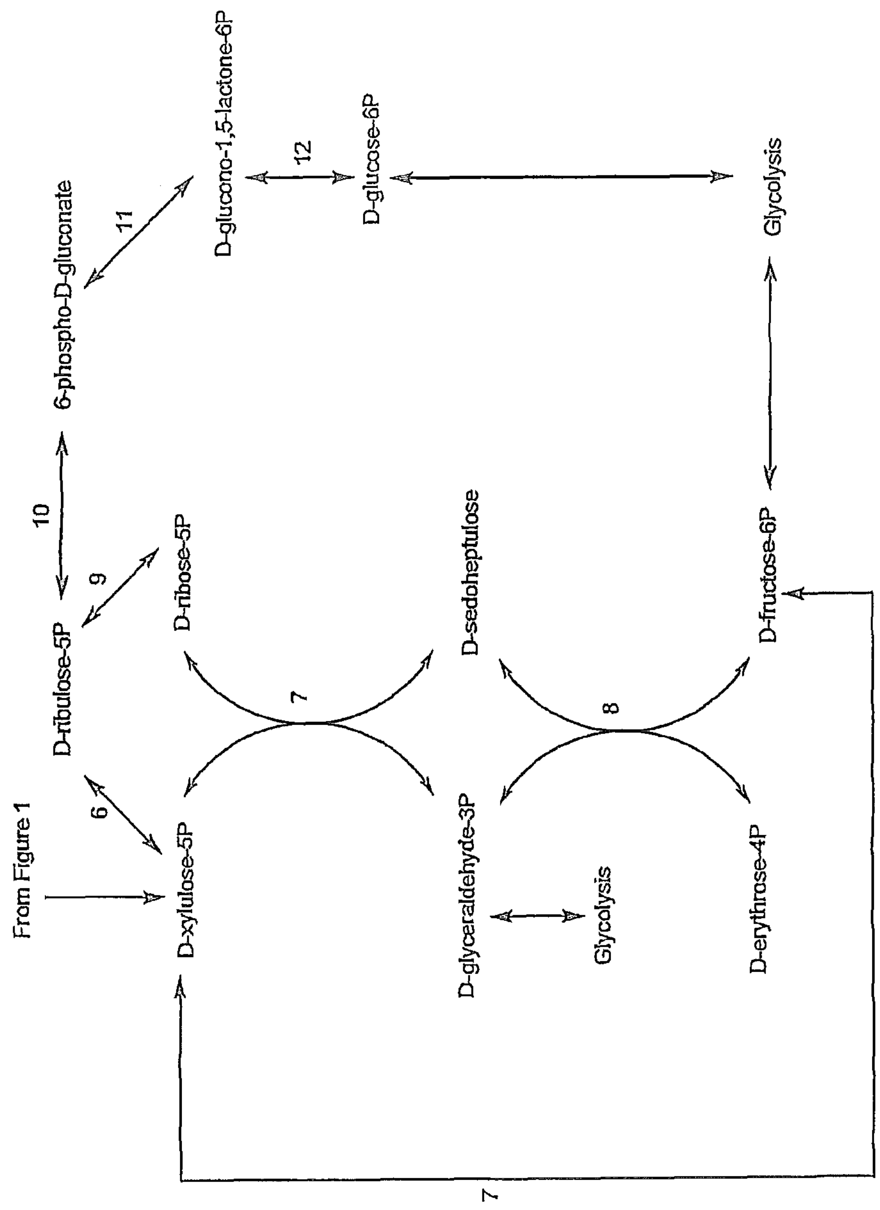
FIGS. 2A-C depict the metabolic pathways for converting D-xylulose-5-P to ethanol.

Xylose utilization by these host cells results in useful products that are produced metabolically by the host cell. In these host cells, D-xylulose may be phosphorylated by a native or recombinant xylulokinase to xylulose-5-P, as depicted in FIG. 1. The xylulose-5-P may be further metabolized by enzymes in the pentose phosphate pathway to products such as glucose-6-P, fructose-6-P, glyceraldehydes-3-P, and the like. The pentose phosphate pathway and relevant enzymes and products are depicted in FIG. 2A. As used herein, the terms "enzyme from the pentose phosphate pathway" and "pentose phosphate pathway enzyme" are used interchangeably to refer to an enzyme from the group of enzymes involved in the pentose phosphate pathway, (i.e., 6. ribulose-5-phosphate ketoisomerase (RK11); 7. transketolase (TKL1); 8. transaldolase (TAL1); 9. ribose-5-phosphate ketolisomerase (RK11); 10. 6-phosphogluconate dehydrogenase (GND1); 11. 6-phosphogluconalactonase (SOL3); and/or 12. glucose-6-phosphate-1-dehydrogenase (ZWF); the reference numbers correspond to those in FIG. 2A).

Figure 2B:
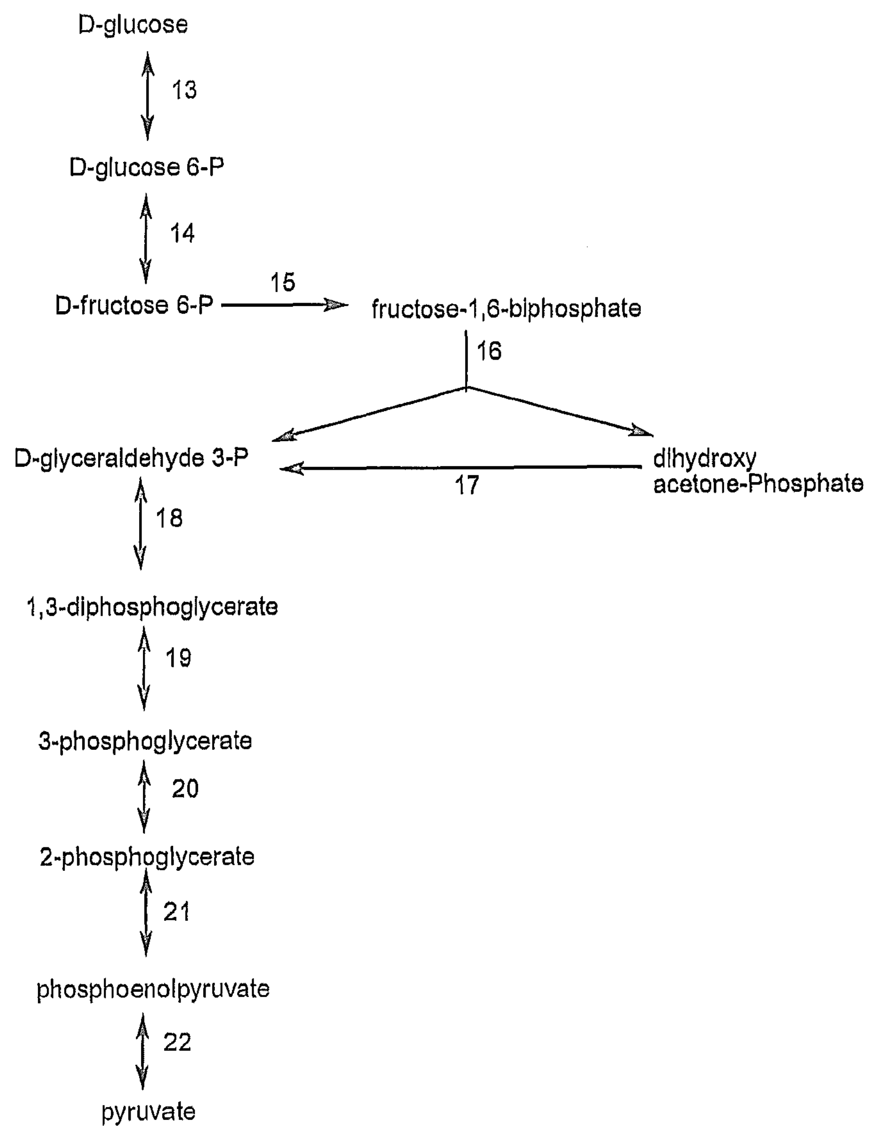

Products of the pentose phosphate pathway may be further metabolized through the process of glycolysis. The metabolic process of glycolysis is depicted in FIG. 2B. As used herein, the term "glycolytic enzyme" refers to an enzyme from the group of enzymes involved in glycolysis (i.e.: 13. hexokinase; 14. phosphoglucose isomerase; 15. phosphofructokinase; 16. aldolase; 17. triose phosphate isomerase; 18. glyceraldehyde phosphate dehydrogenase; 19. phosphoglycerate kinase; 20. phosphglyceromutase; 21. enoase; and/or 22. pyruvate kinase; the reference numbers correspond to those in FIG. 2B).

Figure 2C:
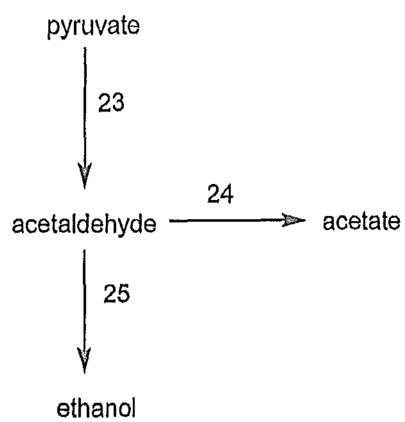

Pyruvate from the glycolytic pathway (i.e., glycolysis) may be further metabolized to ethanol as shown in FIG. 2C by ethanologenic enzymes. As used herein, the term "ethanologenic enzyme" refers to an enzyme involved in the conversion of pyruvate to ethanol, (e.g., a pyruvate decarboxylase, an aldehyde dehydrogenase, and/or an alcohol dehydrogenase). The term "ethanologenic pathway" refers to the pathway depicted in FIG. 2C.

Recombinant host cells transformed with xylose reductase and xylitol dehydrogenase genes are hence capable of converting xylose to xylitol and then converting xylitol to xylulose, which can lead to the production of desirable fermentation products (e.g., an alcohol, such as ethanol, butanol, and the like, including, but not limited to a fatty alcohol [e.g., a C8-C20 fatty alcohol], a fatty acid [e.g., a C8-C20 fatty acid], lactic acid, 3-hydroxpropionic acid, acrylic acid, acetic acid, succinic acid, citric acid, malic acid, fumaric acid, an amino acid, 1,3-propanediol, ethylene, glycerol, a β-lactam, and the like). However, cells transformed with wildtype xylose reductase and xylitol dehydrogenase genes from *Pichia stipitis* convert xylose inefficiently and with accumulation of xylitol (Matsushika et al., Appl. Environ Microbiol., 81:243-55 [2008]). The present application provides improved xylose reductase and xylitol dehydrogenase variants that significantly increase the efficiency of xylose conversion.

Recombinant Nucleic Acid Constructs

The present invention provides recombinant nucleic acid constructs comprising polynucleotide sequences that encode at least one polypeptide comprising an amino acid sequence having at least 70% identity to SEQ ID NO:2, wherein the polypeptide is capable of catalyzing xylose to xylitol, and wherein the polypeptide comprises at least one substitution set forth herein. SEQ ID NO:2 corresponds to the amino acid sequence encoding xylose reductase from the yeast, *Pichia stipitis*. SEQ ID NO:1 corresponds to the native *P. stipitis* polynucleotide sequence that encodes a *P. stipitis* xylose reductase (SEQ ID NO:2), while SEQ ID NOS:3 and 4 correspond to codon-optimized sequences encoding the xylose reductase. In some embodiments, the nucleic acid construct comprises SEQ ID NO:40, while in other embodiments, the nucleic acid construct comprises SEQ ID NO:42, in still other embodiments, the nucleic acid construct comprises SEQ ID NO:44, and in additional embodiments, the nucleic acid construct comprises SEQ ID NO:46. In some embodiments, the polypeptide comprises SEQ ID NO:41, while in other embodiments, the polypeptide comprises SEQ ID NO:43, in still other embodiments, the polypeptide comprises SEQ ID NO:45, and in further embodiments, the polypeptide comprises SEQ ID NO:47.

The present invention also provides a recombinant nucleic acid constructs comprising polynucleotide sequences that encode at least one polypeptide comprising an amino acid sequence having at least 70% identity to SEQ ID NO:6, wherein the polypeptide is capable of catalyzing xylitol to xylulose, and wherein the polypeptide comprises at least one substitution set forth herein. SEQ ID NO:6 corresponds to the amino acid sequence encoding xylitol dehydrogenase from the yeast, *Pichia* SEQ ID NO:5 corresponds to the native *P. stipitis* polynucleotide sequence that encodes a *P. stipitis* xylitol dehydrogenase (SEQ ID NO:6), while SEQ ID NOS:7 and 8 correspond to codon-optimized sequences encoding the xylitol dehydrogenase. In some embodiments, the nucleic acid construct comprises SEQ ID NO:48, while in other embodiments, the nucleic acid construct encodes a polypeptide comprising SEQ ID NO:49.

The present invention also provides recombinant nucleic acid constructs comprising polynucleotide sequences that encode polypeptide sequences having xylose reductase and xylitol dehydrogenase activity. In some embodiments, the nucleic acid constructs comprise at least one of SEQ ID NO:40, 42, 44, and/or 46, and SEQ ID NO:48.

The present invention also provides nucleic acid constructs comprising codon-optimized polynucleotides encoding xylulokinase. In some embodiments, the present invention provides SEQ ID NO:11, while in other embodiments, the present invention provides SEQ ID NO:12.

The present invention also provides nucleic acid constructs comprising polynucleotides encoding xylose reductase, xylitol dehydrogenase and xylulokinase. In some embodiments, the nucleic acid constructs comprise SEQ ID NO:1, 3, 4, 40, 42, 44, and/or 46, as well as SEQ ID NO: 5, 7, 8, and/or 48, and SEQ ID NO:9, 11, and/or 12.

In some embodiments, recombinant nucleic acid constructs of the present invention further comprise a polynucleotide sequence (genetic) element that facilitates integration into a fungal host cell genome, by homologous or non-homologous recombination. In some embodiments, the nucleic acid construct of the present invention further comprises an origin of replication that is functional in a fungal cell (e.g., a yeast origin of replication). Typically, the fungal host cell is a yeast or filamentous fungal cell, more typically, a yeast cell. In some embodiments, nucleic acid constructs of the present invention comprise a transcriptional regulatory element that is functional in a fungal cell. For example, in some embodiments the recombinant nucleic acid construct comprises a promoter sequence and/or transcription terminator sequence that is functional in a fungal cell such that the xylose reductase and/or xylitol dehydrogenase polynucleotide is operatively linked to the promoter sequence and/or transcription terminator sequences.

Xylose reductase and xylitol dehydrogenase polynucleotides that are suitable for use in the practice of the present invention include those encoding variants of SEQ ID NO:2 and/or 6, respectively. These variants include those having amino acid sequences with one or more conservative or non-conservative substitutions relative to the amino acid sequence of SEQ ID NO:2 and/or SEQ ID NO:6. As used herein, the term "conservative substitution" refers to the substitution of a residue for another residue that does not generally alter the specific activity of the encoded polypeptide. An exemplary conservative substitution is a substitution that is within the same group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions that do not generally alter the specific activity are well-known in the art. The most commonly occurring exchanges are Ala/Ser, Val/Ile, Asp/Glu, Thr/Ser, Ala/Gly, Ala/Thr. Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these in reverse.

In some embodiments, polynucleotides encoding conservatively substituted variations of the *P. stipitis* xylose reductase and/or xylitol dehydrogenase employed in the practice of the present invention include substitutions of a small percentage, typically less than about 5%, more typically less than 2%, and often less than about 1% of the amino acids of the polypeptide sequence, with a conservatively selected amino acid of the same conservative substitution group.

Other xylose reductase and/or xylitol dehydrogenase polynucleotides suitable for use in the practice of the present invention include those encoding variants of *P. stipitis* xylose reductase and/or xylitol dehydrogenase generated by mutagenesis, recombination, or other protein engineering method followed by screening of the variants for xylose utilization using a method, such as that described in the Examples. In some embodiments, the resulting variants comprise one or more substitutions (conservative or non-conservative), deletions, and/or insertions. The present invention thus provides methods for making improved *P. stipitis* xylose reductase and xylitol dehydrogenase polynucleotide variants, wherein the method comprises introducing one or more modifications into a polynucleotide encoding SEQ ID NO:1, 3 and/or 4; and/or 5, 7 and/or 8, respectively, to produce a modified polynucleotide, wherein the modification is selected from at least one substitution, at least one deletion, and/or at least one insertion; transforming a host cell with the modified polynucleotide; and screening the transformed host cell for an improvement in a desired phenotype relative to the corresponding untransformed host cell. In some embodiments, the improved variants are screened to assess improvements in a desired phenotype relative to a transformed host cell that has been transformed with wild-type sequences, while in other embodiments, transformed host cells are compared with other transformed host cells. Exemplary phenotypes include improved utilization of a pentose sugar (e.g., xylose, arabinose, etc.), stability, specific activity, lower Ki for xylitol, ethanol/acetate tolerance and/or tolerance to low pH, decreased by-product formation, and/or increased ethanol yield. Exemplary desirable xylose utilization phenotypes include the ability to ferment xylose to ethanol, the ability to ferment xylose to other metabolic intermediates/products, the ability to undergo aerobic or anaerobic growth on xylose, and the like.

Methods for generating variant libraries of polynucleotides encoding modified polypeptides are well known in the art. For example, mutagenesis and directed evolution methods can be readily applied to polynucleotides encoding the xylose reductase polypeptide of SEQ ID NO:2 and/or xylitol dehydrogenase of SEQ ID NO:6, to generate variant libraries that can be expressed, screened, and assayed using the methods described herein. Mutagenesis and directed evolution methods are well known in the art (See e.g., Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In some embodiments, the present invention provides *P. stipitis* polypeptide variants that comprise at least one modification that is a substitution, insertion, and/or deletion relative to SEQ ID NO:2. Typically, the polypeptide variant has from 1 to 2, 1 to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, up to about 50, 75, 100, or 130 modifications.

In some embodiments, the xylose reductase variants of the present invention comprise a substitution at position 276 of wild-type *P. stipitis* xylose reductase. In some alternative embodiments, the xylose reductase variants comprise at least one substitution at positions 2, 49, 132, 233, 267, and/or 276, wherein the positions are numbered by correspondence with the amino acid sequence of *P. stipitis* xylose reductase set forth in SEQ ID NO:2. In some additional embodiments, the substitutions comprise substitutions at R276, P2, A49, K132, S233, I267, and/or R276. In some further embodiments, the substitutions comprise R276W, P2T, A49G, K132N, S233K, I267V, and/or R276W, wherein the positions are numbered by correspondence with the amino acid sequence of *P. stipitis* xylose reductase set forth in SEQ ID NO:2. In some embodiments, the variants comprise substitutions P2T, A49G, and R276W, wherein the positions are numbered by correspondence with the amino acid sequence of *P. stipitis* xylose reductase set forth in SEQ ID NO:2. In some additional embodiments, the variants comprise substitutions P2T, A49G, K132N, S233K, I267V, and R276W, wherein the positions are numbered by correspondence with the amino acid sequence of *P. stipitis* xylose reductase set forth in SEQ ID NO:2. In some additional embodiments, the variants comprise at least one substitution selected from position 2, 3, 7, 11, 14, 17, 23, 24, 33, 36, 46, 47, 49, 56, 62, 68, 89, 97, 102, 108, 114, 116, 123, 132, 134, 143, 152, 155, 157, 162, 168, 184, 206, 219, 224, 225, 226, 228, 246, 231, 232, 233, 236, 240, 242, 245, 246, 249, 252, 255, 261, 266, 267, 275, 276, 279, 281, 282, 283, 285, 297, 301, 302, 303, and 318, wherein the positions are numbered by correspondence with the amino acid sequence of *P. stipitis* xylose reductase set forth in SEQ ID NO:2.

In still some further embodiments, the variants comprise at least one substitution selected from P2, S3, N7, D11, A14, F17, D23, V24, R33, K36, E46, D47, A49, A56, I62, K68, E89, S97, D102, L108, T114, K116, K123, K132, D134, I143, K152, K155, G157, I162, P168, S184, R206, Q219, L224, N225, Q226, R228, A246, N231, T232, S233, F236, T240, K242, A245, A246, G249, P252, V255, S261, A266, I267, P275, R276, E279, K281, D282, V283, S285, A297, I301, N302, L303, and V318, wherein the positions are numbered by correspondence with the amino acid sequence of *P. stipitis* xylose reductase set forth in SEQ ID NO:2.

In some additional embodiments, the substitutions comprise at least one substitution selected from P2T, S3H, S3R, S3W, N7L, D11K, A14V, F17W, D23E, V24G, R33L, R22V, K36Q, E46K, D47G, D47N, A49G, A56E, A56Y, 162V, K68G, K68M, K68R, E89N, E89V, S97R, S97T, D102T, L108Y, T114S, K116Q, K123C, K132A, K132N, D134E, D134H, D134V, I143L, K152A, K152E, K152H, K152Q, K155A, K155D, K155I, K155R, K155Y, G157R, I162L, P168S, S184A, R206S, R206V, Q219H, Q219L, Q219T, L224A, L224S, L224V, N225D, N225E, N225K, N225S, N225Y, Q226D, Q226E, Q226S, Q226V, R228T, N231G, N231H, N231L, N231S, T232A, T232C, T232S, T232V, S233C, S233F, S233G, S233I, S233K, S233V, F236L, T240V, K242L, A245S, A246L, A246S, G249D, P252C, V255I, S261A, S261C, S261N, S261T, A266V, A266C, I267V, P275A, R276M, R276W, E279Q, K281L, K281V, D282C, D282G, D282R, V283H, S285E, S285T, A297H, A297S, I301C, I301Y, N302D, N302G, N302S, L303I, L303V, and V318C, wherein the positions are numbered by correspondence with the amino acid sequence of *P. stipitis* xylose reductase set forth in SEQ ID NO:2.

In some embodiments, the present invention provides polynucleotide sequences encoding xylose reductase variants comprising SEQ ID NO:40, as provided below. In some additional embodiments, the present invention provides polypeptide sequences comprising SEQ ID NO:41, as provided below.

(SEQ ID NO: 40)

```
ATGCCTTCTATTAAGTTGAACTCTGGTTACGACATGCCAGCCGTCGGTT
TCGGCTGTTGGAAAGTTGACGTTGACACCTGTTCTGAACAGGTCTACCG
TGCTATCAAGACCGGTTACAGATTGTTCGACGGTGCCGAAGATTACGCC
AACGAAAAGTTAGTTGGTGCCGGTGTCAAGAAGGCCATTGACGAAGGTA
TCGTCAAGCGTGAAGACTTGTTCCTTACCTCCAAGTTGTGGAACAACTA
CCACCACCCAGACAACGTCGAAAAGGCCTTGAACAGAACCCTTTCTGAC
TTGCAAGTTGACTACGTTGACTTGTTCTTGATCCACTTCCCAGTCACCT
TCAAGTTCGTTCCATTAGAAGAAAAGTACCCACCAGGATTCTACTGTGG
TAAGGGTGACAACTTCGACTACGAAGATGTTCCAATTTTAGAGACCTGG
AAGGCTCTTGAAAAGTTGGTCAAGGCCGGTAAGATCAGGTCTATCGGTG
TTTCTAACTTCCCAGGTGCTTTGCTCTTGGACTTGTTGAGAGGTGCTAC
CATCAAGCCATCTGTCTTGCAAGTTGAACACCACCCATACTTGCAACAA
CCAAGATTGATCGAGTTCGCTCAATCCCGTGGTATTGCTGTCACCGCTT
ACTCTTCGTTCGGTCCTCAATCTTTCGTTGAATTGAACCAAGGTAGAGC
TTTGAACACTTCTCCATTGTTCGAGAACGAAACTATCAAGGCTATCGCT
GCTAAGCACGGTAAGTCTCCAGCTCAAGTCTTGTTGAGATGGTCTTCCC
AAAGAGGCATTGCCATCATTCCAAAGTCCAACACTGTCCCATGGTTGTT
GGAAAACAAGGATGTCAACAGCTTCGACTTGGACGAACAAGATTTCGCT
GACATTGCCAAGTTGGACATCAACTTGAGATTCAACGACCCATGGGACT
GGGACAAGATTCCTATCTTCGTCTAA
```

(SEQ ID NO: 41)

```
MPSIKLNSGYDMPAVGFGCWKVDVDTCSEQVYRAIKTGYRLFDGAEDYA
NEKLVGAGVKKAIDEGIVKREDLFLTSKLWNNYHHPDNVEKALNRTLSD
LQVDYVDLFLIHFPVTFKFVPLEEKYPPGFYCGKGDNFDYEDVPILETW
KALEKLVKAGKIRSIGVSNFPGALLLDLLRGATIKPSVLQVEHHPYLQQ
PRLIEFAQSRGIAVTAYSSFGPQSFVELNQGRALNTSPLFENETIKAIA
AKHGKSPAQVLLRWSSQRGIAIIPKSNTVPWLLENKDVNSFDLDEQDFA
DIAKLDINLRFNDPWDWDKIPIFV
```

In some embodiments, the present invention provides polynucleotide sequences encoding xylose reductase variants comprising SEQ ID NO:42, as provided below. In some additional embodiments, the present invention provides polypeptide sequences comprising SEQ ID NO:43, as provided below.

```
                                            (SEQ ID NO: 42)
ATGACCTCTATTAAGTTGAACTCTGGTTACGACATGCCAGCCGTCGGT
TTCGGCTGTTGGAAAGTTGACGTTGACACCTGTTCTGAACAGGTCTAC
CGTGCTATCAAGACCGGTTACAGATTGTTCGACGGTGCCGAAGATTAC
GGCAACGAAAAGTTAGTTGGTGCCGGTGTCAAGAAGGCCATTGACGAA
GGTATCGTCAAGCGTGAAGACTTGTTCCTTACCTCCAAGTTGTGGAAC
AACTACCACCACCCAGACAACGTCGAAAAGGCCTTGAACAGAACCCTT
TCTGACTTGCAAGTTGACTACGTTGACTTGTTCTTGATCCACTTCCCA
GTCACCTTCAAGTTCGTTCCATTAGAAGAAAAGTACCCACCAGGATTC
TACTGTGGTAAGGGTGACAACTTCGACTACGAAGATGTTCCAATTTTA
GAGACCTGGAAGGCTCTTGAAAAGTTGGTCAAGGCCGGTAAGATCAGG
TCTATCGGTGTTTCTAACTTCCCAGGTGCTTTGCTCTTGGACTTGTTG
AGAGGTGCTACCATCAAGCCATCTGTCTTGCAAGTTGAACACCACCCA
TACTTGCAACAACCAAGATTGATCGAGTTCGCTCAATCCCGTGGTATT
GCTGTCACCGCTTACTCTTCGTTCGGTCCTCAATCTTTCGTTGAATTG
AACCAAGGTAGAGCTTTGAACACTTCTCCATTGTTCGAGAACGAAACT
ATCAAGGCTATCGCTGCTAAGCACGGTAAGTCTCCAGCTCAAGTCTTG
TTGAGATGGTCTTCCCAAAGAGGCATTGCCATCATTCCAAAGTCCAAC
ACTGTCCCATGGTTGTTGGAAAACAAGGATGTCAACAGCTTCGACTTG
GACGAACAAGATTTCGCTGACATTGCCAAGTTGGACATCAACTTGAGA
TTCAACGACCCATGGGACTGGGACAAGATTCCTATCTTCGTCTAA
```

```
                                            (SEQ ID NO: 43)
MTSIKLNSGYDMPAVGFGCWKVDVDTCSEQVYRAIKTGYRLFDGAEDY
GNEKLVGAGVKKAIDEGIVKREDLFLTSKLWNNYHHPDNVEKALNRTL
SDLQVDYVDLFLIHFPVTFKFVPLEEKYPPGFYCGKGDNFDYEDVPIL
ETWKALEKLVKAGKIRSIGVSNFPGALLLDLLRGATIKPSVLQVEHHP
YLQQPRLIEFAQSRGIAVTAYSSFGPQSFVELNQGRALNTSPLFENET
IKAIAAKHGKSPAQVLLRWSSQRGIAIIPKSNTVPWLLENKDVNSFDL
DEQDFADIAKLDINLRFNDPWDWDKIPIFV
```

In some embodiments, the present invention provides polynucleotide sequences encoding xylose reductase variants comprising SEQ ID NO:44, as provided below. In some additional embodiments, the present invention provides polypeptide sequences comprising SEQ ID NO:45, as provided below.

```
                                            (SEQ ID NO: 44)
ATGACCTCTATTAAGTTGAACTCTGGTTACGACATGCCAGCCGTCGGT
TTCGGCTGTTGGAAAGTTGACGTTGACACCTGTTCTGAACAGGTCTAC
CGAGCTATCAAGACCGGTTACAGATTGTTCGACGGTGCCGAAGATTAC
GGCAACGAAAAATTAGTTGGTGCCGGTGTCAAGAAGGCCATTGACGAA
GGTATCGTCAAGCGTGAAGACTTGTTCCTTACCTCCAAGTTGTGGAAC
AACTACCACCACCCAGACAACGTCGAAAAGGCCTTGAACAGAACCCTT
TCTGACTTGCAAGTTGACTACGTTGACTTGTTCTTGATCCACTTCCCA
GTCACCTTCAAGTTCGTTCCATTAGAAGAAAAGTACCCACCAGGATTC
TACTGTGGTAACGGTGACAACTTCGACTACGAAGATGTTCCAATTTTA
GAGACCTGGAAGGCTCTTGAAAAGTTGGTCAAGGCCGGTAAGATCAGG
TCTATCGGTGTTTCTAACTTCCCAGGTGCTTTGCTCTTGGACTTGTTG
AGAGGTGCTACCATCAAGCCATCTGTCTTGCAAGTTGAACACCACCCA
TACTTGCAACAACCAAGATTGATCGAGTTCGCTCAATCCCGTGGTATT
GCTGTCACCGCTTACTCTTCGTTCGGTCCTCAATCTTTCGTTGAATTG
AACCAAGGTAGAGCTTTGAACACTAAGCCATTGTTCGAGAACGAAACT
ATCAAGGCTATCGCTGCTAAGCACGGCAAGAGCCCAGCTCAAGTCTTG
TTGAGATGGTCTTCCCAAAGAGGCATTGCCGTTATTCCAAAGTCCAAC
ACTGTCCCATGGTTGTTGGAAAACAAGGATGTCAACAGCTTCGACTTG
GACGAACAAGATTTCGCTGACATTGCCAAGTTGGACATCAACTTGAGA
TTCAACGACCCATGGGACTGGGACAAGATTCCTATCTTCGTCTAA
```

```
                                            (SEQ ID NO: 45)
MTSIKLNSGYDMPAVGFGCWKVDVDTCSEQVYRAIKTGYRLFDGAEDY
GNEKLVGAGVKKAIDEGIVKREDLFLTSKLWNNYHHPDNVEKALNRTL
SDLQVDYVDLFLIHFPVTFKFVPLEEKYPPGFYCGNGDNFDYEDVPIL
ETWKALEKLVKAGKIRSIGVSNFPGALLLDLLRGATIKPSVLQVEHHP
YLQQPRLIEFAQSRGIAVTAYSSFGPQSFVELNQGRALNTKPLFENET
IKAIAAKHGKSPAQVLLRWSSQRGIAVIPKSNTVPWLLENKDVNSFDL
DEQDFADIAKLDINLRFNDPWDWDKIPIFV
```

In some embodiments, the present invention provides polynucleotide sequences encoding xylose reductase variants comprising SEQ ID NO:46, as provided below. In some additional embodiments, the present invention provides polypeptide sequences comprising SEQ ID NO:47, as provided below.

```
                                            (SEQ ID NO: 46)
ATGCCTTCTATTAAGTTGAACTCTGGTTACGACATGCCAGCCGTCGGT
TTCGGCTGTTGGAAAGTTGACGTTGACACCTGTTCTGAACAGGTCTAC
CGTGCTATCAAGACCGGTTACAGATTGTTCGACGGTGCCGAAGATTAC
GCCAACGAAAAGTTAGTTGGTGCCGGTGTCAAGAAGGCCATTGACGAA
GGTATCGTCAAGCGTGAAGACTTGTTCCTTACCTCCAAGTTGTGGAAC
AACTACCACCACCCAGACAACGTCGAAAAGGCCTTGAACAGAACCCTT
TCTGACTTGCAAGTTGACTACGTTGACTTGTTCTTGATCCACTTCCCA
GTCACCTTCAAGTTCGTTCCATTAGAAGAAAAGTACCCACCAGGATTC
TACTGTGGTAAGGGTGACAACTTCGACTACGAAGATGTTCCAATTTTA
GAGACCTGGAAGGCTCTTGAAAAGTTGGTCAAGGCCGGTAAGATCAGG
TCTATCGGTGTTTCTAACTTCCCAGGTGCTTTGCTCTTGGACTTGTTG
AGAGGTGCTACCATCAAGCCATCTGTCTTGCAAGTTGAACACCACCCA
TACTTGCAACAACCAAGATTGATCGAGTTCGCTCAATCCCGTGGTATT
GCTGTCACCGCTTACTCTTCGTTCGGTCCTCAATCTTTCGTTGAATTG
AACCAAGGTAGAGCTTTGAACACTTCTCCATTGTTCGAGAACGAAACT
ATCAAGGCTATCGCTGCTAAGCACGGTAAGTCTCCAGCTCAAGTCTTG
TTGAGATGGTCTTCCCAAAGAGGCATTGCCATCATTCCAAAGAGCAAT
ACTGTCCCATTCTTGTTGGAAAACAAGGATGTCAACAGCTTCGACTTG
GACGAACAAGATTTCGCTGACATTGCCAAGTTGGACATCAACTTGAGA
TTCAACGACCCATGGGACTGGGACAAGATTCCTATCTTCGTCTAA
```

```
                                            (SEQ ID NO: 47)
MPSIKLNSGYDMPAVGFGCWKVDVDTCSEQVYRAIKTGYRLFDGAEDY
ANEKLVGAGVKKAIDEGIVKREDLFLTSKLWNNYHHPDNVEKALNRTL
SDLQVDYVDLFLIHFPVTFKFVPLEEKYPPGFYCGKGDNFDYEDVPIL
ETWKALEKLVKAGKIRSIGVSNFPGALLLDLLRGATIKPSVLQVEHHP
YLQQPRLIEFAQSRGIAVTAYSSFGPQSFVELNQGRALNTSPLFENET
IKAIAAKHGKSPAQVLLRWSSQRGIAIIPKSNTVPFLLENKDVNSFDL
DEQDFADIAKLDINLRFNDPWDWDKIPIFV
```

In some embodiments, the present invention also provides nucleic acid substitutions in sequences encoding xylose reductase variants (e.g., SEQ ID NOS:1, 3 and/or 4). In some embodiments, the nucleic acids comprise substitutions at positions 42, 82, 99, 156, 201, 280, 306, 354, 358, 378, 408, 438, 478, 511, 585, 670, 688, 703, 747, 751, 766, 855, 849, and/or 906, wherein the positions are numbered by correspondence with the nucleic acid sequence of *P. stipitis* xylose reductase set forth in SEQ ID NO:1, 3 and/or 4. In some embodiments, the substitutions comprise t82a, t99a, g156a, c201t, a280c, c306t, t354g, t358c, a378t, c408t, a426t, c438t, a478c, t511c, a585g, t670c, t688c, t703c, t747c, t751a, t766c, c849g, c855t, and/or c906t, wherein the positions are numbered by correspondence with the nucleic acid sequence of *P. stipitis* xylose reductase set forth in SEQ ID NO:1, 3 and/or 4.

In some embodiments, the present invention further provides xylitol dehydrogenase variants comprising at least one substitution at positions 5, 13, 19, 49, 81, 149, 187, 189, 202, 205, 206, 208, 209, 211, 215, 218, 226, 227, 228, 229, 231, 235, 239, 241, 251, 252, 256, 260, 287, 296, 307, 327, 350, and/or 352, wherein the positions are numbered by correspondence with the amino acid sequence of *P. stipitis* xylose reductase set forth in SEQ ID NO:6.

In some embodiments, the xylitol dehydrogenase variants comprise substitution at position 208, wherein the positions are numbered by correspondence with the amino acid sequence of *P. stipitis* xylitol dehydrogenase set forth in SEQ ID NO:6. In some embodiments, the substitution at position 208 is I208X. In some further embodiments, the substitution at position 208 is I208R. In some embodiments, the xylitol dehydrogenase variants comprise substitutions at position 211, wherein the positions are numbered by correspondence with the amino acid sequence of *P. stipitis* xylitol dehydrogenase set forth in SEQ ID NO:6. In some embodiments, the substitution at position 211 is N211X. In some further embodiments, the substitution is N211K, while in other embodiments, the substitution is N211S, and in still other embodiments, the substitution is N211K.

In some embodiments, the xylitol dehydrogenase variants comprise substitutions at positions 208 and 211, wherein the positions are numbered by correspondence with the amino acid sequence of *P. stipitis* xylitol dehydrogenase set forth in SEQ ID NO:6. In some embodiments, the substitution at position 208 is I208X and the substitution at position 211 is N211X. In some further embodiments, the substitutions comprise I208R and N211K, while in some other embodiments, the substitutions comprise I208R and N211S.

In some embodiments, the xylitol dehydrogenase variants comprise substitutions at positions 209 and 211, wherein the positions are numbered by correspondence with the amino acid sequence of *P. stipitis* xylitol dehydrogenase set forth in SEQ ID NO:6. In some embodiments, the substitutions are F209X and N211X.

In some embodiments, the xylitol dehydrogenase variants comprise substitutions at positions 208, 209 and 211, wherein the positions are numbered by correspondence with the amino acid sequence of *P. stipitis* xylitol dehydrogenase set forth in SEQ ID NO:6. In some embodiments, the substitutions are I208X, F209X, and N211X. In some further embodiments, the substitutions are I208R, F209S, and N211S.

In some embodiments, the present invention also provides nucleic acid substitutions in sequences encoding xylitol dehydrogenase variants (e.g., SEQ ID NOS:5, 7, and/or 8). In some embodiments, the nucleic acids comprise substitutions at positions t24g, c630t, a732g, a768t, and/or a780g, wherein the positions are numbered by correspondence with the nucleic acid sequence of *P. stipitis* xylose reductase set forth in SEQ ID NO:5, 7 and/or 8.

In some embodiments, the present invention provides polypeptides that comprise XR and XD substitutions, including, but not limited to combinations of substitutions at positions 271, 270, 272, and/or 276 in XR (wherein the positions are numbered by correspondence with SEQ ID NO:2) and substitutions at positions 208, 209, and/or 211 in XD (wherein the positions are numbered by correspondence with SEQ ID NO:6). In some embodiments, the substitutions comprise substitutions S271X, K270, N272, and/or R276 in XR (wherein the positions are numbered by correspondence with SEQ ID NO:2) and substitutions I208X, F209X, and/or N211X in XD (wherein the positions are numbered by correspondence with SEQ ID NO:6). In some embodiments, the substitutions comprise substitutions S271G, K270R, N272P, and/or R276F in XR (wherein the positions are numbered by correspondence with SEQ ID NO:2) and substitutions I208R, F209S, and/or N211K in XD (wherein the positions are numbered by correspondence with SEQ ID NO:6).

In some embodiments, the substitutions comprise R276F in XR (wherein the position is numbered by correspondence with SEQ ID NO:2), and I208R in XD (wherein the position is numbered by correspondence with SEQ ID NO:6). In some embodiments, the substitutions comprises R276F in XR (wherein the position is numbered by correspondence with SEQ ID NO:2), and F209S and N211K in XD (wherein the positions are numbered by correspondence with SEQ ID NO:6). In some embodiments, the substitutions comprise S271G in XR (wherein the position is numbered by correspondence with SEQ ID NO:2), and I208R and N211K in XD (wherein the positions are numbered by correspondence with SEQ ID NO:6). In some embodiments, the substitutions comprise S271G in XR (wherein the position is numbered by correspondence with SEQ ID NO:2), and I208R and N211S in XD (wherein the positions are numbered by correspondence with SEQ ID NO:6). In some embodiments, the substitutions comprise R276F in XR (wherein the position is numbered by correspondence with SEQ ID NO:2), and I208R, F209S and N211K in XD (wherein the positions are numbered by correspondence with SEQ ID NO:6). In some embodiments, the substitutions comprise S271G in XR (wherein the position is numbered by correspondence with SEQ ID NO:2), and I208R in XD (wherein the positions are numbered by correspondence with SEQ ID NO:6). In some embodiments, the substitutions comprise K270R in XR (wherein the position is numbered by correspondence with SEQ ID NO:2), and I208R and N211R in XD (wherein the positions are numbered by correspondence with SEQ ID NO:6). In some embodiments, the substitutions comprise K270R in XR (wherein the position is numbered by correspondence with SEQ ID NO:2), and F209S and N211K in XD (wherein the positions are numbered by correspondence with SEQ ID NO:6). In some embodiments, the substitutions comprise N272P and R276F in XR (wherein the position is numbered by correspondence with SEQ ID NO:2), and F209S and N211K in XD (wherein the positions are numbered by correspondence with SEQ ID NO:6). In some embodiments, the substitutions comprise K270R, N272P and R276F in XR (wherein the position is numbered by correspondence with SEQ ID NO:2), and N211K in XD (wherein the positions are numbered by correspondence with SEQ ID NO:6).

In some additional embodiments, the present invention provides XR and XD variants having amino acid and nucleic acid substitutions, wherein amino acid substitutions in SEQ ID NO:2 comprises R276F, amino acid substitutions in SEQ ID NO:6 comprise I208R, and the nucleic acid substitutions comprise t811a and c816t in SEQ ID NO:1, 3 and/or 4. In some additional embodiments, the present invention provides XR and XD variants having amino acid and nucleic acid substitutions, wherein amino acid substitutions in SEQ ID NO:2 comprise R276F, amino acid substitutions in SEQ ID NO:6 comprise F209S and N211K, and the nucleic acid substitutions comprise t811a and c816t in SEQ ID NO:1, 3 and/or 4. In some additional embodiments, the present invention provides XR and XD variants having amino acid and nucleic acid substitutions, wherein amino acid substitutions in SEQ ID NO:2 comprise S271G, amino acid substitutions in SEQ ID NO:6 comprise I208R and N211K, and the nucleic acid substitutions comprise c816t and a826c in SEQ ID NO:1, 3 and/or 4. In some additional embodiments, the present invention provides XR and XD variants having amino acid and nucleic acid substitutions, wherein amino acid substitutions in SEQ ID NO:2 comprise S271G, amino acid substitutions in SEQ ID NO:6 comprise I208R and N211S, and the nucleic acid substitutions comprise c816t and a826c in SEQ ID NO:1, 3 and/or 4. In some additional embodiments, the present invention provides XR and XD variants having amino acid and nucleic acid substitutions, wherein amino acid substitutions in SEQ ID NO:2 comprise R276F, amino acid substitutions in SEQ ID NO:6 comprise I208R, F209S and N211K, and the nucleic acid substitutions comprise t811a and c816t in SEQ ID NO:1, 3 and/or 4. In some additional embodiments, the present invention provides XR and XD variants having amino acid and nucleic acid substitutions, wherein amino acid substitutions in SEQ ID NO:2 comprise S271G, amino acid substitutions in SEQ ID NO:6 comprise I208R, and the nucleic acid substitutions comprise c816t and a826c in SEQ ID NO:1, 3 and/or 4. In some additional embodiments, the present invention provides XR and XD variants having amino acid and nucleic acid substitutions, wherein amino acid substitutions in SEQ ID NO:2 comprise K270R, amino acid substitutions in SEQ ID NO:6 comprise I208R and N211R, and the nucleic acid substitutions comprise t811a, c816t, and a826c, in SEQ ID NO:1, 3 and/or 4. In some additional embodiments, the present invention provides XR and XD variants having amino acid and nucleic acid substitutions, wherein amino acid substitutions in SEQ ID NO:2 comprise K270R, amino acid substitutions in SEQ ID NO:6 comprise F209S and N211K, and the nucleic acid substitutions comprise t811a, c816t, and a826c, in SEQ ID NO:1, 3 and/or 4. In some additional embodiments, the present invention provides XR and XD variants having amino acid and nucleic acid substitutions, wherein amino acid substitutions in SEQ ID NO:2 comprise K272P and R276F, amino acid substitutions in SEQ ID NO:6 comprise F209S and N211K, and the nucleic acid substitutions comprise t811a in SEQ ID NO:1, 3 and/or 4. In some additional embodiments, the present invention provides XR and XD variants having amino acid and nucleic acid substitutions, wherein amino acid substitutions in SEQ ID NO:2 comprise K270R, N272P, and R276F, amino acid substitutions in SEQ ID NO:6 comprise N211K, and the nucleic acid substitutions comprise t811a in SEQ ID NO:1, 3 and/or 4. In some additional embodiments, the present invention provides XR and XD variants having amino acid and nucleic acid substitutions, wherein amino acid substitutions in SEQ ID NO:6 comprise I208R, and the nucleic acid substitutions comprise t811a, c816t, and a826c, in SEQ ID NO:1, 3 and/or 4.

In some embodiments, the present invention provides polynucleotide sequences encoding xylitol dehydrogenase variants comprising SEQ ID NO:48, as provided below. In some additional embodiments, the present invention provides polypeptide sequences comprising SEQ ID NO:49, as provided below.

```
                                     (SEQ ID NO: 48)
ATGACCGCTAATCCCTCTCTTGTTTTGAATAAGATTGACGACATTTCT
TTTGAAACTTACGATGCTCCCGAAATTAGCGAACCCACAGACGTTTTA
GTTCAAGTTAAAAAAACTGGTATCTGCGGTTCTGACATCCACTTCTAC
GCTCATGGAAGGATCGGCAACTTCGTCTTAACAAAGCCAATGGTTCTG
GGTCATGAAAGCGCGGGTACTGTTGTTCAAGTCGGTAAAGGTGTTACT
TCACTGAAGGTTGGTGATAACGTCGCAATCGAGCCCGGTATTCCATCT
AGGTTCAGTGATGAGTACAAATCTGGTCACTACAACCTGTGTCCACAC
ATGGCATTTGCTGCTACTCCCAATTCTAAAGAGGGTGAACCAAACCCA
CCAGGAACTCTATGTAAGTACTTCAAATCTCCAGAAGACTTCCTGGTT
AAGTTACCCGATCATGTTTCTTTGGAGTTGGGTGCTTTGGTCGAGCCA
CTATCTGTTGGGGTCCATGCTAGTAAATTAGGCTCCGTTGCATTTGGC
GATTACGTTGCTGTTTTTGGTGCTGGTCCAGTAGGATTACTGGCTGCC
GCTGTCGCTAAGACATTTGGTGCCAAGGGTGTGATTGTCGTTGATATA
TCTGACAAGAAGCTGAAGATGGCCAAAGACATAGGTGCCGCTACACAT
ACCTTCAACTCCAAGACGGGAGGTAGTGAAGAATTGATCAAAGCCTTC
GGTGGTAATGTACCAAATGTTGTCTTGGAATGTACTGGGGCTGAACCA
TGTATTAAGCTAGGTGTTGATGCCATCGCACCAGGTGGTAGATTCGTG
CAAGTTGGTAATGCTGCTGGTCCCGTGTCCTTTCCCATAACAGTGTTC
GCTATGAAAGAACTTACTTTGTTTGGTTCATTTCGTTATGGTTTCAAC
GACTATAAGACAGCCGTGGGTATCTTTGATACTAACTACCAGAACGGT
AGAGAGAATGCTCCCATTGACTTTGAACAGCTTATCACGCACAGATAC
AAATTCAAAGACGCCATTGAAGCCTACGACCTAGTAAGAGCAGGTAAA
GGGGCTGTCAAGTGTTTGATTGATGGTCCAGAATAA
```

```
                                     (SEQ ID NO: 49)
MTANPSLVLNKIDDISFETYDAPEISEPTDVLVQVKKTGICGSDIHFY
AHGRIGNFVLTKPMVLGHESAGTVVQVGKGVTSLKVGDNVAIEPGIPS
RFSDEYKSGHYNLCPHMAFAATPNSKEGEPNPPGTLCKYFKSPEDFLV
KLPDHVSLELGALVEPLSVGVHASKLGSVAFGDYVAVFGAGPVGLLAA
AVAKTFGAKGVIVVDISDKKLKMAKDIGAATHTFNSKTGGSEELIKAF
GGNVPNVVLECTGAEPCIKLGVDAIAPGGRFVQVGNAAGPVSFPITVF
AMKELTLFGSFRYGFNDYKTAVGIFDTNYQNGRENAPIDFEQLITHRY
KFKDAIEAYDLVRAGKGAVKCLIDGPE
```

In some embodiments, the present invention provides polynucleotide sequences encoding xylose reductase variants comprising SEQ ID NO:46 and xylitol dehydrogenase variants comprising SEQ ID NO:48. In some additional embodiments, the present invention provides polypeptide sequences comprising SEQ ID NO:47 and SEQ ID NO:49.

Also suitable for use in the practice of the present invention are polynucleotides encoding a truncated variant of *P. stipitis* xylose reductase and/or a truncated variant xylitol dehydrogenase capable of catalyzing xylose to xylitol and/or xylitol to xylulose. In some embodiments, these truncation variants are truncated at the carboxy (C)-terminus and/or the amino (N)-terminus. Typically, the truncation is from about 1 to about 50 amino acid residues in length.

Those having ordinary skill in the art will understand that due to the degeneracy of the genetic code, a multitude of nucleotide sequences that encode the xylose isomerase polypeptides described herein exist. Table 1 provides the standard triplet genetic code for each amino acid. For example, the codons AGA, AGG, CGA, CGC, CGG, and CGU all encode the amino acid arginine. Thus, at every position in the nucleic acids referred to herein, where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

TABLE 1

Genetic Code

| Amino Acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In some embodiments, DNA sequences are designed for high codon usage bias (i.e., codons that are used at higher frequency in the protein coding regions than other codons that code for the same amino acid). In some embodiments, the preferred codons are determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available (See e.g., Henaut and Danchin in Neidhardt et al. [eds.], *Escherichia coli and Salmonella*, ASM Press, Washington D.C., [1987], p. 2047-2066, which is incorporated herein by reference).

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See, GCG CodonPreference, Genetics Computer Group Wisconsin Package; Peden, *Codon W*, University of Nottingham; McInerney, Bioinform., 14:372-73 [1998]; Stenico et al., Nucl. Acids Res. 222437-46 [1994]; Wright, Gene 87:23-29 [1990]; Wada et al., Nucl. Acids Res., 20:2111-2118 [1992]; Nakamura et al., Nucl. Acids Res., 28:292 [2000]; and Henaut and Danchin, supra; all of which are incorporated herein by reference). The data source for obtaining codon usage may rely on any available nucleotide sequence capable of coding for a protein. These data sets include nucleic acid sequences actually known to express proteins (e.g., complete protein coding sequences-CDS), expressed sequence tags (ESTs), or predicted coding regions of genomic sequences (See e.g., Mount, *Bioinformatics: Sequence and Genome Analysis*, Chapter 8, Cold Spring Harbor Laboratory Press, Cold Spring Harbor, N.Y., [2001]; Uberbacher, Methods Enzymol., 266:259-281 [1996]; and Tiwari et al., Comput. Appl. Biosci. 13:263-270 [1997]; all of which are incorporated herein by reference).

In some embodiments, the xylose reductase and xylitol dehydrogenase polynucleotides contain codons optimized for expression in a fungal cell, particularly a yeast cell. In some embodiments, codon-optimized xylose reductase polynucleotide sequence is provided as SEQ ID NOS:3 and 4. In addition, codon-optimized xylitol dehydrogenase polynucleotides are provided herein (SEQ ID NOS:7 and 8), as well as codon-optimized xylulokinase polynucleotides (SEQ ID NOS:11 and 12). In some embodiments, the codon-optimized sequences provide various advantages, as compared to the corresponding wild-type *S. cerevisiae* sequence(s).

Certain silent mutations have been identified in *P. stipitis* xylose reductase and xylitol dehydrogenase polynucleotide variants that appear to confer the property of greater xylose utilization in transformed *Saccharomyces cerevisiae*. These variants are described in the Examples. The silent mutations include t24g, t82a, t99a, g156a, c201t, a280c, c306t, t354g, t358c, a378t, c408t, a426t, c438t, a478c, t511c, a585g, c630t, t670c, t688c, t703c, a732g, t747c, t751a, t766c, a768t, a780g, t811a, c816t, a826c, c849g, c855t, and c906t (where the nucleotide position is determined by alignment with SEQ ID NO:1). However, it is not intended that the present invention be limited to these particular substitutions as alternative substitutions find use in the present invention.

In some embodiments, the xylose reductase and/or xylitol dehydrogenase polynucleotides are employed in recombinant nucleic acid constructs that comprise a vector (e.g., a plasmid, a cosmid, a phage, a virus, a yeast artificial chromosome (YAC), and the like), into which a xylose reductase and/or xylitol dehydrogenase polynucleotide sequence has been inserted. The xylose reductase and xylitol dehydrogenase polynucleotides provided herein find use when incorporated into any one of a variety of vectors. Suitable vectors include, but are not limited to chromosomal, nonchromosomal and synthetic DNA sequences, yeast plasmids, vectors derived from combinations of plasmids and phage DNA, and many others. Any suitable vector that transduces genetic material into a cell, and, if replication is desired, which is replicable and viable in the relevant host find use in the present invention.

Nucleic acid constructs of the present invention find use in transforming a host cell to permit the host to express the xylose reductase and/or xylitol dehydrogenase polypeptide. Methods for recombinant expression of proteins in fungi are well known in the art, and a number of vectors are available or can be constructed using routine methods (See e.g., Zhu et al., Plasmid 6:128-33 [2009], incorporated herein by reference; and the many standard reference works in this field).

In some embodiments, recombinant nucleic acid constructs of the present invention further comprise a transcriptional regulatory element that is functional in a fungal cell. In some embodiments, the nucleic acid construct comprises the xylose reductase and/or xylitol dehydrogenase polynucleotide operatively linked to a transcriptional regulatory sequence (e.g., a promoter, transcription termination sequence, and the like), that is functional in a fungal cell. Examples of promoters that are functional in a fungal host cell include, but are not limited to promoters from yeast and filamentous fungi. Promoters that are suitable for use in the practice of the present invention include endogenous or heterologous promoters and include both constitutive and inducible promoters that are natural or modified. Particularly useful promoters are those that are insensitive to catabolite (glucose) repression and/or do not require xylose for induction. Such promoters are well known in the art. In some embodiments, a promoter sequence is operably linked to the 5' region of the xylose isomerase or xylitol dehydrogenase coding sequence using routine methods that are well known in the art.

Promoters that are suitable for use in the practice of the present invention include, but are not limited to yeast promoters from glycolytic genes (e.g., yeast phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters, and the like; See e.g., WO 93/03159, which is incorporated herein by reference); promoters of glucose transporters; ribosomal protein encoding gene promoters; alcohol dehydrogenase promoters (e.g., ADH1, ADH4, and the like), and the enolase promoter (ENO).

Exemplary promoters that are useful for directing the transcription of the nucleic acid constructs of the present invention in yeast host cells include, but are not limited to those from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH1/ADH2/GAP), and *Saccharomyces cerevisiae* 3-phosphoglycerate kinase, *Saccharomyces cerevisiae* transcription elongation factor (TEF), *Saccharomyces cerevisiae* fructose 1,6-bisphosphate aldolase (FBA1), and *Saccharomyces cerevisiae* 3-phosphate glycerate kinase (PGK1). Other useful promoters for yeast host cells are well known in the art (See e.g., Romanos et al., Yeast 8:423-488 [1992], which is incorporated herein by reference).

Suitable filamentous fungal promoters that are useful in the practice of the present invention include, but are not limited to promoters obtained from the genes for *Aspergillus oryzeae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787, which is incorporated herein by reference), as well as the NA2-tpi promoter (a hybrid of the promoters from the genes for *Aspergillus niger* neutral alpha-amylase and *Aspergillus oryzae* those phosphate isomerase), promoters such as cbh1, cbh2, egl1, egl2, pepA, hfb1, hfb2, xyn1, amy, and glaA (See, Nunberg et al., Mol. Cell Biol., 4:2306-2315 [1984]; Boel et al., EMBO J. 3:1581-85 [1984]; and EP 0 137 280A, all of which are incorporated herein by reference), and mutant, truncated, and hybrid promoters thereof. Promoters associated with chitinase production in fungi also find use in some embodiments (See e.g., Blaiseau and Lafay, Gene 120: 243-248 [1992] [filamentous fungus *Aphanocladium album*]; and Limon et al., Curr. Genet, 28:478-83 [1995] [*Trichoderma harzianum*]; both of which are incorporated herein by reference).

Any other suitable promoter sequence that drives expression in a fungal host cell, particularly a yeast host cell finds use in the present invention. Suitable promoter sequences can be identified using well known methods. In one approach, a putative promoter sequence is linked 5' to a sequence encoding a reporter protein, the construct is transfected into the host cell and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (See, Henriksen et al., Microbiol., 145:729-34 [1999], which is incorporated herein by reference) or a lacZ reporter gene (See, Punt et al., Gene, 197:189-93 [1997], which is incorporated herein by reference). In some embodiments, functional promoters are derived from naturally occurring promoter sequences by directed evolution methods (See e.g., Wright et al., Hum. Gene Ther., 16:881-892 [2005], which is incorporated herein by reference).

Exemplary transcription termination sequences (terminators) that are functional in a fungal host cell, include transcription termination sequences from yeast and filamentous fungi, that are well known in the art. In some embodiments, the transcription termination sequence is from a yeast. Exemplary yeast transcription termination sequences include, but are not limited to CYC1, ADH1t, ADH2t, etc. In some embodiments, the nucleic acid constructs of the present invention contain a ribosome binding site for translation initiation. In some embodiments, the construct includes appropriate sequences for amplifying expression (e.g., an enhancer). Such elements are well known in the art and any suitable enhancers and/or transcription termination sequences, and/or ribosome binding sites find use in the present invention.

In some additional embodiments, nucleic acid constructs of the present invention contain one or more selectable marker genes to provide a phenotypic trait for selection of transformed host cells. Suitable marker genes include, but are not limited to those coding for antimicrobial resistance such as, ampicillin (ampR), kanamycin, chloramphenicol, tetracycline, streptomycin or spectinomycin (e.g., the aada gene); including but not limited to the streptomycin phosphotransferase (spt) gene coding for streptomycin resistance, the neomycin phosphotransferase (nptII) gene encoding kanamycin or geneticin resistance, the nourseothricin actetyltransferase (nat1) gene coding for nourseothricin resistance, the hygromycin phosphotransferase (hpt) gene coding for hygromycin resistance, genes encoding dihydrofolate reductase, phleomycin, or neomycin resistance for eukaryotic cell culture, and tetracycline or ampicillin resistance in *E. coli*, as well as other marker genes that are well known in the art.

Nucleic acid constructs of the present invention typically comprise a fungal origin of replication, such as, for example, a filamentous fungal or yeast origin of replication. Typically, the recombinant nucleic acid constructs of the present invention comprise a yeast origin of replication. Examples include, but are not limited to constructs containing autonomous replicating sequences, constructs containing 2 micron DNA including the autonomous replicating sequence and rep genes, constructs containing centromeres like the CEN6, CEN4, CEN11, CDN3 and autonomous replicating sequences, and other like sequences that are well known in the art. Exemplary nucleic acid constructs include constructs suitable for transforming yeast. These include, but are not limited to episomal constructs based on the yeast 2μ or CEN origin based plasmids like pYES2/CT, pYES3/CT, pESC/His, pESC/Ura, pESC/Trp, pES/Leu, p427TEF, pRS405, pRS406, pRS413, and other yeast-based constructs that are known in the art.

In some embodiments, the nucleic acid constructs of the present invention comprise elements to facilitate integration of the xylose reductase and/or xylitol dehydrogenase polynucleotide into a fungal host chromosome (i.e., the genome), by either homologous or non-homologous recombination and either site-directed or random mutagenesis. In some embodiments, the nucleic acid constructs comprise elements that facilitate homologous integration. In some embodiments, the xylose reductase and/or xylitol dehydrogenase polynucleotide is integrated at one or more site and is present in one or more copies. In some embodiments, the nucleic acid construct comprises the xylose reductase and/or xylitol dehydrogenase polynucleotide(s) and no promoter that is operatively linked to the xylose reductase and/or xylitol dehydrogenase polynucleotide. This type of construct typically comprises genetic elements to facilitate integration into the fungal host chromosome at a location that is downstream of a native promoter (i.e., in the host chromosome). In some embodiments, a second nucleic acid construct is employed which comprises a promoter and genetic elements to facilitate integration into the fungal host chromosome in a location upstream of the targeted integration site of the xylose reductase and/or xylitol dehydrogenase polynucleotide. In some embodiments, the nucleic acid construct comprises the xylose reductase and/or xylitol dehydrogenase polynucleotide operatively linked to a promoter or promoter and terminator sequences such that all are integrated into the host chromosome (genome).

Genetic elements that facilitate integration by homologous recombination are those having sequence homology to targeted integration sites in the fungal host chromosome (genome). Suitable sites that find use as targets for integration include, but are not limited to the TY1 loci, the RDN loci, the ura3 locus, the GPD locus, aldose reductase (GRE3) locus, etc. Those having ordinary skill in the art appreciate that additional sites for integration can be readily identified using methods known in the art, including but not limited to microarray analysis, metabolic flux analysis, comparative genome hybridization analysis, etc.

Genetic elements or techniques which facilitate integration by non-homologous recombination include, but are not limited to restriction enzyme-mediated integration (REMI) (See e.g., Manivasakam et al., Mol. Cell Biol., 18(3):1736-1745 [1998], which is incorporated herein by reference), transposon-mediated integration, and other elements and methods that are well known in the art.

In some embodiments, the nucleic acid constructs of the present invention comprise at least one further recombinant polynucleotide that is capable of conferring a desired phenotype to a fungal host cell, particularly in the context of xylose fermentation. In some embodiments, the recombinant polynucleotide that is capable of conferring an improved phenotype to the fungal host cell is a non-coding polynucleotide such as a regulatory polynucleotide, a coding polynucleotide, or combination thereof.

Exemplary further desired phenotypes include, but are not limited to increased transport of xylose into the host cell, increased xylulose kinase activity, increased flux through the pentose phosphate pathway, decreased sensitivity to catabolite repression, increased tolerance to ethanol, increased tolerance to increased osmolarity, increased tolerance to organic acids, reduced production of by-products, and other similar properties related to increasing flux through the pentose phosphate and glycolysis pathways to produce a desired metabolic product/intermediate at higher levels as compared to the corresponding wild-type host cell. Typically, the desired metabolic product is an alcohol (e.g., ethanol).

In some embodiments, nucleic acid constructs comprising at least one further polynucleotide that is capable of conferring a desired phenotype to a fungal host cell comprise a polynucleotide encoding a protein known to impact the desired phenotype, wherein the polynucleotide is either native or heterologous to the fungal host cell. In some embodiments, this polynucleotide is operatively linked to its native promoter, or to a heterologous promoter (i.e., a promoter that is not associated with the polynucleotide in the corresponding native gene). In some embodiments, the at least one further polynucleotide is overexpressed. In some embodiments, the nucleic acid constructs comprise multiple copies of a least one polynucleotide. Suitable polynucleotides include, but are not limited to those that facilitate overexpression of proteins known to have an impact on the desired phenotype.

Exemplary recombinant polynucleotides that are capable of conferring a desired phenotype to a fungal host cell include recombinant polynucleotides (either wild-type or mutated forms) which encode a xylose or hexose transporter, a xylulose kinase (XKS), an enzyme from the pentose phosphate pathway (See e.g., FIG. 2A), a glycolytic enzyme (i.e., from the glycolytic metabolic pathway; See e.g., FIG. 2B), and an ethanologenic enzyme (See e.g., FIG. 2C), regulatory sequences that enhance expression of these sequences, and combinations thereof. Additional recombinant polynucleotides (either wild-type or mutated forms) that find use in the present invention include those that encode additional proteins involved in the pentose phosphate, glycolysis, and ethanologenic pathways (See e.g., FIGS. 2A-C).

Exemplary transporters include, but are not limited to GXF1, SUT1 and At6g59250 from *Candida intermedia, Pichia stipitis* and *Arabidopsis thaliana*, respectively (See e.g., Runquist et al., Biotechnol. Biofuels., 3:5 [2010], which is incorporated herein by reference), as well as HXT4, HXT5, HXT7, GAL2, AGT1, GXF2 (See e.g., Matsushika et al., Appl. Microbiol. Biotechnol., 84:37-53 [2009], which is incorporated herein by reference). In some embodiments, overexpression of native *S. cerevisiae* transporters is desirable, particularly HXT5 and HXT7.

Particularly suitable recombinant polynucleotides include those which encode: a xylulose kinase (XK); an enzyme from the pentose phosphate pathway (e.g., a ribulose-5-phosphate 3-epimerase (RPE1), a ribose-5-phosphate ketol-isomerase (RKI1), a transketolase (TKL1), a transaldolase (TAL1), etc.); a glycolytic enzyme (e.g., a hexokinase (HXK1/HXK2), a glyceraldehyde-3-phosphate dehydrogenase (GAPDH), a pyruvate kinase (PVK2), etc.); and an ethanologenic enzyme (e.g., a pyruvate decarboxylase, an alcohol dehydrogenase, etc.).

Exemplary regulatory polynucleotides include promoters, enhancer, terminator, and other regulatory elements that function to improve the expression of polynucleotides in a fungal host cell, particularly, a yeast host cell. These include, but are not limited to the regulatory elements described hereinabove.

The nucleic acid constructs described herein are useful for transforming fungal host cells to confer to these cells the property of xylose utilization.

Recombinant Fungal Host Cells

The present invention provides recombinant fungal host cells comprising at least one xylose reductase and/or xylitol dehydrogenase polynucleotide provided herein. More specifically, the recombinant fungal host cell comprises a polynucleotide sequence that encodes a polypeptide which is capable of catalyzing xylose to xylitol, wherein the polynucleotide is selected from: (a) a polynucleotide that encodes a polypeptide comprising an amino acid sequence that is at least about 70% identical to SEQ ID NO:2, wherein the polypeptide comprises at least one substitution set forth herein; and (b) a polynucleotide that hybridizes under stringent hybridization conditions to the complement of a polynucleotide encoding a polypeptide having the amino acid sequence of SEQ ID NO:2, wherein the polypeptide comprises at least one substitution set forth herein. In some other embodiments, the recombinant fungal host cell comprises a polynucleotide sequence that encodes a polypeptide which is capable of catalyzing xylitol to xylulose, wherein the polynucleotide is selected from: (a) a polynucleotide that encodes a polypeptide comprising an amino acid sequence that is at least about 70% identical to SEQ ID NO:6, wherein the polypeptide comprises at least one substitution as set forth herein; and (b) a polynucleotide that hybridizes under stringent hybridization conditions to the complement of a polynucleotide encoding a polypeptide having the amino acid sequence of SEQ ID NO:6, wherein the polypeptide comprises at least one substitution set forth herein. In some embodiments, the recombinant fungal host cell comprises polynucleotide sequences that encode a polypeptide which is capable of catalyzing xylose to xylitol and a polypeptide capable of catalyzing xylitol to xylulose-5-P, wherein the polynucleotides are selected from: (a) polynucleotides that encode polypeptides comprising amino acid sequences that are at least about 70% identical to SEQ ID NO:2 and/or 6, wherein each of the polypeptides comprise at least one substitution set forth herein; and (b) polynucleotides that hybridize under stringent hybridization conditions to the complement of polynucleotides encoding polypeptides having the amino acid sequences of SEQ ID NO:2 and/or 6, wherein each of the polypeptides comprise at least one substitution set forth herein.

In some embodiments, the recombinant fungal host cell further comprises at least one xylulokinase, including but not limited to the xylulokinase provided herein (SEQ ID NO:10), encoded by SEQ ID NO:9, and by codon-optimized sequences SEQ ID NOS:11 and 12.

In some embodiments, the recombinant fungal host cell comprises at least one xylose reductase, at least one xylitol dehydrogenase, and at least one xylulokinase. In some embodiments, the xylose reductase comprises SEQ ID NO:2, 41, 43, 45, and/or 47, In some embodiments, the xylitol dehydrogenase comprises SEQ ID NO:6 and/or 42. In some embodiments, the xylulokinase comprises SEQ ID NO:10.

In some embodiments, the present invention provides a recombinant fungal host cell comprising or transformed with a nucleic acid construct of the present invention. In some embodiments, the xylose reductase and/or xylitol dehydrogenase and/or xylulokinase polynucleotide is integrated into the host cell genome. Typically, the recombinant fungal host cell is a filamentous fungal or yeast host cell. More typically, the recombinant fungal host cell is a yeast host cell.

The present invention also provides methods for producing a recombinant fungal host cell, wherein the method comprises: (a) providing at least one nucleic acid construct of the present invention, wherein the nucleic acid construct comprises at least one xylose reductase and/or xylitol dehydrogenase and/or at least one xylulokinase polynucleotide provided herein; and (b) transforming a fungal host cell with the nucleic acid construct to produce a recombinant fungal host cell. In some additional embodiments, the recombinant fungal host cell is transformed using nucleic acid constructs comprising from about two to about fifty copies of at least one xylose reductase and/or xylitol dehydrogenase and/or xylulokinase. It is not intended that the present invention be limited to any particular copy number of xylose reductase and/or xylitol dehydrogenase genes and/or xylulokinase, as any suitable number of copies finds use in the present invention. In some embodiments, the nucleic acid constructs comprise any combination of wild-type and/or variant xylose reductase and/or xylitol dehydrogenase and/or xylulokinase. Furthermore, any suitable method for introducing multiple copies of either xylose reductase and/or xylitol dehydrogenase and/or xylulokinase find use in the present invention.

Introduction of the expression construct of the present invention into the host cell can be accomplished using any suitable method, including but not limited to calcium phosphate transfection, DEAE-dextran mediated transfection, electroporation, or any other suitable technique. Indeed, there are numerous methods known in the art and described in various standard reference texts. In some embodiments, the xylose reductase and/or xylitol dehydrogenase and/or xylulokinase polynucleotide sequence is integrated into the host cell genome.

Suitable fungal host cells include yeast and filamentous fungal host cells. In some embodiments, the fungal host cell is a yeast cell. Exemplary yeast host cells that are useful in the practice of the present invention include, but are not limited to *Candida, Hansenula, Saccharomyces, Schizosaccharomyces, Pichia, Kluyveromyces*, and *Yarrowia*. In some embodiments of the invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*. In some embodiments, the yeast host cell is *Saccharomyces* species. In some additional embodiments, the yeast host cell is *Saccharomyces cerevisiae.*

Any suitable yeast strain finds use in the present invention, including but not limited to strains such as those commercially available from companies such as Lallemand (e.g., Superstart™, THERMOSACC®, etc.); RED STAR and ETHANOL RED® (Fermentis/Lesaffre); FALI (AB Maui); (Baker's Best Yeast, Baker's Compressed Yeast, etc. (Fleishmann's Yeast); BIOFERM AFT, XP, CF, and XR (North American Bioproducts Corp.); Turbo Yeast (Gert Strand AB); FERMIOL® (DSM Specialties); BY4741 (e.g., ATCC 201388); Y108-1 (ATCC PTA.10567) and LNH-ST (See, US Pat. Publ. No. 2011/0159560); NRRL YB-1952 (ARS Culture Collection), as well as any additional suitable strains.

In some embodiments, the filamentous fungal host cell is a species of *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothia, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms or taxonomic equivalents thereof. However, it is not intended that the present invention be limited to any particular species of filamentous fungal host cell. Exemplary filamentous fungal host cells that find use in the present invention include, but are not limited to a filamentous fungal host cell of the *Trichoderma* species (e.g., *T. longibrachiatum, T. viride* [e.g., ATCC 32098 and 32086], *T. reesei* [NRRL 15709, ATTC 13631, 56764, 56765, 56466, 56767, and RL-P37 and derivatives thereof; See e.g., Sheir-Neiss et al., Appl. Microbiol. Biotechnol., 20:46-53 [1984], incorporated herein by reference), *T. koningii*, and *T. harzianum*), as well as *Hypocrea jecorina*. The term "*Trichoderma*" refers to any fungal strain that was previously classified as *Trichoderma* or is currently classified as *Trichoderma.*

In some embodiments of the present invention, the filamentous fungal host cell is an *Aspergillus* species (e.g., *A. awamori, A. funigatus, A. japonicas, A. nidulans, A. niger, A. aculeatus, A. foetidus, A. oryzae, A. sojae*, or *A. kawachi* (See e.g., Kelly and Hynes, EMBO J., 4:475479 [1985]; NRRL 3112, ATCC 11490, 22342, 44733, and 14331; Yelton et al., Proc. Natl. Acad. Sci. USA, 81, 1480-1474 [1984]; Tilburn et al., Gene 26, 205-221 [1982]; and Johnston et al., EMBO J., 4:1307-1311 [1985], all of which are incorporated herein by reference). In some embodiments of the invention, the filamentous fungal host cell is a *Fusarium* species (e.g., *F. bactridioides, F. cerealis, F. crookwellense, F. culmorum, F. graminaearum, F. graminum, F. oxysporum, F. rosium*, or *F. venenatum*). In some embodiments of the invention, the filamentous fungal host cell is of a *Neurospora* species (e.g., *N. crassa*; See e.g., Case, et al., Proc. Natl. Acad. Sci. USA, 76:5259-5263 [1979]; U.S. Pat. No. 4,486,553; and Kinsey and Rambosek, Mol. Cell. Biol., 4:117-122 [1984], all of which are incorporated herein by reference). In some embodiments of the invention, the filamentous fungal host cell is of a *Humicola* species (e.g., *H. insolens, H. grisea*, or *H. lanuginose*). In some embodiments of the invention, the filamentous fungal host cell is a *Mucor* species (e.g., *M. miehei* or *M. circinelloides*). In some embodiments of the invention, the filamentous fungal host cell is a *Rhizopus* species (e.g., *R. oryzae* or *R. niveus*). In some embodiments of the invention, the filamentous fungal host cell is of a *Penicillum* species (e.g., *P. purpurogenum, P. chrysogenum*, or *P. verruculosum*). In some embodiments of the invention, the filamentous fungal host cell is a *Thielavia* species (e.g., *T. terrestris*). In some embodiments of the invention, the filamentous fungal host cell is a *Tolypocladium* species (e.g., *T. inflatum* or *T. geodes*). In some embodiments of the invention, the filamentous fungal host cell is a *Trametes* species (e.g., *T. villosa* or *T. versi-*

*color*). In some embodiments of the invention, the filamentous fungal host cell is a *Chrysosporium* species, (e.g., *C. lucknowense, C. keratinophilum, C. tropicum, C. merdarium, C. inops, C. pannicola*, or *C. zonatum*).

Strains that find use in the present invention include those that are readily accessible to the public from a number of culture collection, including but not limited to the American Type Culture Collection (ATCC), Deutsche Sammlung von Mikroorganismen and Zellkutlturen GmbH (DSM), Centraalbureau Voor Schimmelcultures (CBS), and Agricultural Research Service Patent Culture Collection, Northern Regional Research Center (NRRL).

Recombinant fungal host cells of the present invention are capable of fermenting xylose when provided with a xylose based culture medium. Typically the recombinant fungal host cells described herein are capable of fermenting xylose at a faster rate compared to the corresponding wild-type fungal host cell. In some embodiments, the recombinant fungal host cells provided herein are capable of fermenting xylose at a faster rate compared to fungal host cells transformed with a nucleic acid construct comprising xylose reductase and/or xylitol dehydrogenase genes. In some other embodiments, the recombinant fungal host cells provided herein are capable of fermenting xylose at a faster rate compared to fungal host cells transformed with a nucleic acid construct comprising of xylose reductase, xylitol dehydrogenase and/or xylulose kinase genes. In some embodiments, the recombinant fungal host cells are capable of fermenting xylose at a rate of at least about 1 g/L/h and sometimes at a rate of at least about 2 g/L/h. Exemplary xylose-based culture media include culture media which have been formulated to contain xylose, as well as feedstock from cellulosic saccharification processes and/or feedstock from a hemicellulose pre-treatment process (i.e., a "hemicellulosic feedstock").

In some embodiments, the fungal host cell is a wild-type fungal cell, while in other embodiments, it is a mutated or otherwise altered or engineered form of a wild-type fungal cell. Typically, the fungal host cell (either wild-type or otherwise altered or engineered) comprises polynucleotides encoding a xylulokinase and one or more enzymes in the pentose phosphate, glycolytic, and/or ethanologenic pathways. In some embodiments, the fungal host cell comprises polynucleotides encoding a xylulokinase and all of the enzymes in the pentose phosphate, glycolytic, and ethanologenic pathways. In some embodiments, the fungal host cell comprises recombinant polynucleotides encoding enzymes that are heterologous to the fungal host cell (i.e., not native to the fungal host cell). In some additional embodiments, the fungal host cell is engineered to comprise other metabolic pathways that utilize products/intermediates from the pentose phosphate, glycolytic, and/or enthanologenic pathways to produce other desirable products. For example, in some embodiments, the fungal host cell is engineered to comprise a metabolic pathway for the biosynthesis of a fatty alcohol or fatty acid (See e.g., WO 2007/136762, which is incorporated herein by reference). In some embodiments, the fatty alcohol or fatty acid is a C8-C20 fatty acid or fatty alcohol. In some embodiments, the fungal host cell is altered or engineered to overexpress any one or more of the polynucleotides encoding the enzymes in one or more of these metabolic pathways.

In some embodiments, the recombinant fungal host cell of the present invention further comprises genetic modifications in addition to the xylose reductase and/or xylitol dehydrogenase polynucleotide. In some embodiments, in addition to having a xylose reductase and/or xylitol dehydrogenase polynucleotide described herein, the recombinant host cell comprises at least one different recombinant polynucleotide that is capable of conferring a further desired phenotype to the fungal host cell. In some embodiments, the present invention provides a recombinant fungal host cell comprising at least one *P. stipitis* xylose reductase and/or xylitol dehydrogenase polynucleotide or variant thereof as described herein, and at least one recombinant polynucleotide that encodes a polypeptide which differs from the *P. stipitis* xylose reductase and/or xylitol dehydrogenase and/or variant(s) thereof, wherein the recombinant polynucleotide imparts a desired phenotype to the fungal host cell. It is contemplated that in some embodiments, the recombinant polynucleotide that is capable of conferring a desired phenotype to the fungal host cell is introduced to the fungal host cell on the same nucleic construct as the xylose reductase and/or xylitol dehydrogenase polynucleotide, or on a separate nucleic acid construct. Nucleic acid constructs of the present invention comprising at least one xylose reductase and xylitol dehydrogenase polynucleotides and at least one further recombinant polynucleotide capable of conferring a desired phenotype to the fungal host cell are also provided by the present invention.

In some embodiments, the recombinant polynucleotide that is capable of conferring a desired phenotype to the fungal host cell is a non-coding polynucleotide (e.g., a regulatory polynucleotide, a coding polynucleotide, or a combination thereof). As described above, exemplary further desired phenotypes include, but are not limited to increased transport of xylose into the host cell, increased xylulose kinase activity, increased flux through the pentose phosphate pathway, decreased sensitivity to catabolite repression, increased tolerance to ethanol, increased tolerance to increased osmolarity, increased tolerance to organic acids, reduced production of by-products, and other like properties related to increasing flux through the pentose phosphate, glycolysis, and/or ethanologenic pathways to produce the desired metabolic product/intermediate at higher levels as compared to the corresponding wild-type host cell. In some embodiments, the desired metabolic product is an alcohol (e.g., ethanol).

In some embodiments, recombinant fungal host cells comprising at least one further polynucleotide capable of conferring a desired phenotype to the fungal host cell comprise at least one polynucleotide encoding a protein known to impact the desired phenotype, wherein the polynucleotide is either native or heterologous to the fungal host cell. In some embodiments, the polynucleotide(s) are operatively linked to its native promoter, while in other embodiments, the polynucleotide is operatively linked to a heterologous promoter (i.e., one not associated with the polynucleotide in the corresponding native gene). In some embodiments, the polynucleotide is overexpressed. In some embodiments, the recombinant fungal host cell comprises multiple copies of the polynucleotide. Suitable polynucleotides include, but are not limited to those that facilitate overexpression of proteins known to have an impact on the desired phenotype. Therefore, in some embodiments, the fungal host cell is altered or engineered to overexpress one or more polynucleotides.

In some embodiments, recombinant polynucleotides that are capable of imparting a desired phenotype to a fungal host cell include, but are not limited to recombinant polynucleotides which encode a xylose or hexose transporter, a xylulose kinase (XKS), an enzyme from the pentose phosphate pathway (See e.g., FIG. 2A), a glycolytic enzyme (i.e., from the metabolic pathway of glycolysis; See e.g., FIG. 2B), and an ethanologenic enzyme (See e.g., FIG. 2C), the regulatory sequences associated with these sequences, and any combination thereof.

Exemplary transporters that find use in the present invention include, but are not limited to GXF1, SUT1 and At6g59250 from *Candida intermedia, Pichia supitis*, and *Arabidopsis thaliana*, respectively (See e.g., Runquist et al., 84:37-53 [2010], incorporated herein by reference), HXT4, HXT5, HXT7, GAL2, AGT1, and GXF2, (See e.g., Matsushika et al., Appl. Microbiol. Biotechnol., 84:37-53 [2009]). In some embodiments, overexpression of native *S. cerevisiae* transporters is desirable, particularly HXT5 and HXT7.

Particularly suitable recombinant polynucleotides include, but are not limited to those that encode: a xylulose kinase (XK); an enzyme from the pentose phosphate pathway (e.g., a ribulose-5-phosphate 3-epimerase (RPE1), a ribose-5-phosphate ketol-isomerase (RKI1), a transketolase (TKL1), a transaldolase (TAL1), etc.); a glycolytic enzyme (e.g., a hexokinase (HXK1/HXK2), a glyceraldehyde-3-phosphate dehydrogenase (GAPDH), a pyruvate kinase (PVK2), etc.; and an ethanologenic enzyme (e.g., a pyruvate decarboxylase, an alcohol dehydrogenase, etc.).

Exemplary regulatory polynucleotides include promoters, enhancer, terminator, and other regulatory elements that function to improve the expression of polynucleotides in a fungal host cell, particularly, a yeast host cell, as described above.

In some embodiments, recombinant host cells of the present invention comprise one or more native genes deleted from its genome. In some embodiments, the deletion(s) cause removal or diminishment of a biological activity that is otherwise exhibited by the fungal host cell. In some embodiments, the cumulative effect of the deletion(s) also leads to an improvement in a phenotype of the fungal host cell. Any suitable method for deleting gene finds use in the present invention. There are numerous methods well known in the art.

For example, in some embodiments, recombinant host cells of the present invention have certain native genes deleted from the host genome in order to improve the utilization of pentose sugars (e.g., xylose), increase transport of xylose into the host cell, increase xylulose kinase activity, increase flux through the pentose phosphate pathway, decrease sensitivity to catabolite repression, increase tolerance to ethanol/acetate, increase tolerance to increased osmolarity, increase tolerance to organic acids (low pH), reduce production of by-products, and other like properties related to increasing flux through the relevant pathways to produce ethanol and other desired metabolic products at higher levels, where comparison is made with respect to the corresponding host cell without the deletion(s). Genes targeted for deletion include, but are not limited to genes encoding enzymes in the pentose phosphate pathway, a glycolytic enzyme, and/or an ethanologenic enzyme.

In some embodiments, other genes are targeted for deletion, including but not limited to those encoding aldose reductase (GRE3) (See e.g., Matsushika et al., Appl. Microbiol. Biotechnol., 84:37-53 [2009]), sorbitol dehydrogenases (SOR1/SOR2), a glutamate dehydrogenase (GDH1), a 6-phosphogluconate dehydrogenase (GND), a glucose-5-phosphate dehydrogenase (ZWF1), and any enzyme for which its deletion is known in the art to improve the utilization of a pentose sugar, decrease by-product formation, and/or increase the ethanol yield of a fungal host cell. The genes encoding these enzymes in many fungi are known in the art. Those having ordinary skill in the art appreciate that additional genes encoding these enzymes can be readily identified by microarray analysis (See e.g., Sedlak et al., Yeast 21:671-684 [2004]), metabolic flux analysis (See e.g., Sonderegger et al., Appl. Environ. Microbiol., 70(4):2307-2317 [2004]), in silico modeling (See e.g Hjersted et al., Biotechnol. Bioengineer. 97(5):1190-1204 [2007]), chemogenomics (See e.g Teixeira et al., Appl. Environ. Microbiol., 75(18):5761-5772 [2009]), and other well known methods.

In some embodiments, the host cells employed in the practice of the present invention are mutagenized and/or evolved to exhibit further desired phenotypes, for example, further improvement in the utilization of pentose sugars (e.g., xylose, arabinose, etc.), increased transport of xylose into the host cell, increased xylulose kinase activity, increased flux through the pentose phosphate pathway, decreased sensitivity to catabolite repression, increased tolerance to ethanol/acetate, increased tolerance to increased osmolarity, increased tolerance to organic acids (low pH), reduced production of by-products, and other like properties related to increasing flux through the pentose phosphate and glycolysis pathways to produce a desired metabolic product/intermediate at higher levels. In some embodiments, the desired metabolic product is an alcohol (e.g., ethanol). In some embodiments, the host cells are mutagenized and/or evolved using known methods either prior to or after transformation with the xylose reductase and/or xylitol dehydrogenase polynucleotide. These methods include, but are not limited to classical mutagenesis, whole genome shuffling, evolutionary engineering methods, which employ screening and/or selection methods, or any combination of such well known methods.

Classical mutagenesis methods include, but are not limited to treatment of the host cell with a mutagen such as a chemical mutagen or irradiation exposure (e.g., ultraviolet or gamma-irradiation). Whole genome shuffling methods involving, for example, recombination of genomic DNA between native genomic DNA sequences and/or variants thereof, can be facilitated by sexual mating, protoplast fusion methods and other methods well known in the art (See e.g., WO 98/31837 and WO 2000/04190, incorporated herein by reference). These methods are coupled with screening and/or selection methods to identify altered fungal host cells that exhibit the desired phenotype. For example, such methods find use in altering or engineering a fungal host cell to overexpress one or more desired polynucleotides.

Mutagenesis may be performed in accordance with any of the techniques known in the art, including random and site-specific mutagenesis. Directed evolution can be performed with any of the techniques known in the art to screen for improved promoter variants including shuffling. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03, 344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related US and non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986];

Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

Evolutionary engineering can be done by prolonged cultivation and selection of strains under desired conditions through chemostat, turbidostat or batch cultures. Evolutionary engineering methods can be practiced under either aerobic or anaerobic conditions. Selection strategies can be optimized by varying culture conditions, for example, carbon source, nitrogen source, aeration, pH and temperature. Methods for evolutionary engineering are well known in the art (See e.g., Wisselink et al., Appl. Environ. Microbiol., 75(4): 907-914 [2009]; Kuyper et al., FEMS Yeast Res., 5:399-409 [2005]; and Sauer, Adv. Biochem. Engineer. Biotechnol., 73:129-169 [2001], all of which are incorporated herein by reference).

Therefore, in some embodiments, the recombinant fungal host cell comprising a xylose reductase and/or xylitol dehydrogenase polynucleotide exhibits an improved phenotype relative to the corresponding fungal host cell without the xylose reductase and/or xylitol dehydrogenase polynucleotide.

In some embodiments, whole genome shuffling and evolutionary engineering methods result in increased copy number of xylose reductase and/or xylitol dehydrogenase and/or xylulokinase from two to fifty copies. It is not intended that the present invention be limited to any particular copy number of xylose reductase and/or xylitol dehydrogenase genes and/or xylulokinase, as any suitable number of copies finds use in the present invention. In some embodiments, the nucleic acid constructs comprise any combination of wild-type and/or variant xylose reductase and/or xylitol dehydrogenase and/or xylulokinase. Furthermore, any suitable method of increasing copies of either xylose reductase and/or xylitol dehydrogenase and/or xylulokinase finds use in the present invention.

In some embodiments, the improved phenotype comprises further improvement in the utilization of pentose sugars (e.g., xylose, arabinose, etc.), increased transport of xylose into the host cell, increased xylulose kinase activity, increased flux through the pentose phosphate pathway, decreased sensitivity to catabolite repression, increased tolerance to ethanol/acetate, increased tolerance to increased osmolarity, increased tolerance to organic acids (low pH), and reduced production of by products, or other properties.

Fermentation

The present invention provides processes for producing fermentation products, wherein the method comprises: (a) providing the recombinant fungal cell of the present invention; (b) providing a fermentation medium comprising xylose; (c) contacting the fermentation medium with the recombinant fungal cell under conditions suitable for generating the fermentation product; and optionally (d) recovering the fermentation product. In some embodiments, the fermentation product is an alcohol (e.g., ethanol, butanol, etc.), a fatty alcohol (e.g., a C8-C20 fatty alcohol), a fatty acid (e.g., a C8-C20 fatty acid), lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., cephalosporin). However, it is contemplated that other fermentation products will be produced using the methods of the present invention.

In some embodiments, the fermentation medium is feedstock from a cellulosic saccharification process and/or feedstock from a hemicellulose pre-treatment process. Such feedstocks include, but are not limited to carbohydrates (e.g., lignocellulose, xylans, cellulose, starch, etc.), other sugars (e.g., glucose, xylose, arabinose, etc.), and other compositions. Compositions of fermentation media suitable for the growth of yeast and filamentous fungi are well known in the art and there are various reference texts that provide recipes for these media.

Fermentation conditions suitable for generating desired fermentation products are well known in the art and any suitable method finds use in the present invention. In some embodiments, the fermentation process is carried out under aerobic or microaerobic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generated NAD+. In some embodiments of the present invention, when the fermentation process is carried out under anaerobic conditions, pyruvate may be reduced to a fermentation product such as ethanol, butanol, lactic acid, 3-hydroxypropionic acid, acrylic acid, acetic acid, succinic acid, citric acid, malic acid, fumaric acid, an amino acid, 1,3-propanediol, ethylene, glycerol, and/or β-lactam (e.g., a cephalosporin).

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C.

In some embodiments, recombinant host cells of the present invention are grown under batch or continuous fermentation conditions. Classical batch fermentation is a closed system, wherein the composition of the medium is set at the beginning of the fermentation and is not subject to artificial alterations during the fermentation. A variation of the batch system is a fed-batch fermentation, which also finds use in the present invention. In this variation, the substrate is added in increments as the fermentation progresses. Fed-batch systems are useful when catabolite repression is likely to inhibit the metabolism of the cells and/or where it is desirable to have limited amounts of substrate in the medium. Batch and fed-batch fermentations are common and well known in the art. Continuous fermentation is an open system where a defined fermentation generally maintains the culture at a constant high density where cells are primarily in log phase growth. Continuous fermentation systems strive to maintain steady state growth conditions. Methods for modulating nutrients and growth factors for continuous fermentation processes, as well as techniques for modulating nutrients and growth factors for continuous fermentation processes as well as techniques for maximizing the rate of product formation are well known in the art of industrial microbiology.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); HPLC (high pressure liquid chromatography); MES (2-N-morpholino ethanesulfonic acid); FIOPC (fold improvements over positive control); YPD (10 g/L yeast extract, 20 g/L peptone, and 20 g/L dextrose); SOE-PCR (splicing by overlapping extension PCR); ARS (ARS Culture Collection or NRRL Culture Collection, Peoria, Ill.); Axygen (Axygen, Inc., Union City, Calif.); Lallemand (Lallemand Ethanol Technology, Milwaukee, Wis.); Dual Biosystems (Dual Biosystems AG, Schlieven, Switzerland); Megazyme (Megazyme International Ireland, Ltd., Wicklow, Ireland); Dasgip (Dasgip Biotools, LLC, Shrewsbury, Mass.); Difco (Difco Laboratories, BD Diagnostic Systems, Detroit, Mich.); PCRdiagnostics (PCRdiagnostics, by *E coli* SRO, Slovak Republic); Agilent (Agilent Technologies, Inc., Santa Clara, Calif.); and Bio-Rad (Bio-Rad Laboratories, Hercules, Calif.).

The following sequences find use in the present invention. SEQ ID NO:2 provides the polypeptide sequence of *P. stipitis* xylose reductase ("XR.1"), while SEQ ID NO:1 provides the native polynucleotide sequence, SEQ ID NO:3 provides one codon optimized DNA sequence ("XR.2"), and SEQ ID NO:4 provides an alternative codon optimized DNA sequence ("XR.3"). SEQ ID NO:6 provides the polypeptide sequence of *P. stipitis* xylitol dehydrogenase ("XD.1"), while SEQ ID NO:5 provides the native polynucleotide sequence, SEQ ID NO:7 provides one codon optimized DNA sequence ("XD.2"), and SEQ ID NO:8 provides an alternative codon optimized DNA sequence ("XD.3"). SEQ ID NO:10 provides the polypeptide sequence of *S. cerevisiae* xylulokinase ("XK.1"), SEQ ID NO:9 provides the native polynucleotide sequence, SEQ ID NO:11 provides one codon optimized DNA sequence ("XK.2"), and SEQ ID NO:12 provides an alternative codon optimized DNA sequence ("XK.3").

(SEQ ID NO: 2)

```
MPSIKLNSGYDMPAVGFGCWKVDVDTCSEQIYRAIKTGYRLFDGAEDYA
NEKLVGAGVKKAIDEGIVKREDLFLTSKLWNNYHHPDNVEKALNRTLSD
LQVDYVDLFLIHFPVTFKFVPLEEKYPPGFYCGKGDNFDYEDVPILETW
KALEKLVKAGKIRSIGVSNFPGALLLDLLRGATIKPSVLQVEHHPYLQQ
PRLIEFAQSRGIAVTAYSSFGPQSFVELNQGRALNTSPLFENETIKAIA
AKHGKSPAQVLLRWSSQRGIAIIPKSNTVPRLLENKDVNSFDLDEQDFA
DIAKLDINLRFNDPWDWDKIPIFV
```

(SEQ ID NO: 1)

```
ATGCCTTCTATTAAGTTGAACTCTGGTTACGACATGCCAGCCGTCGGTT
TCGGCTGTTGGAAAGTCGACGTCGACACCTGTTCTGAACAGATCTACCG
TGCTATCAAGACCGGTTACAGATTGTTCGACGGTGCCGAAGATTACGCC
AACGAAAAGTTAGTTGGTGCCGGTGTCAAGAAGGCCATTGACGAAGGTA
TCGTCAAGCGTGAAGACTTGTTCCTTACCTCCAAGTTGTGGAACAACTA
CCACCACCCAGACAACGTCGAAAAGGCCTTGAACAGAACCCTTTCTGAC
```

-continued

```
TTGCAAGTTGACTACGTTGACTTGTTCTTGATCCACTTCCCAGTCACCT
TCAAGTTCGTTCCATTAGAAGAAAAGTACCCACCAGGATTCTACTGTGG
TAAGGGTGACAACTTCGACTACGAAGATGTTCCAATTTTAGAGACCTGG
AAGGCTCTTGAAAAGTTGGTCAAGGCCGGTAAGATCAGATCTATCGGTG
TTTCTAACTTCCCAGGTGCTTTGCTCTTGGACTTGTTGAGAGGTGCTAC
CATCAAGCCATCTGTCTTGCAAGTTGAACACCACCCATACTTGCAACAA
CCAAGATTGATCGAATTCGCTCAATCCCGTGGTATTGCTGTCACCGCTT
ACTCTTCGTTCGGTCCTCAATCTTTCGTTGAATTGAACCAAGGTAGAGC
TTTGAACACTTCTCCATTGTTCGAGAACGAAACTATCAAGGCTATCGCT
GCTAAGCACGGTAAGTCTCCAGCTCAAGTCTTGTTGAGATGGTCTTCCC
AAAGAGGCATTGCCATCATTCCAAAGTCCAACACTGTCCCAAGATTGTT
GGAAAACAAGGACGTCAACAGCTTCGACTTGGACGAACAAGATTTCGCT
GACATTGCCAAGTTGGACATCAACTTGAGATTCAACGACCCATGGGACT
GGGACAAGATTCCTATCTTCGTCTAATAA
```

(SEQ ID NO: 3)

```
ATGCCCTCCATAAAGCTAAACTCTGGTTATGATATGCCTGCCGTTGGAT
TCGGTTGTTGGAAAGTAGATGTTGATACCTGCTCAGAACAGATTTATAG
GGCTATTAAAACAGGTTACAGGTTGTTCGACGGTGCCGAGGACTACGCG
AATGAGAAGTTAGTTGGAGCTGGTGTTAAGAAGGCCATCGACGAGGGCA
TTGTTAAGAGGGAGGACCTGTTCTTAACGTCTAAACTGTGGAATAACTA
TCACCACCCAGACAATGTTGAAAAAGCCCTGAATAGAACTTTGAGTGAT
TTGCAGGTGGATTACGTTGACTTGTTTCTAATCCATTTCCCCGTTACTT
TCAAGTTCGTCCCTTTAGAGGAGAAGTATCCACCAGGTTTCTATTGTGG
TAAGGGCGACAACTTCGACTATGAAGATGTTCCTATTCTGGAGACCTGG
AAGGCTCTGGAGAAACTGGTCAAGGCAGGCAAAATAAGGTCCATAGGCG
TCTCTAACTTCCCAGGAGCACTACTGCTTGACTTGTTGAGGGGAGCTAC
CATCAAACCTTCAGTCTTGCAAGTTGAACACCACCCCTATTTGCAACAA
CCCAGGCTGATAGAGTTTGCTCAATCCAGAGGTATAGCTGTTACTGCAT
ACTCTTCCTTTGGACCTCAATCCTTCGTCGAACTTAACCAAGGTAGAGC
GTTGAATACTTCCCCCTTGTTCGAGAATGAAACTATCAAGGCTATTGCG
GCTAAGCACGGTAAGTCACCAGCTCAAGTGTTACTTAGATGGTCTTCCC
AAAGGGGTATCGCAATCATTCCAAAGTCTAACACTGTTCCCAGATTGTT
GGAGAATAAAGATGTTAATTCTTTCGATTTGGACGAACAAGACTTTGCA
GACATAGCCAAACTAGATATTAATCTGAGATTCAATGATCCCTGGGATT
GGGACAAGATACCAATCTTCGTTTAATAA
```

(SEQ ID NO: 4)

```
ATGCCATCTATTAAGTTGAACTCTGGTTACGACATGCCAGCTGTCGGTT
TCGGTTGTAAGGTTGACGTTGACACCTGTTCTGAACAAATTTACAGAGC
TATTAAGACCGGTTACAGATTGTTCGACGGTGCTGAAGACTACGCTAAC
GAAAAGTTGGTTGGTGCTGGTGTCAAGAAGGCTATTGACGAAGGTATTG
TCAAGAGAGAAGACTTGTTCTTGACCTCTAAGTTGAACAACTACCACCA
CCCAGACAACGTCGAAAAGGCTTTGAACAGAACCTTGTCTGACTTGCAA
GTTGACTACGTTGACTTGTTCTTGATTCACTTCCCAGTCACCTTCAAGT
TCGTCCCATTGGAAGAAAAGTACCCACCAGGTTTCTACTGTGGTAAGGG
TGACAACTTCGACTACGAAGACGTTCCAATTTTGGAAACCAAGGCTTTG
GAAAAGTTGGTTAAGGCTGGTAAGATTAGGTCTATTGGTGTTTCTAACT
TCCCAGGTGCTTTGTTGTTGGACTTGTTGAGAGGTGCTACCATTAAGCC
ATCTGTTTTGCAAGTTGAACACCACCCATACTTGCAACAACCAAGATTG
ATTGAGTTCGCTCAATCTAGGGGTATTGCTGTCACCGCTTACTCTTCTT
TCGGTCCACAATCTTTCGTCGAATTGAACCAAGGTAGAGCTTTGAACAC
CTCTCCATTGTTCGAAAACGAAACCATTAAGGCTATTGCTGCTAAGCAC
GGTAAGTCTCCAGCTCAAGTCTTGTTGAGGTCTTCTCAAAGAGGTATTG
CTATTATTCCAAAGTCTAACACCGTCCCAAGATTGTTGGAAAACAAGGA
CGTTAACTCTTTCGACTTGGACGAACAAGACTTCGCTGACATTGCTAAG
TTGGACATTAACTTGAGATTCAACGACCCAGACGACAAGATTCCAATTT
TCGTTTAATAA
```

(SEQ ID NO: 6)

```
MTANPSLVLNKIDDISFETYDAPEISEPTDVLVQVKKTGICGSDIHFYA
HGRIGNFVLTKPMVLGHESAGTVVQVGKGVTSLKVGDNVAIEPGIPSRF
SDEYKSGHYNLCPHMAFAATPNSKEGEPNPPGTLCKYFKSPEDFLVKLP
DHVSLELGALVEPLSVGVHASKLGSVAFGDYVAVFGAGPVGLLAAAVAK
TFGAKGVIVVDIFDNKLKMAKDIGAATHTFNSKTGGSEELIKAFGGNVP
NVVLECTGAEPCIKLGVDAIAPGGRFVQVGNAAGPVSFPITVFAMKELT
LFGSFRYGFNDYKTAVGIFDTNYQNGRENAPIDFEQLITHRYKFKDAIE
AYDLVRAGKGAVKCLIDGPE
```

(SEQ ID NO: 5)

```
ATGACTGCTAACCCTTCCTTGGTGTTGAACAAGATCGACGACATTTCGT
TCGAAACTTACGATGCCCCAGAAATCTCTGAACCTACCGATGTCCTCGT
CCAGGTCAAGAAAACCGGTATCTGTGGTTCCGACATCCACTTCTACGCC
CATGGTAGAATCGGTAACTTCGTTTTGACCAAGCCAATGGTCTTGGGTC
ACGAATCCGCCGGTACTGTTGTCCAGGTTGGTAAGGGTGTCACCTCTCT
TAAGGTTGGTGACAACGTCGCTATCGAACCAGGTATTCCATCCAGATTC
TCCGACGAATACAAGAGCGGTCACTACAACTTGTGTCCTCACATGGCCT
TCGCCGCTACTCCTAACTCCAAGGAAGGCGAACCAAACCCACCAGGTAC
CTTATGTAAGTACTTCAAGTCGCCAGAAGACTTCTTGGTCAAGTTGCCA
GACCACGTCAGCTTGGAACTCGGTGCTCTTGTTGAGCCATTGTCTGTTG
GTGTCCACGCCTCTAAGTTGGGTTCCGTTGCTTTCGGCGACTACGTTGC
```

-continued

CGTCTTTGGTGCTGGTCCTGTTGGTCTTTTGGCTGCTGCTGTCGCCAAG
ACCTTCGGTGCTAAGGGTGTCATCGTCGTTGACATTTTCGACAACAAGT
TGAAGATGGCCAAGGACATTGGTGCTGCTACTCACACCTTCAACTCCAA
GACCGGTGGTTCTGAAGAATTGATCAAGGCTTTCGGTGGTAACGTGCCA
AACGTCGTTTTGGAATGTACTGGTGCTGAACCTTGTATCAAGTTGGGTG
TTGACGCCATTGCCCCAGGTGGTCGTTTCGTTCAAGTCGGTAACGCTGC
TGGTCCAGTCAGCTTCCCAATCACCGTTTTCGCCATGAAGGAATTGACT
TTGTTCGGTTCTTTCAGATACGGATTCAACGACTACAAGACTGCTGTTG
GAATCTTTGACACTAACTACCAAAACGGTAGAGAAAATGCTCCAATTGA
CTTTGAACAATTGATCACCCACAGATACAAGTTCAAGGACGCTATTGAA
GCCTACGACTTGGTCAGAGCCGGTAAGGGTGCTGTCAAGTGTCTCATTG
ACGGCCCTGAGTAATAA (SEQ ID NO: 7)

ATGACCGCTAATCCCTCTCTTGTTTTGAATAAGATTGACGACATTTCTT
TTGAAACTTACGATGCTCCCGAAATTAGCGAACCCACAGACGTTTTAGT
TCAAGTTAAAAAAACTGGTATCTGCGGTTCTGACATCCACTTCTACGCT
CATGGAAGGATCGGCAACTTCGTCTTAACAAAGCCAATGGTTCTGGGTC
ATGAAAGCGCGGGTACTGTTGTTCAAGTCGGTAAAGGTGTTACTTCACT
GAAGGTTGGTGATAACGTCGCAATCGAGCCCGGTATTCCATCTAGGTTC
AGTGATGAGTACAAATCTGGTCACTACAACCTGTGTCCACACATGGCAT
TTGCTGCTACTCCCAATTCTAAAGAGGGTGAACCAAACCCACCAGGAAC
TCTATGTAAGTACTTCAAATCTCCAGAAGACTTCCTGGTTAAGTTACCC
GATCATGTTTCTTTGGAGTTGGGTGCTTTGGTCGAGCCACTATCTGTTG
GGGTCCATGCTAGTAAATTAGGCTCCGTTGCATTTGGCGATTACGTTGC
TGTTTTTGGTGCTGGTCCAGTAGGATTACTGGCTGCCGCTGTCGCTAAG
ACATTTGGTGCCAAGGGTGTGATTGTCGTTGATATATTTGACAACAAGC
TGAAGATGGCCAAAGACATAGGTGCCGCTACACATACCTTCAACTCCAA
GACGGGAGGTAGTGAAGAATTGATCAAAGCCTTCGGTGGTAATGTACCA
AATGTTGTCTTGGAATGTACTGGGGCTGAACCATGTATTAAGCTAGGTG
TTGATGCCATCGCACCAGGTGGTAGATTCGTGCAAGTTGGTAATGCTGC
TGGTCCCGTGTCCTTTCCCATAACAGTGTTCGCTATGAAAGAACTTACT
TTGTTTGGTTCATTTCGTTATGGTTTCAACGACTATAAGACAGCCGTGG
GTATCTTTGATACTAACTACCAGAACGGTAGAGAGAATGCTCCCATTGA
CTTTGAACAGCTTATCACGCACAGATACAAATTCAAAGACGCCATTGAA
GCCTACGACCTAGTAAGAGCAGGTAAAGGGGCTGTCAAGTGTTTGATTG
ATGGTCCAGAATAATAA (SEQ ID NO: 8)

ATGACCGCTAACCCATCTTTGGTCTTGAACAAGATTGACGACATTTCTT
TCGAAACCTACGACGCTCCAGAAATTTCTGAACCAACCGACGTTTTGGT
TCAAGTCAAGAAGACCGGTATTTGTGGTTCTGACATTCACTTCTACGCT
CACGGTAGAATTGGTAACTTCGTCTTGACCAAGCCAATGGTCTTGGGTC
ACGAATCTGCTGGTACCGTTGTTCAAGTCGGTAAGGGTGTCACCTCTTT
GAAGGTCGGTGACAACGTCGCTATTGAACCAGGTATTCCAAGTAGATTC
TCTGACGAATACAAGTCTGGTCACTACAACTTGTGTCCACACATGGCTT
TCGCTGCTACCCCAAACTCTAAGGAAGGTGAACCAAACCCACCAGGTAC
CTTGTGTAAGTACTTCAAGTCTCCAGAAGACTTCTTGGTTAAGTTGCCA
GACCACGTTTCTTTGGAATTGGGTGCTTTGGTTGAACCATTGTCTGTTG
GTGTTCACGCTTCTAAGTTGGGTTCTGTTGCTTTCGGTGACTACGTTGC
TGTTTTCGGTGCTGGTCCAGTTGGTTTGTTGGCTGCTGCTGTTGCTAAG
ACCTTCGGTGCTAAGGGTGTCATTGTCGTTGACATTTTCGACAACAAGT
TGAAGATGGCTAAGGACATTGGTGCTGCTACCCACACCTTCAACTCTAA
GACCGGTGGTTCTGAAGAATTGATTAAGGCTTTCGGTGGTAACGTCCCA
AACGTCGTCTTGGAATGTACCGGTGCTGAACCATGTATTAAGTTGGGTG
TTGACGCTATTGCTCCAGGTGGTAGATTCGTCCAAGTTGGTAACGCTGC
TGGTCCAGTTTCTTTCCCAATTACCGTTTTCGCTATGAAGGAATTGACC
TTGTTCGGTTCTTTCAGATACGGTTTCAACGACTACAAGACCGCTGTTG
GTATTTTCGACACCAACTACCAAAACGGTAGAGAAAACGCTCCAATTGA
CTTCGAACAATTGATTACCCACAGATACAAGTTCAAGGACGCTATTGAA
GCTTACGACTTGGTTAGAGCTGGTAAGGGTGCTGTTAAGTGTTTGATTG
ACGGTCCAGAATAATAA (SEQ ID NO: 9)

ATGTTGTGTTCAGTAATTCAGAGACAGACAAGAGAGGTTTCCAACACAA
TGTCTTTAGACTCATACTATCTTGGGTTTGATCTTTCGACCCAACAACT
GAAATGTCTCGCCATTAACCAGGACCTAAAAATTGTCCATTCAGAAACA
GTGGAATTTGAAAAGGATCTTCCGCATTATCACACAAAGAAGGGTGTCT
ATATACACGGCGACACTATCGAATGTCCCGTAGCCATGTGGTTAGAGGC
TCTAGATCTGGTTCTCTCGAAATATCGCGAGGCTAAATTTCCATTGAAC
AAAGTTATGGCCGTCTCAGGGTCCTGCCAGCAGCACGGGTCTGTCTACT
GGTCCTCCCAAGCCGAATCTCTGTTAGAGCAATTGAATAAGAAACCGGA
AAAAGATTTATTGCACTACGTGAGCTCTGTAGCATTTGCAAGGCAAACC
GCCCCCAATTGGCAAGACCACAGTACTGCAAAGCAATGTCAAGAGTTTG
AAGAGTGCATAGGTGGGCCTGAAAAAATGGCTCAATTAACAGGGTCCAG
AGCCCATTTTAGATTTACTGGTCCTCAAATTCTGAAAATTGCACAATTA
GAACCAGAAGCTTACGAAAAAACAAAGACCATTTCTTTAGTGTCTAATT
TTTTGACTTCTATCTTAGTGGGCCATCTTGTTGAATTAGAGGAGGCAGA
TGCCTGTGGTATGAACCTTTATGATATACGTGAAAGAAAATTCAGTGAT
GAGCTACTACATCTAATTGATAGTTCTTCTAAGGATAAAACTATCAGAC
AAAAATTAATGAGAGCACCCATGAAAAATTTGATAGCGGGTACCATCTG

-continued

TAAATATTTTATTGAGAAGTACGGTTTCAATACAAACTGCAAGGTCTCT
CCCATGACTGGGGATAATTTAGCCACTATATGTTCTTTACCCCTGCGGA
AGAATGACGTTCTCGTTTCCCTAGGAACAAGTACTACAGTTCTTCTGGT
CACCGATAAGTATCACCCCTCTCCGAACTATCATCTTTTCATTCATCCA
ACTCTGCCAAACCATTATATGGGTATGATTTGTTATTGTAATGGTTCTT
TGGCAAGGGAGAGGATAAGAGACGAGTTAAACAAAGAACGGGAAAATAA
TTATGAGAAGACTAACGATTGGACTCTTTTTAATCAAGCTGTGCTAGAT
GACTCAGAAAGTAGTGAAAATGAATTAGGTGTATATTTTCCTCTGGGGG
AGATCGTTCCTAGCGTAAAAGCCATAAACAAAAGGGTTATCTTCAATCC
AAAAACGGGTATGATTGAAAGAGAGGTGGCCAAGTTCAAAGACAAGAGG
CACGATGCCAAAAATATTGTAGAATCACAGGCTTTAAGTTGCAGGGTAA
GAATATCTCCCCTGCTTTCGGATTCAAACGCAAGCTCACAACAGAGACT
GAACGAAGATACAATCGTGAAGTTTGATTACGATGAATCTCCGCTGCGG
GACTACCTAAATAAAAGGCCAGAAAGGACTTTTTTTGTAGGTGGGGCTT
CTAAAAACGATGCTATTGTGAAGAAGTTTGCTCAAGTCATTGGTGCTAC
AAAGGGTAATTTTAGGCTAGAAACACCAAACTCATGTGCCCTTGGTGGT
TGTTATAAGGCCATGTGGTCATTGTTATATGACTCTAATAAAATTGCAG
TTCCTTTTGATAAATTTCTGAATGACAATTTTCCATGGCATGTAATGGA
AAGCATATCCGATGTGGATAATGAAAATTGGGATCGCTATAATTCCAAG
ATTGTCCCCTTAAGCGAACTGGAAAAGACTCTCATCTAA (SEQ ID NO: 10)

MLCSVIQRQTREVSNTMSLDSYYLGFDLSTQQLKCLAINQDLKIVHSET
VEFEKDLPHYHTKKGVYIHGDTIECPVAMWLEALDLVLSKYREAKFPLN
KVMAVSGSCQQHGSVYWSSQAESLLEQLNKKPEKDLLHYVSSVAFARQT
APNWQDHSTAKQCQEFEECIGGPEKMAQLTGSRAHFRFTGPQILKIAQL
EPEAYEKTKTISLVSNFLTSILVGHLVELEEADACGMNLYDIRERKFSD
ELLHLIDSSSKDKTIRQKLMRAPMKNLIAGTICKYFIEKYGFNTNCKVS
PMTGDNLATICSLPLRKNDVLVSLGTSTTVLLVTDKYHPSPNYHLFIHP
TLPNHYMGMICYCNGSLARERIRDELNKERENNYEKTNDWTLFNQAVLD
DSESSENELGVYFPLGEIVPSVKAINKRVIFNPKTGMIEREVAKFKDKR
HDAKNIVESQALSCRVRISPLLSDSNASSQQRLNEDTIVKFDYDESPLR
DYLNKRPERTFFVGGASKNDAIVKKFAQVIGATKGNFRLETPNSCALGG
CYKAMWSLLYDSNKIAVPFDKFLNDNFPWHVMESISDVDNENWDRYNSK
IVPLSELEKTLI (SEQ ID NO: 11)

ATGCTGTGCTCCGTTATACAAAGGCAAACAAGAGAAGTATCCAACACTA
TGTCTTTAGATAGTTATTATCTAGGATTCGATTTAAGTACACAACAATT
GAAATGTCTTGCTATAAACCAGGATCTAAAGATCGTCCATTCCGAAACT
GTCGAGTTCGAGAAGGACTTACCACATTATCACACCAAGAAAGGCGTCT
ACATTCATGGTGACACCATCGAATGCCCAGTTGCTATGTGGTTAGAAGC
CCTGGATCTTGTCCTGTCCAAATATAGGGAGGCAAAGTTCCCACTGAAC
AAGGTCATGGCTGTTTCCGGTTCTTGTCAGCAGCATGGCTCCGTCTACT
GGTCATCACAGGCTGAATCTCTGTTAGAACAACTGAACAAGAAGCCAGA
GAAGGACCTGTTACACTACGTCTCCTCTGTTGCATTTGCCAGACAAACT
GCTCCTAATTGGCAAGACCATTCCACTGCTAAACAATGTCAGGAGTTCG
AAGAGTGTATTGGTGGACCAGAGAAAATGGCCCAGTTAACTGGTTCCCG
TGCTCATTTCAGGTTCACAGGCCCACAAATCCTGAAGATTGCTCAGTTA
GAACCAGAGGCTTATGAAAAGACTAAGACCATCTCTTTGGTCTCTAATT
TCTTAACTTCCATTCTGGTTGGTCACTTGGTCGAACTGGAAGAAGCTGA
TGCGTGTGGTATGAACCTGTACGACATCCGTGAGAGGAAGTTCTCTGAC
GAACTGCTGCATCTTATCGACTCCTCCTCTAAGGACAAGACCATCAGGC
AGAAACTGATGAGGGCACCAATGAAGAACCTGATTGCCGGTACTATTTG
CAAGTACTTCATCGAAAAGTATGGCTTCAACACCAACTGCAAAGTCTCC
CCTATGACTGGCGATAACCTAGCCACCATTTGTAGCTTGCCCTTAAGAA
AAAACGATGTTCTTGTGTCTTTGGGTACTTCCACAACCGTCTTGTTGGT
TACCGACAAATATCACCCTTCACCAAACTACCACCTGTTCATCCACCCG
ACGTTGCCTAACCACTACATGGGCATGATCTGCTACTGCAATGGCAGTT
TAGCAAGGGAAAGGATAAGGGACGAGTTGAACAAGGAGAGGGAGAACAA
CTACGAGAAGACCAACGATTGGACCCTGTTCAACCAAGCTGTCCTGGAT
GATAGCGAATCCTCCGAGAATGAACTGGGCGTTTACTTTCCACTAGGCG
AGATCGTTCCATCTGTCAAGGCCATCAACAAGAGAGTAATCTTCAACCC
CAAGACTGGCATGATCGAAAGGGAAGTCGCCAAGTTCAAGGACAAGAGA
CATGACGCCAAGAACATCGTTGAATCTCAAGCCTTATCTTGCCGTGTTA
GGATTTCTCCCCTACTAAGCGACTCCAATGCTTCTTCCCAGCAACGTTT
GAACGAGGATACGATTGTTAAATTCGACTACGACGAGAGTCCATTGAGA
GACTACTTGAACAAACGTCCTGAGAGGACATTCTTTGTTGGTGGCGCAT
CCAAGAACGATGCTATTGTTAAGAAGTTTGCTCAGGTCATAGGAGCAAC
CAAAGGTAACTTTCGTTTAGAAACTCCAAACTCATGCGCTTTAGGTGGT
TGCTACAAGGCTATGTGGTCTTTGTTGTATGATAGCAATAAAATCGCTG
TTCCTTTCGACAAGTTCCTAAACGATAACTTCCCTTGGCACGTCATGGA
ATCCATCAGCGATGTAGACAACGAGAATTGGGATAGATACAATTCTAAA
ATAGTTCCCTTGTCTGAGTTAGAGAAGACCTTGATTTAATAA (SEQ ID NO: 12)

ATGTTGTGTTCTGTCATTCAAAGACAAACCAGAGAAGTTTCTAACACCA
TGTCTTTGGACTCTTACTACTTGGGTTTCGACTTGTCTACCCAACAATT
GAAGTGTTTGGCTATTAACCAAGACTTGAAGATTGTCCACTCTGAAACC
GTTGAGTTCGAAAAGGACTTGCCACACTACCACACCAAGAAGGGTGTCT
ACATTCACGGTGACACCATTGAATGTCCAGTCGCTATGTTGGAAGCTTT

-continued

```
GGACTTGGTTTTGTCTAAGTACAGAGAAGCTAAGTTCCCATTGAACAAG
GTCATGGCTGTCTCTGGTTCTTGTCAACAACACGGTTCTGTCTACTCTT
CTCAAGCTGAATCTTTGTTGGAACAATTGAACAAGAAGCCAGAAAAGGA
CTTGTTGCACTACGTCTCTTCTGTCGCTTTCGCTAGACAAACCGCTCCA
AACCAAGACCACTCTACCGCTAAGCAATGTCAAGAGTTCGAAGAATGTA
TTGGTGGTCCAGAAAAGATGGCTCAATTGACCGGTAGTAGAGCACACTT
CAGATTCACCGGTCCACAAATTTTGAAGATTGCTCAATTGGAACCAGAA
GCTTACGAAAAGACCAAGACCATTTCTTTGGTCTCTAACTTCTTGACCT
CTATTTTGGTCGGTCACTTGGTCGAATTGGAAGAAGCTGACGCTTGTGG
TATGAACTTGTACGACATTAGAGAAAGAAAGTTCTCTGACGAATTGTTG
CACTTGATTGACTCTTCTTCTAAGGACAAGACCATTAGACAAAAGTTGA
TGAGGGCTCCAATGAAGAACTTGATTGCTGGTACCATTTGTAAGTACTT
CATTGAAAAGTACGGTTTCAACACCAACTGTAAGGTCTCTCCAATGACC
GGTGACAACTTGGCTACCATTTGTTCTTTGCCATTGAGAAAGAACGACG
TTTTGGTTTCTTTGGGTACCTCTACCACCGTCTTGTTGGTTACCGACAA
GTACCACCCATCTCCAAACTACCACTTGTTCATTCACCCAACCTTGCCA
AACCACTACATGGGTATGATTTGTTACTGTAACGGTTCTTTGGCTAGAG
AAAGAATTAGAGACGAATTGAACAAGGAAAGAGAAAACAACTACGAAAA
GACCAACGACACCTTGTTCAACCAAGCTGTTTTGGACGACTCTGAATCT
TCTGAAAACGAATTGGGTGTCTACTTCCCATTGGGTGAAATTGTTCCAT
CTGTCAAGGCTATTAACAAGAGAGTCATTTTCAACCCAAAGACCGGTAT
GATTGAAAGAGAAGTCGCTAAGTTCAAGGACAAGAGACACGACGCTAAG
AACATTGTCGAATCTCAAGCTTTGTCTTGTAGAGTTAGAATTTCTCCAT
TGTTGTCTGACTCTAACGCTTCTTCTCAACAAAGATTGAACGAAGACAC
CATTGTCAAGTTCGACTACGACGAATCTCCATTGAGAGACTACTTGAAC
AAGAGACCAGAAAGAACCTTCTTCGTTGGTGGTGCTTCTAAGAACGACG
CTATTGTTAAGAAGTTCGCTCAAGTCATTGGTGCTACCAAGGGTAACTT
CAGATTGGAAACCCCAAACTCTTGTGCTTTGGGTGGTTGTTACAAGGCT
ATGTCTTTGTTGTACGACTCTAACAAGATTGCTGTTCCATTCGACAAGT
TCTTGAACGACAACTTCCCACACGTCATGGAATCTATTTCTGACGTTGA
CAACGAAAACGACAGATACAACTCTAAGATTGTTCCATTGTCTGAATTG
GAAAAGACCTTGATTTAATAA
```

Example 1

Construction of Plasmid PLS2802 with XR, XD and XK Genes

Xylose reductase from *Pichis stipitis* (XR.2; SEQ ID NO:3), xylitol dehydrogenase from *Pichia stipitis* (XD.2; SEQ ID NO:7), and xylulose kinase (XK.2; SEQ ID NO:11) from *Saccharomyces cerevisiae* were synthesized with codon optimization for expression in yeast. The genes were synthesized with the following 5' and 3' flanks to introduce specific restriction enzyme sites:

```
                                        (SEQ ID NO: 13)
XR        5' GGATCCCAAACAAA;
and
                                        (SEQ ID NO: 14)
          3' CATATG
to introduce 5'-BamHI and 3'-NdeI;

                                        (SEQ ID NO: 15)
XD        5' ACTAGTCAAACAAA;
and
                                        (SEQ ID NO: 16)
          3'-GACGTC
to introduce 5'SpeI and 3' AatII;
and

                                        (SEQ ID NO: 17)
XK        5' GCGGCCGCCAAACAAA;
and
                                        (SEQ ID NO: 18)
          3' CTCGAG
to introduce 5' NotI and 3' XhoI
```

The yeast vector p427TEF (Dualsystems Biotech AG) was used for gene expression. The vector contains a kanamycin resistance gene that allows for selection in yeast, an ampicillin resistance gene that allows for selection in *E. coli*, and a 2 micron origin of replication that allows for propagation of plasmids in high copy numbers in yeast. For cloning the pathway genes, p427TEF was digested with SacI and XhoI restriction enzymes. The larger fragment (6235 bp) was ligated with an oligomer of the following sequence, 5'GAGCTCACGGATCCGTCATATGCTAGATCTCTGAATTCTTACTAGTTCGACGTCTACCTAGGCAGTCGACACGCGGCCGCTTCTCGAG 3' (SEQ ID NO:19) to introduce a new multiple cloning site (MCS) with desired restriction sites. Using the new MCS, the TEF1 promoter of *S. cerevisiae* was re-introduced in the vector using SacI/BamHI restriction sites to create PLS1567. To clone all 3 genes into one vector, additional promoters (Adh1p, GPDp) and terminators (Adh2t, Adh1t) were cloned into PLS1567 using yeast recombinational cloning using methods commonly used in the art. The promoters and terminators were each amplified using the primer sets shown in Table 1-1.

TABLE 1-1

Primers Used to Amplify Yeast Promoters and Terminators for PLS1448 Construction

| Cassette | Primer 1 | Primer 2 |
|---|---|---|
| ADH2 terminator | GCA TAG CAA TCT AAT CTA AGT TTT GGA TCC GTC ATA TGG CGG ATC TCT TAT GTC TTT ACG (SEQ ID NO: 20) | TTG TAT GTA CCT GTC TGA ATT CAG AGA TCT AGC CCT GAG AAA CTA TAT GAG GGT (SEQ ID NO: 21) |
| ADH1 promoter | ACC CTC ATA TAG TTT CTC AGG GCT AGA TCT CTG AAT TCA GAC AGG TAC ATA CAA (SEQ ID NO: 22) | TCA TAA ATC ATA AGA AAT TCG CGA CGTCGA ACT AGT TGT ATA TGA GAT AGT TGA TTG TAT GC (SEQ ID NO: 23) |
| ADH1 terminator | GCA TAC AAT CAA CTA TCT CAT ATA CAA CTA GTT CGA CGT CGC GAA TTT CTT ATG ATT TAT GA (SEQ ID NO: 24) | TGA TAA ACT CGA AGT CGA CTG CCT AGG CAT GCC GGT AGA GGT GTG GT (SEQ ID NO: 25) |
| GPD promoter | ACC ACA CCT CTA CCG GCA TGC CTA GGC AGT CGA CTT CGA GTT TAT CA (SEQ ID NO: 26) | GCG TGA CAT AAC TAA TTA CAT GAC TCG AGA AGC GGC CGC TTT GTT TGT TTA TGT GTGT (SEQ ID NO: 27) |

SOE-PCR was used to combine the ADH2 terminator with the ADH1 promoter, and the ADH1 terminator with the GPD1 promoter. An internal AatII site in the ADH2 terminator was removed by changing its sequence from GACGTC (SEQ ID NO:28) to GATGTC (SEQ ID NO:29). For yeast recombinational cloning, PLS1567 was digested with BamHI/XhoI, and a 3:1 mass ratio of each insert to digested PLS1567 was used. The transformants were selected on culture plates containing G418. The resulting plasmid (PLS1448) with the 3 promoters and terminators was confirmed by sequencing. The 2 micron origin in PLS1448 was replaced with the CEN6/ARS4 origin of replication to yield PLS1565 with lower copy number and greater stability.

XR.2, XD.2 and XK.2 genes were then cloned into PLS1565 using yeast recombinational cloning. To amplify all the pieces, the primer sets provided in Table 1-2 were used.

TABLE 1-2

Primers Used to Amplify Cassettes for PLS2802 Construction

| Cassette | Primer 1 | Primer 2 |
|---|---|---|
| PS.XR.2 | CTT GCT CAT TAG AAA GAA AGC ATA GCA ATC TAA TCT AAG TTT TGG ATC CCA AAC AAA ATG CCC TCC A (SEQ ID NO: 30) | CTA TAA ATC GTA AAG ACA TAA GAG ATC CGC CAT ATG TTA TTA AAC GAA GAT TGG TAT CTT G (SEQ ID NO: 31) |
| ADH2t-ADH 1p | CAA GAT ACC AAT CTT CGT TTA ATA ACA TAT GGC GGA TCT CTT ATG TCT TTA CGA TTT ATA G (SEQ ID NO: 32) | GAG GGA TTA GCG GTC ATT TTG TTT GAC TAG TTG TAT ATG AGA TAG TTG ATT GTA TGC TTG GTA (SEQ ID NO: 33) |
| PS.XD.2 | TAC CAA GCA TAC AAT CAA CTA TCT CAT ATA CAA CTA GTC AAA CAA AAT GAC CGC TAA TCC CTC (SEQ ID NO: 34) | TAA TAA AAA TCA TAA ATC ATA AGA AAT TCG CGA CGT CTT ATT ATT CTG GAC CAT CAA TCA (SEQ ID NO: 35) |
| ADH1t-GPDp | TGA TTG ATG GTC CAG AAT AAT AAG ACG TCG CGA ATT TCT TAT GAT TTA TGA TTT TTA TTA (SEQ ID NO: 36) | TTT GTA TAA CGG AGC ACA GCA TTT TGT TTG GCG GCC GCT TTG TTT GTT TAT GTG TGT TTA T (SEQ ID NO: 37) |
| SC.XK.2 | ATA AAC ACA CAT AAA CAA ACA AAG CGG CCG CCA AAC AAA ATG CTG TGC TCC GTT ATA CAA A (SEQ ID NO: 38) | GGG GAG GGC GTG AAT GTA AGC GTG ACA TAA CTA ATT ACA TGA CTC GAG TTA TTA AAT CAA GGT CTT CTC T (SEQ ID NO: 39) |

Figure 3:
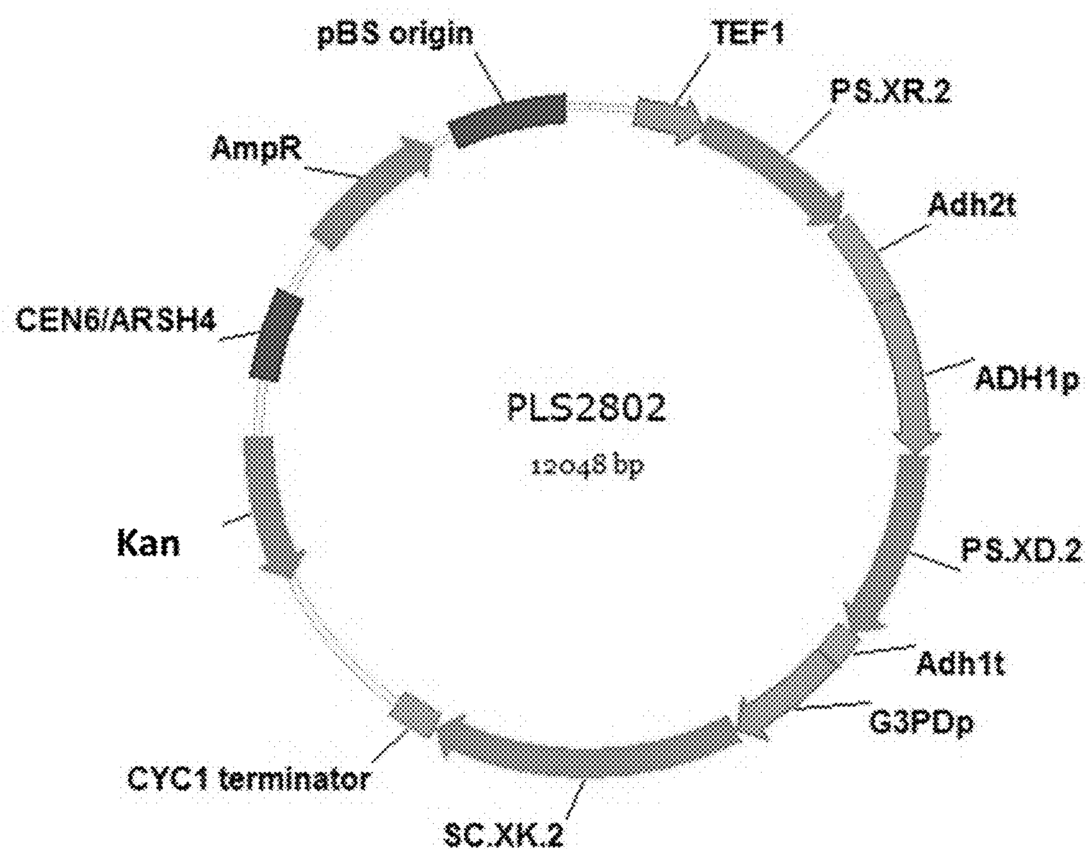
FIG. 3 provides a map of plasmid PLS2802, comprising XR.2, XD.2, and XK.2 genes.

For yeast recombinational cloning, PLS1565 was digested with BamHI/XhoI and gel purified. Then, a 3:1 mass ratio of each insert:digested PLS1565 was used. Transformants were selected using G418 and confirmed by sequencing. The resulting plasmid (PLS2802) with the 3 genes cloned is depicted in FIG. 3.

Example 2

Transformation of PLS2802 into Yeast and Fermentation

PLS2802 was used to transform *S. cerevisiae* (THERMOSACC®; LYCC6825; Lallemand). Transformants were selected on YPD agar plates with 200 ug/ml G418 at 30° C. for 48 hrs. Single colonies were used to inoculate 250 μl of defined media (60 g/L glucose; 3 g/L potassium phosphate, 5 g/L ammonium sulphate, 0.5 g/L magnesium sulphate, 100 mM MES pH 5.5) in Axygen 96-well plates. The cultures were grown at 30° C. for 72 hrs with 85% relative humidity. Then, 40 μl of the culture was used to inoculate 360 μl of 3:1 mixture of defined media (60 g/L glucose; 3 g/L potassium phosphate, 5 g/L ammonium sulphate, 0.5 g/L magnesium sulphate, 100 mM MES pH 5.5) to plant (wheat straw) biomass hydrolysates containing xylose in 96-well Costar deep well plates for propagating the cells. The cultures were grown at 30° C. for 40 hrs with 250 rpm shaking. At 40 hrs, the cells were spun down at 22° C. for 10 mins and evaluated for xylose fermentation activity.

For fermentation, cells were re-suspended in 400 ul of plant (wheat straw) biomass hydrolysates containing xylose and the plates were sealed with mats. Plates were incubated at 30° C., with 100 rpm shaking. At different timepoints, cells were harvested and the residual sugars and ethanol in the supernatant were measured by a standard HPLC based method known in the art (See e.g., DuPont et al., Carb. Polym., 68:1-16 [2007], which is incorporated herein by reference). In some experiments, the residual xylose in the supernatant was measured using a spectrophotometric assay (e.g., Megazyme xylose assay; Cat no. K-XYLOSE) performed according to the manufacture's protocol. Strains transformed with the empty vector were used as a control. Strains transformed with the xylose pathway consumed significantly higher amounts of xylose at each of the timepoints tested compared to the vector control.

Example 3

Effect of Codon Optimization on XR, XD Activity

To evaluate the effect of codon optimization, alternate sequences of XR and XD genes were tested. Each of the genes were synthesized with either their native *Pichia stiptis* sequence (XR.1, XD.1) or with codon optimization towards highly expressed yeast sequences (XR.3; XD.3) (Brat et al Appl. Environ. Microbiol., 75:2304-2311 [2009]). To evaluate the effect of the optimization, XR and XD genes were cloned into vector PLS1448 with different combinations (XR.1-XD.1-XK.2; XR.2-XD.1-XK.2; XR.3-XD.1-XK.2; XR.1-XD.2-XK.2; XR.1-XD.3-XK.2). The variants were used to transform *S. cerevisiae* (THERMOSACC®; LYCC6469; Lallemand). Transformants were selected on YPD agar plates containing 200 ug/ml G418 at 30° C. for 48 hrs. Single colonies were used to inoculate 250 µl of YPD in Axygen 96-well plates. The cultures were grown at 30° C. for 72 hrs with 85% relative humidity. Then, 40 µl of the culture was used to inoculate 360 µl of YPD with 20 g/L xylose in 96 well Costar deep well plates for propagating the cells. The cultures were grown at 30° C. for 40 hrs with 250 rpm shaking. At 40 hrs, the cells were spun down at 22° C. for 10 mins and evaluated for xylose fermentation activity.

For fermentation, cells were re-suspended in 400 ul of YPD with 20 g/L xylose and the plates were sealed with mats. Plates were incubated at 30° C. at 100 rpm shaking. At 48 hrs, cells were harvested and the residual xylose in the supernatant was measured by a spectrophotometric assay as described above. The best xylose consumption was seen with XR.1-XD.2-XK.2 (PLS6058) variant (See, Table 3-1).

TABLE 3-1

Xylose Consumption by Yeast Strain Transformed With Xylose Pathway

| Strain | Xylose Consumed (g/L) |
|---|---|
| THERMOSACC ® + PLS1448 (vector control) | 2.5 |
| THERMOSACC ® + XR.2-XD.2-XK.2 | 12.5 |
| THERMOSACC ® + XR.1-XD.2-XK.2 | 15.8 |
| THERMOSACC ® + XR.3-XD.2-XK.2 | 2.5 |
| THERMOSACC ® + XR.2-XD.1-XK.2 | 13.8 |
| THERMOSACC ® + XR.2-XD.3-XK.2 | 13.5 |

Example 4

Construction of XR and XD Variant Libraries

*Pichia stipitis* xylose reductase and xylitol dehydrogenase were subjected to directed evolution algorithms to improve xylose utilization activity using methods as known in the art (See e.g., WO 2010/144103). Purified PCR products encoding XR and/or XD variants (i.e., comprising amino acid substitutions) and the vector portion of plasmid PLS2802 were pooled and used to transform *S. cerevisiae* (THERMOSACC®; LYCC6825; Lallemand) to produce a library via homologous recombination (See e.g., Oldenburg et al., Nucl. Acids Res., 25(2):451-452 [1997], which is incorporated herein by reference). The library was screened for xylose fermentation activity as described in Example 2. The xylose utilization was measured relative to the positive control (XR.1-XD.2-XK.2). Strains that had activity significantly above the positive control were retested in replicate and the variants sequenced to identify mutations. The results are provided in the following Tables.

TABLE 4-1

XR and XD Variants Exhibiting Improved Activity

| | XR | | XD | | Xylose utilization Activity compared |
|---|---|---|---|---|---|
| Variant No: | Active Mutations wrt XR WT | Silent Mutations wrt XR WT | Active Mutations wrt XD WT | Silent Mutations wrt XD WT | to WT *P. stipitis* XR/XD |
| 1 (WT & Positive Control) | | | | | 1.0 |
| 2 | R276F | t811a/c812g/c816t | I208R | | ≥1.0 |
| 3 | R276F | t811a/c812g/c816t | F209S/N211K | | ≥1.0 |
| 4 | S271G | c816t/a826c/a828t | I208R/N211K | | ≥1.0 |
| 5 | S271G | c816t/a826c/a828t | I208R/N211S | | ≥1.0 |
| 6 | R276F | t811a/c812g/c816t | I208R/F209S/N211S | | ≥1.0 |
| 7 | S271G | c816t/a826c/a828t; | I208R | | ≥1.0 |
| 8 | K270R | t811a/c812g/c816t/ a826c/a828t | I208R/N211R | | ≥1.0 |
| 9 | K270R | t811a/c812g/c816t/ a826c/a828t | F209S/N211K | | ≥1.0 |
| 10 | N272P/R276F | t811a/c812g | F209S/N211K | | ≥1.0 |
| 11 | K270R/N272P/R276F | t811a/c812g | N211K | | ≥1.0 |
| 12 | | t811a/c812g/c816t/ a826c/a828t | I208R | | ≥1.0 |

TABLE 4-2

XR Variants with Improved Activity

| Variant No: | XR-Active Mutations wrt XR WT | XR-Silent Mutations wrt XR WT | Xylose Utilization Activity Compared to WT *P. stipitis* XR/XD |
|---|---|---|---|
| 1 (WT and Positive Control) | | | 1.00 |
| 13 | R276W | | ≥1.5 |
| 14 | A266V | | ≥1.4 |
| 15 | T232V | | ≥1.4 |
| 16 | I267V | | ≥1.4 |
| 17 | V255I | | ≥1.4 |
| 18 | P2T/A266C | | ≥1.4 |
| 19 | S233V | | ≥1.4 |
| 20 | K152E | | ≥1.3 |
| 21 | L224S | | ≥1.3 |
| 22 | A246L | | ≥1.3 |
| 23 | | a280c/a282t | ≥1.3 |
| 24 | K132N | | ≥1.3 |
| 25 | R276M | | ≥1.3 |
| 26 | K132A | | ≥1.3 |
| 27 | N302S | | ≥1.3 |

TABLE 4-2-continued

| XR Variants with Improved Activity | | | |
|---|---|---|---|
| Variant No: | XR-Active Mutations wrt XR WT | XR-Silent Mutations wrt XR WT | Xylose Utilization Activity Compared to WT *P. stipitis* XR/XD |
| 28 | R206S | | ≥1.3 |
| 29 | A246S | | ≥1.3 |
| 30 | A49G | | ≥1.3 |
| 31 | S261N | | ≥1.2 |
| 32 | K36Q | | ≥1.2 |
| 33 | T232A | | ≥1.2 |
| 34 | K155R | | ≥1.2 |
| 35 | | c438t | ≥1.2 |
| 36 | L224A | | ≥1.2 |
| 37 | S261A | | ≥1.2 |
| 38 | K152H | | ≥1.2 |
| 39 | D134E | | ≥1.2 |
| 40 | | c906t | ≥1.2 |
| 41 | I62V | | ≥1.2 |
| 42 | V283H | | ≥1.2 |
| 43 | L108Y | | ≥1.2 |
| 44 | | c201t | ≥1.2 |
| 45 | D11K | | ≥1.2 |
| 46 | S233C | | ≥1.2 |
| 47 | D134V | | ≥1.2 |
| 48 | S285E | | ≥1.2 |
| 49 | A245S | | ≥1.2 |
| 50 | S233I | | ≥1.2 |
| 51 | S3R | | ≥1.2 |
| 52 | I162L | | ≥1.2 |
| 53 | | c306t | ≥1.2 |
| 54 | G157R | | ≥1.2 |
| 55 | T114S | | ≥1.2 |
| 56 | L224V | | ≥1.2 |
| 57 | | t511c/g513t | ≥1.2 |
| 58 | R33L | | ≥1.2 |
| 59 | V24G | | ≥1.2 |
| 60 | S233K | | ≥1.2 |
| 61 | | t358c/a360g | ≥1.2 |
| 62 | | t82a/c83g | ≥1.2 |
| 63 | K68G | | ≥1.2 |
| 64 | N302D | | ≥1.2 |
| 65 | D282G | | ≥1.1 |
| 66 | R206V | | ≥1.1 |
| 67 | | a426t | ≥1.1 |
| 68 | G249D | | ≥1.1 |
| 69 | | t511c/g513t | ≥1.1 |
| 70 | V318C | | ≥1.1 |
| 71 | L303V | | ≥1.1 |
| 72 | P252C | | ≥1.1 |
| 73 | E89V | | ≥1.1 |
| 74 | | a478c/g480t | ≥1.1 |
| 75 | | t703c | ≥1.1 |
| 76 | | a378t | ≥1.1 |
| 77 | S97T | | ≥1.1 |
| 78 | K155Y | c855t | ≥1.1 |
| 79 | N231L | | ≥1.1 |
| 80 | N225K | | ≥1.1 |
| 81 | N225S | | ≥1.1 |
| 82 | S3H | | ≥1.1 |
| 83 | A56E | | ≥1.1 |
| 84 | | c201t | ≥1.1 |
| 85 | K152A | | ≥1.1 |
| 86 | P168S | | ≥1.1 |
| 87 | D134H | | ≥1.1 |
| 88 | N225D | | ≥1.1 |
| 89 | Q226D | | ≥1.1 |
| 90 | S233G | | ≥1.1 |
| 91 | D282C | | ≥1.1 |
| 92 | E89N | | ≥1.1 |
| 93 | | t670c/g672t | ≥1.1 |
| 94 | K281L | | ≥1.1 |
| 95 | N302G | | ≥1.1 |
| 96 | A297H | | ≥1.1 |
| 97 | Q226E | | ≥1.1 |
| 98 | S233F | | ≥1.1 |
| 99 | K123C | | ≥1.1 |
| 100 | S261T | | ≥1.1 |

TABLE 4-2-continued

| XR Variants with Improved Activity | | | |
|---|---|---|---|
| Variant No: | XR-Active Mutations wrt XR WT | XR-Silent Mutations wrt XR WT | Xylose Utilization Activity Compared to WT *P. stipitis* XR/XD |
| 101 | K152Q | | ≥1.1 |
| 102 | R33V | | ≥1.1 |
| 103 | A14V | | ≥1.1 |
| 104 | S97R | | ≥1.1 |
| 105 | | a585g | ≥1.1 |
| 106 | K155D | | ≥1.1 |
| 107 | Q226S | | ≥1.1 |
| 108 | Q219T | | ≥1.1 |
| 109 | I143L | | ≥1.1 |
| 110 | D102T; | | ≥1.1 |
| 111 | N231H; | | ≥1.1 |
| 112 | T232S | | ≥1.0 |
| 113 | N225E | | ≥1.0 |
| 114 | S184A | | ≥1.0 |
| 115 | S3W | | ≥1.0 |
| 116 | D282R | | ≥1.0 |
| 117 | Q219L | | ≥1.0 |
| 118 | T232C | | ≥1.0 |
| 119 | R228T | | ≥1.0 |
| 120 | K281V | | ≥1.0 |
| 121 | S285T | | ≥1.0 |
| 122 | | t688c | ≥1.0 |
| 123 | N231S | | ≥1.0 |
| 124 | | c849g | ≥1.0 |
| 125 | K155I | | ≥1.0 |
| 126 | N231G | | ≥1.0 |
| 127 | K242L | | ≥1.0 |
| 128 | | t354g | ≥1.0 |
| 129 | A297S | | ≥1.0 |
| 130 | K68M | | ≥1.0 |
| 131 | | c408t | ≥1.0 |
| 132 | | t766c | ≥1.0 |
| 133 | T240V | | ≥1.0 |
| 134 | E46K/ D47N | | ≥1.0 |
| 135 | I301Y | | ≥1.0 |
| 136 | I301C | | ≥1.0 |
| 137 | Q226V | | ≥1.0 |
| 138 | L303I | | ≥1.0 |
| 139 | E279Q | | ≥1.0 |
| 140 | P275A | | ≥1.0 |
| 141 | D23E/K68R | | ≥1.0 |
| 142 | F236L | | ≥1.0 |
| 143 | Q219H | | ≥1.0 |
| 144 | N225Y | | ≥1.0 |
| 145 | N7L | | ≥1.0 |
| 146 | A56Y | | ≥1.0 |
| 147 | F17W | | ≥1.0 |
| 148 | K155A | | ≥1.0 |
| 149 | K116Q | | ≥1.0 |
| 150 | S261C | | ≥1.0 |

TABLE 4-3

Additional XR Variants with Improved Activity

| Variant No. | XR-Active Mutations wrt XR WT | XR-Silent Mutations wrt XR WT | Xylose Utilization Activity (Compared to Positive Control) |
|---|---|---|---|
| 13 (Positive Control) | R276W | | 1.00 |
| 151 | P2T/R206S/R276W | | ≥1.4 |
| 152 | P2T/A49G/R276W | | ≥1.4 |
| 153 | P2T/A49G/R206S/R276W | | ≥1.4 |
| 154 | P2T/R276W | | ≥1.3 |
| 155 | A49G/R276W | | ≥1.3 |
| 156 | P2T/K132N/K152E/R276W | | ≥1.3 |
| 157 | P2T/A49G/R276W | a280c | ≥1.2 |
| 158 | G227D/R276W | t6g | ≥1.2 |
| 159 | A49G/K132A/R206S/R276W | | ≥1.2 |
| 160 | P2T/P168S/R276W | a853t/g854c/c954g | ≥1.2 |
| 161 | A49G; K152E; R276W | a280c | ≥1.2 |
| 162 | R276W | c54t | ≥1.2 |
| 163 | P2T/A49G/R276W/V318C | a853t/g854c | ≥1.2 |
| 164 | P2T/A49G/K132N/R276W | | ≥1.2 |
| 165 | P2T/K132N/R276W | a280c | ≥1.2 |
| 166 | P2T/K132N/R276W | | ≥1.2 |
| 167 | P2T/G157R/R276W | g324a/c402t/a853t/g854c/c954g | ≥1.2 |
| 168 | R33L/A56E/R276W | t7a/c8g/g456a | ≥1.1 |
| 169 | A49G/R276W | t753c | ≥1.1 |
| 170 | S3H/R33L/A56E/R276W | | ≥1.1 |
| 171 | A49G/R276W | a280c | ≥1.1 |
| 172 | R276W | t82a/c83g/c201t | ≥1.1 |
| 173 | P2T/R276W | c954g | ≥1.1 |
| 174 | S3H/T114S/R276W/N302S | t699c/a756c | ≥1.1 |
| 175 | P2T/R276W | t552c | ≥1.1 |
| 176 | A49G/K132N/R206S/S233V/R276M/N302S | | ≥1.1 |
| 177 | A49G/K132A/R276W | a280c | ≥1.1 |
| 178 | R276W/V318C | t6g/t781a/c782g/a853t/g854c | ≥1.1 |
| 179 | P2T/A246L/R276W | t781a/c782g/c954g | ≥1.1 |
| 180 | P2T/A49G/K152E/R276W | | ≥1.1 |
| 181 | K155R/R206S/R276W | | ≥1.1 |
| 182 | R276W | g204a | ≥1.1 |
| 183 | R276W | a853t/g854c/c954g | ≥1.1 |
| 184 | R276W | c201t/a280c | ≥1.1 |
| 185 | T114S/R276W | | ≥1.1 |
| 186 | R33L/R276W | t7a/c8g | ≥1.1 |
| 187 | R276W | c954g | ≥1.1 |
| 188 | P2T/R276W/V318C | | ≥1.1 |
| 189 | A49G/K152E/R276W | | ≥1.1 |
| 190 | D11K/V255I/R276M | g231a/c801t | ≥1.1 |
| 191 | K132N/R276W | a280c | ≥1.1 |
| 192 | K52R/R276W | | ≥1.0 |
| 193 | P2T/A49G/S233V/A246L/R276W/N302S | | ≥1.0 |
| 194 | A49G/K132A/K152E/R276W | a280c | ≥1.0 |
| 195 | S3H/R276W | t99g/c168a | ≥1.0 |
| 196 | P2T/V24G/A49G/R276W | c954g | ≥1.0 |
| 197 | R276W | c201t | ≥1.0 |
| 198 | R276W/V318C | t6g | ≥1.0 |
| 199 | R33L/A56E/R276W | t7a/c8g | ≥1.0 |
| 200 | K132N/R276W | g465a/t618c/t907c | ≥1.0 |
| 201 | K132N/K155R/R276W/V283H | t907c | ≥1.0 |
| 202 | K36Q/R276W | | ≥1.0 |
| 203 | R276W | a478c | ≥1.0 |
| 204 | R276W | c855t | ≥1.0 |
| 205 | R276W | t82a/c83g | ≥1.0 |
| 206 | P2T/A49G/S261N/R276W | a853t/g854c/c954g | ≥1.0 |
| 207 | P2T/K132A/R276W | a280c | ≥1.0 |
| 208 | K132N/R276W | | ≥1.0 |
| 209 | R276W | t7a/c8g | ≥1.0 |
| 210 | P168S/R276W | | ≥1.0 |
| 211 | A56E/T114S/R276W | t7a/c8g | ≥1.0 |
| 212 | P2T/A49G/K68G/S261N/R276W/V318C | a853t/g854c | ≥1.0 |
| 213 | R276W | c906t | ≥1.0 |
| 214 | A49G/K132N/K152E/R276W/N302S | a280c | ≥1.0 |
| 215 | R276W | g108a/t907c | ≥1.0 |
| 216 | K132N/R276W | t289a/c290g/t291c | ≥1.0 |

TABLE 4-3-continued

| Additional XR Variants with Improved Activity | | | |
|---|---|---|---|
| Variant No. | XR-Active Mutations wrt XR WT | XR-Silent Mutations wrt XR WT | Xylose Utilization Activity (Compared to Positive Control) |
| 217 | D11K/R276W | g108a/g465a | ≥1.0 |
| 218 | R276W | t82a/c83g/c201t/a280c/t358c/a378t/t511c | ≥1.0 |
| 219 | P252C/R276W | | ≥1.0 |
| 220 | R276W | c21t | ≥1.0 |
| 221 | P2T/A49G/R276W/N302S | | ≥1.0 |
| 222 | P2T/V24G/R276W/V318C | | ≥1.0 |
| 223 | D11K/K155Y/R206S/R276W | g108a/t289a/c290g/t291c | ≥1.0 |
| 224 | S3H/R33L/T114S/R276W | c168a | ≥1.0 |

TABLE 4-4

| Additional XR Variants with Improved Activity | | | |
|---|---|---|---|
| Variant No: | XR-Active Mutations wrt XR WT | XR-Silent Mutations wrt XR WT | Xylose Utilization Activity (Compared to Positive Control) |
| 272 (Positive Control) | P2T/A49G/K132N/S233K/I267V/R276W | t99a/g156a/t747c/t751a/c752g, t753c | 1.00 |
| 377 | P2T/E46C/A49G/F107Y/K132N/S233K/I267V/R276W | t99a/g156a/t747c/t751a/c752g/t753c | ≥1.2 |
| 378 | P2T/C19L/E46C/A49G/F107Y/K132N/S233K/I267V/R276W | t99a/g156a/t747c/t751a/c752g/t753c | ≥1.1 |
| 379 | P2T/A49G/K132N/S233K/I267V/R276W | t99a/g156a/t552g/t747c/t751a/c752g/t753c/a756t/c816t | ≥1.1 |
| 380 | P2T/A49G/K132N/S233K/I267V/R276W | t99a/g108a/g156a/t322c/t747c/t751a/c752g/t753c | ≥1.0 |
| 381 | P2T/A49G/K132N/S233K/I267V/R276W | t99a/g156a/t552g/t747c/t751a/c752g/t753c | ≥1.0 |
| 382 | P2T/E46C/A49G/K132N/V164I/S233K/I267V/R276W | t99a/g156a/t747c/t751a/c752g/t753c | ≥1.0 |
| 383 | P2T/C19L/E46C/A49G/K132N/S233K/I267V/R276W | t99a/g156a/t747c/t751a/c752g/t753c | ≥1.0 |
| 384 | P2T/A49G/K132N/S233K/R276W | t99a/g108a/g156a/t747c/t751a/c752g/t753c/c801t | ≥1.0 |
| 385 | P2T/A49G/K132N/P168S/S233K/I267V/R276W | t99a/g156a/t322c/t747c/t751a/c752g/t753c | ≥1.0 |
| 386 | P2T/A49G/K132N/P168S/S233K/I267V/R276W | t99a/g108a/g156a/t322c/g513a/t747c/t751a/c752g/t753c/c816t | ≥1.0 |

In some additional experiments, the *Pichia stipitis* xylitol dehydrogenase (XD.2) was subjected to directed evolution to improve xylose utilization activity using PCR amplification known in the art (See e.g., WO 2010/144103). Purified PCR products were pooled and transformed into *S. cerevisiae* (THERMOSACC®; LYCC6825; Lallemand) to produce the library via homologous recombination (See e.g., Oldenburg et al., Nucl. Acids Res., 25(2):451-452 [1997], which is incorporated herein by reference). The library was screened for xylose fermentation activity as described in Example 2. Variants that exhibited activity significantly above the positive control were retested and sequenced. Variants that exhibited activity improved above background are provided in Table 4-5.

TABLE 4-5

| XD Variants with Improved Activity | | | |
|---|---|---|---|
| Variant No: | XD-Active Mutations wrt XD WT | XD-Silent Mutations wrt XD WT | Xylose Utilization Activity (Compared to Positive Control) |
| 13 (Positive Control) | | | 1.00 |
| 225 | E235K | | ≥1.2 |
| 226 | V206A | | ≥1.2 |
| 227 | A49Q | | ≥1.2 |
| 228 | K352E | | ≥1.2 |
| 229 | M215C | | ≥1.1 |
| 230 | P256A | | ≥1.1 |
| 231 | | t24g | ≥1.1 |
| 232 | S81G | | ≥1.1 |

TABLE 4-5-continued

| XD Variants with Improved Activity | | | |
|---|---|---|---|
| Variant No: | XD-Active Mutations wrt XD WT | XD-Silent Mutations wrt XD WT | Xylose Utilization Activity (Compared to Positive Control) |
| 233 | | a768t | ≥1.1 |
| 234 | T19L | | ≥1.1 |
| 235 | G202D | | ≥1.1 |
| 236 | L189C | | ≥1.1 |
| 237 | P5R | | ≥1.1 |
| 238 | G231H | | ≥1.1 |
| 239 | D210W | | ≥1.1 |
| 240 | T230V | | ≥1.1 |
| 241 | | a780g | ≥1.1 |
| 242 | | a732g | ≥1.1 |
| 243 | T286V | | ≥1.1 |
| 244 | | c630t | ≥1.1 |
| 245 | G231A | | ≥1.1 |
| 246 | P5E | | ≥1.1 |
| 247 | D218R | | ≥1.1 |
| 248 | S228P | | ≥1.0 |
| 249 | T19Q | | ≥1.0 |
| 250 | V287L | | ≥1.0 |
| 251 | V205C | | ≥1.0 |
| 252 | V205H | | ≥1.0 |
| 253 | V187M | | ≥1.0 |
| 254 | H149R | | ≥1.0 |
| 255 | F296R | | ≥1.0 |
| 256 | A239C | | ≥1.0 |
| 257 | L260Q | | ≥1.0 |
| 258 | G241W/K307R | | ≥1.0 |
| 259 | E235Q | | ≥1.0 |
| 260 | D13G | | ≥1.0 |
| 261 | A350D | | ≥1.0 |
| 262 | T252S | | ≥1.0 |
| 263 | C251T | | ≥1.0 |
| 264 | N227T | | ≥1.0 |
| 265 | M215A | | ≥1.0 |
| 266 | C251G | | ≥1.0 |
| 267 | K229R | | ≥1.0 |
| 268 | F226V | | ≥1.0 |
| 269 | P256Q | | ≥1.0 |
| 270 | D327A | | ≥1.0 |

The following Table (Table 4-6) provides results for XR and XD combinatorial variants with improved activity compared to a positive control having the active mutations indicated in the Table.

TABLE 4-6

| XR & XD Combinatorial Variants with Improved Activity | | | | | |
|---|---|---|---|---|---|
| | XR | | XD | | Xylose Utilization Activity |
| Variant No. | Active Mutations wrt XR WT | Silent Mutations wrt XR WT | Active Mutations wrt XD WT | Silent Mutations wrt XD WT | Improvement (Relative to Positive Control) |
| 152 (Positive Control) | P2T/A49G/R276W | | | | 1.00 |
| 271 | P2T/K132N/ K152E/R276W | | F209S/ N211K | | ≥1.2 |
| 272 | P2T/A49G/ K132N/S233K/ I267V/R276W | t99a/g156a/ t747c/t751a/ c752g/t753c | | | ≥1.2 |
| 273 | P2T/A49G/K132N/I267V/ R276W | t99a/g204a/ t618c/t697a/ c698g/t699c/ t747c/t751a/ c752g/t753c | | | ≥1.2 |
| 274 | P2T/A49G/P168S/R206S/ I267V/ R276W | g456a/t895c | | | ≥1.2 |
| 275 | P2T/A49G/K52R/K152E/ S233K/ I267V/R276W | g231a/t322c | | | ≥1.2 |
| 276 | P2T/A49G/ K132N/I267V/ R276W | | | | ≥1.2 |
| 277 | P2T/A49G/ R276W | | G232L | | ≥1.2 |
| 278 | P2T/A49G/ K132N/R276W | t99a/g204a | | | ≥1.2 |
| 279 | P2T/A49G/ K132N/I267V/ R276W | t99a/t747c/ t751a/c752g/ t753c | | | ≥1.2 |
| 280 | P2T/A49G/ K132N/R276W | t99g/g108a/ a853t/g854c/ c855g | | | ≥1.2 |
| 281 | P2T/A49G/S233K/I267V/ R276W | t99a/g513a/ t747c/t751a/ c752g/t753c | | | ≥1.2 |

TABLE 4-6-continued

XR & XD Combinatorial Variants with Improved Activity

| Variant No. | XR: Active Mutations wrt XR WT | XR: Silent Mutations wrt XR WT | XD: Active Mutations wrt XD WT | XD: Silent Mutations wrt XD WT | Xylose Utilization Activity: Improvement (Relative to Positive Control) |
|---|---|---|---|---|---|
| 282 | P2T/A49G/R206S/S233K/I267V/R276W | t895c | | | ≥1.2 |
| 283 | P2T/A49G/K132N/R276W | g156a/g204a/c801t | | | ≥1.2 |
| 284 | P2T/A49G/K132N/R276W | t753g/a756t/a853t/g854c/c855g | | | ≥1.2 |
| 285 | P2T/A49G/S233K/I267V/R276W | t895c | | | ≥1.2 |
| 286 | P2T/A49G/K152E/P168S/S233V/I267V/R276W | t895c | | | ≥1.1 |
| 287 | P2T/A49G/S233K/I267V/R276W | t618c/t747c/t751a/c752g/t753c | | | ≥1.1 |
| 288 | P2T/A49G/R276W | | T225X | a693w | ≥1.1 |
| 289 | P2T/A49G/R276W | | | c336t | ≥1.1 |
| 290 | P2T/A49G/S233K/I267V/R276W | t322c/t895c | | | ≥1.1 |
| 291 | P2T/A49G/R276W | | E235K | | ≥1.1 |
| 292 | P2T/A49G/S233K/I267V/R276W | t618c/t895c | | | ≥1.1 |
| 293 | P2T/A49G/R276W | | K214A | | ≥1.1 |
| 294 | P2T/A49G/K132N/I267V/R276W | t99a/g156a | | | ≥1.1 |
| 295 | P2T/A49G/R276W | | K229V | | ≥1.1 |
| 296 | P2T/A49G/R276W | | | | ≥1.1 |
| 297 | P2T/A49G/R206S/S233K/I267V/R276W | t9c/t895c | | | ≥1.1 |
| 298 | P2T/A49G/I267V/R276W | t99a/t697a/c698g/t699c/t747c/t751a/c752g/t753c | | | ≥1.1 |
| 299 | P2T/A49G/P168S/S233K/R276W | t9c/t618c | | | ≥1.1 |
| 300 | P2T/A49G/S233K/I267V/R276W | g834a/t895c | | | ≥1.1 |
| 301 | P2T/A49G/G227D/P252C/G264D/R276W | t753g | | | ≥1.1 |
| 302 | P2T/A49G/K132N/R276W | a853t/g854c/c855g | | | ≥1.1 |
| 303 | P2T/S3H/A49G/P168S/S233K/R276W | g456a/c801t/t895c | | | ≥1.1 |
| 304 | P2T/A49G/S233K/I267V/R276W | t99a/t618c/t747c/t751a/c752g/t753c | | | ≥1.1 |
| 305 | P2T/R206S/R276W | | A49Q | | ≥1.1 |
| 306 | P2T/A49G/I267V/R276W | g156a | | | ≥1.1 |
| 307 | P2T/A49G/I267V/R276W | t895c/ | | | ≥1.1 |
| 308 | P2T/A49G/R206S/S233V/R276W | a504g | | | ≥1.1 |
| 309 | P2T/A49G/I267V/R276W | t99a | | | ≥1.1 |
| 310 | P2T/A49G/S233K/R276W | c801t/t895c | | | ≥1.1 |
| 311 | P2T/A49G/R206S/R276W | t697a/c698g/c801t/t895c | | | ≥1.1 |
| 312 | P2T/A49G/P252C/R276W | t753g/a853t/g854c/c855g | | | ≥1.1 |
| 313 | P2T/K132N/K152E/R276W | | K352E | | ≥1.1 |
| 314 | P2T/A49G/I267V/R276W | t747c/t751a/c752g/t753c | | | ≥1.1 |
| 315 | P2T/A49G/I267V/R276W | | | | ≥1.1 |
| 316 | P2T/A49G/R276W | | C251A | | ≥1.1 |
| 317 | P2T/A49G/R276W | | G232R | | ≥1.1 |

TABLE 4-6-continued

XR & XD Combinatorial Variants with Improved Activity

| | XR | | XD | | Xylose Utilization Activity |
|---|---|---|---|---|---|
| Variant No. | Active Mutations wrt XR WT | Silent Mutations wrt XR WT | Active Mutations wrt XD WT | Silent Mutations wrt XD WT | Improvement (Relative to Positive Control) |
| 318 | P2T/A49G/R206S/S233V/R276W | c801t/t895c | | | ≥1.1 |
| 319 | P2T/A49G/K132N/R276W | g204a/t753g/a756t/a853t/g854c/c855g | | | ≥1.1 |
| 320 | P2T/A49G/R206S/R276W | t697a/c698g/t699c | | | ≥1.1 |
| 321 | P2T/A49G/R276W | | K229M | | ≥1.1 |
| 322 | P2T/A49G/S233K/I267V/R276W | t322c/t618c/t895c | | | ≥1.1 |
| 323 | P2T/K132N/K152E/R276W | | A49Q/E235K | | ≥1.1 |
| 324 | P2T/A49G/R276W | | | a780t | ≥1.1 |
| 325 | P2T/A49G/I267V/R276W | t99a/g156a/g204a | | | ≥1.1 |
| 326 | P2T/A49G/R276W | | D327X | | ≥1.1 |
| 327 | P2T/K132N/K152E/R276W | | A49Q | | ≥1.1 |
| 328 | P2T/A49G/P168S/R276W | | | | ≥1.1 |
| 329 | P2T/A49G/R276W | | V206A | | ≥1.0 |
| 330 | P2T/A49G/R276W | | V206A | | ≥1.0 |
| 331 | P2T/A49G/R276W | | K337R | | ≥1.0 |
| 332 | P2T/A49G/K152E/I267V/R276W | a504g | | | ≥1.0 |
| 333 | P2T/A49G/K132N/R276W | a478c/g480t | | | ≥1.0 |
| 334 | P2T/K36Q/A49G/G227D/R276W | t99g/t753g/a756t/a853t/g854c/c855g | | | ≥1.0 |
| 335 | P2T/A49G/R276W | | V287L | | ≥1.0 |
| 336 | P2T/A49G/D86N/K132N/R276W | g204a/a478c/g480t/t753g/a756t/a853t/g854c/c855g | | | ≥1.0 |
| 337 | P2T/A49G/R206S/R276W | | A49Q | | ≥1.0 |
| 338 | P2T/A49G/R276W | | G241E | | ≥1.0 |
| 339 | P2T/A49G/G227D/R276W | t753g/a756t/a853t/g854c/c855g | | | ≥1.0 |
| 340 | P2T/S3X/A49G/S233X/I267X/R276W/L299X | t84w | | | ≥1.0 |
| 341 | P2T/A49G/I267V/R276W | a504g/c816t/t895c | | | ≥1.0 |
| 342 | P2T/A49G/R276W | | H112Q | | ≥1.0 |
| 343 | P2T/A49G/R276W | | K238G | | ≥1.0 |
| 344 | P2T/A49G/P168S/R276W | t895c | | | ≥1.0 |
| 345 | P2T/A49G/G227D/I267V/R276W | | | | ≥1.0 |
| 346 | P2T/A49G/K132N/G227D/P252C/R276W | t753g/a853t/g854c/c855g | | | ≥1.0 |
| 347 | P2T/A49G/R276W | | K352Q | | ≥1.0 |
| 348 | P2T/A49G/I267V/R276W | g204a/t697a/c698g/t699c/t747c/t751a/c752g/t753c | | | ≥1.0 |
| 349 | R276F | t811a/c812g/c816t | I208R/N211K | | ≥1.0 |
| 350 | P2T/A49G/I267V/R276W | g231a/t322c/t895c | | | ≥1.0 |
| 351 | P2T/A49G/R276W | | K259S | | ≥1.0 |
| 352 | P2T/A49G/K132N/G227D/R276W | a478c/g480t/t753g/a756t/a853t/g854c/c855g | | | ≥1.0 |

TABLE 4-6-continued

XR & XD Combinatorial Variants with Improved Activity

| | XR | | XD | | Xylose Utilization Activity |
|---|---|---|---|---|---|
| Variant No. | Active Mutations wrt XR WT | Silent Mutations wrt XR WT | Active Mutations wrt XD WT | Silent Mutations wrt XD WT | Improvement (Relative to Positive Control) |
| 353 | P2T/A49G/I267V/ R276W | g156a/t747c/ t751a/c752g/ t753c | | | ≥1.0 |
| 354 | P2T/A49G/S233V/ I267V/R276W g456a/t895c | g156a/g231a/ t322c/ | | | ≥1.0 |
| 355 | P2T/A49G/G227D/ P252C/R276W | t753g/a853t/ g854c/c855g | | | ≥1.0 |
| 356 | P2T/A49G/R276W | | K352G | | ≥1.0 |
| 357 | P2T/A49G/R276W | a853t/g854c/ c855g | | | ≥1.0 |
| 358 | P2T/K132N/K152E/ R276W | | E235K | | ≥1.0 |
| 359 | P2T/A49G/K52R/ R206S/I267V/R276W | t9c/t84a/ g231a/t697a/ c698g/t895c | | | ≥1.0 |
| 360 | P2T/A49G/K132N/ R276W | | | | ≥1.0 |
| 361 | P2T/A49G/R276W | | K352E | | ≥1.0 |
| 362 | P2T/A49G/K52R/ R276W | t99a | | | ≥1.0 |
| 363 | P2T/A49G/R276W | | H112A | | ≥1.0 |
| 364 | P2T/A49G/S233V/ R276W | t895c | | | ≥1.0 |
| 365 | P2T/R206S/R276W | | E235K | | ≥1.0 |
| 366 | P2T/A49G/R276W | t99a/g156a/ g204a | | | ≥1.0 |
| 367 | P2T/A49G/R276W | | S26A | | ≥1.0 |
| 368 | P2T/A49G/R276W | | D210A | | ≥1.0 |
| 369 | P2T/A49G/R206S/ R276W | | K352E | | ≥1.0 |
| 370 | P2T/A49G/R276W | t618c/t697a/ c698g/c801t/ t895c | | | ≥1.0 |
| 371 | P2T/A49G/S233V/ I267V/R276W | a504g/t895c | | | ≥1.0 |
| 372 | P2T/W20X/A49G/ D63X/R276W | c111n/c822t/ a825c/a853t/ g854c/c855g | | | ≥1.0 |
| 373 | P2T/A49G/R276W | t84a | | | ≥1.0 |
| 374 | P2T/A49G/R276W | g204a/c801t | | | ≥1.0 |
| 375 | P2T/A49G/R276W | t552g/c801t/ t895c | | | ≥1.0 |
| 376 | P2T/A49G/R276W | c801t | | | ≥1.0 |

The sequences of some variants included in the above table(s) are provided below. Variant 3 has active substitutions in both the XR and XD (R276F and F209S/N211K, respectively), as well as XR silent mutations (t811a/c812g/c816t), as shown in SEQ ID NOS:50 and 51 (XR DNA and amino acid sequences, respectively), and SEQ ID NOS:52 and 53 (XD DNA and amino acid sequences, respectively).

(SEQ ID NO: 50)

```
ATGCCTTCTATTAAGTTGAACTCTGGTTACGACATGCCAGCCGTCGGT
TTCGGCTGTTGGAAAGTTGACGTTGACACCTGTTCTGAACAGGTCTAC
CGTGCTATCAAGACCGGTTACAGATTGTTCGACGGTGCCGAAGATTAC
GCCAACGAAAAGTTAGTTGGTGCCGGTGTCAAGAAGGCCATTGACGAA
GGTATCGTCAAGCGTGAAGACTTGTTCCTTACCTCCAAGTTGTGGAAC
AACTACCACCACCCAGACAACGTCGAAAAGGCCTTGAACAGAACCCTT
TCTGACTTGCAAGTTGACTACGTTGACTTGTTCTTGATCCACTTCCCA
GTCACCTTCAAGTTCGTTCCATTAGAAGAAAAGTACCCACCAGGATTC
TACTGTGGTAAGGGTGACAACTTCGACTACGAAGATGTTCCAATTTTA
GAGACCTGGAAGGCTCTTGAAAAGTTGGTCAAGGCCGGTAAGATCAGG
```

-continued

```
TCTATCGGTGTTTCTAACTTCCCAGGTGCTTTGCTCTTGGACTTGTTG
AGAGGTGCTACCATCAAGCCATCTGTCTTGCAAGTTGAACACCACCCA
TACTTGCAACAACCAAGATTGATCGAGTTCGCTCAATCCCGTGGTATT
GCTGTCACCGCTTACTCTTCGTTCGGTCCTCAATCTTTCGTTGAATTG
AACCAAGGTAGAGCTTTGAACACTTCTCCATTGTTCGAGAACGAAACT
ATCAAGGCTATCGCTGCTAAGCACGGTAAGTCTCCAGCTCAAGTCTTG
TTGAGATGGTCTTCCCAAAGAGGCATTGCCATCATTCCAAAGAGCAAT
ACTGTCCCATTCTTGTTGGAAAACAAGGATGTCAACAGCTTCGACTTG
GACGAACAAGATTTCGCTGACATTGCCAAGTTGGACATCAACTTGAGA
TTCAACGACCCATGGGACTGGGACAAGATTCCTATCTTCGTCTAA
```

(SEQ ID NO: 51)

```
MPSIKLNSGYDMPAVGFGCWKVDVDTCSEQVYRAIKTGYRLFDGAEDY
ANEKLVGAGVKKAIDEGIVKREDLFLTSKLWNNYHHPDNVEKALNRTL
SDLQVDYVDLFLIHFPVTFKFVPLEEKYPPGFYCGKGDNFDYEDVPIL
ETWKALEKLVKAGKIRSIGVSNFPGALLLDLLRGATIKPSVLQVEHHP
YLQQPRLIEFAQSRGIAVTAYSSFGPQSFVELNQGRALNTSPLFENET
IKAIAAKHGKSPAQVLLRWSSQRGIAIIPKSNTVPFLLENKDVNSFDL
DEQDFADIAKLDINLRFNDPWDWDKIPIFV
```

-continued (SEQ ID NO: 52)

```
ATGACCGCTAATCCCTCTCTTGTTTTGAATAAGATTGACGACATTTCT
TTTGAAACTTACGATGCTCCCGAAATTAGCGAACCCACAGACGTTTTA
GTTCAAGTTAAAAAAACTGGTATCTGCGGTTCTGACATCCACTTCTAC
GCTCATGGAAGGATCGGCAACTTCGTCTTAACAAAGCCAATGGTTCTG
GGTCATGAAAGCGCGGGTACTGTTGTTCAAGTCGGTAAAGGTGTTACT
TCACTGAAGGTTGGTGATAACGTCGCAATCGAGCCCGGTATTCCATCT
AGGTTCAGTGATGAGTACAAATCTGGTCACTACAACCTGTGTCCACAC
ATGGCATTTGCTGCTACTCCCAATTCTAAAGAGGGTGAACCAAACCCA
CCAGGAACTCTATGTAAGTACTTCAAATCTCCAGAAGACTTCCTGGTT
AAGTTACCCGATCATGTTTCTTTGGAGTTGGGTGCTTTGGTCGAGCCA
CTATCTGTTGGGGTCCATGCTAGTAAATTAGGCTCCGTTGCATTTGGC
GATTACGTTGCTGTTTTTGGTGCTGGTCCAGTAGGATTACTGGCTGCC
GCTGTCGCTAAGACATTTGGTGCCAAGGGTGTGATTGTCGTTGATATA
TCTGACAAGAAGCTGAAGATGGCCAAAGACATAGGTGCCGCTACACAT
ACCTTCAACTCCAAGACGGGAGGTAGTGAAGAATTGATCAAAGCCTTC
GGTGGTAATGTACCAAATGTTGTCTTGGAATGTACTGGGGCTGAACCA
TGTATTAAGCTAGGTGTTGATGCCATCGCACCAGGTGGTAGATTCGTG
CAAGTTGGTAATGCTGCTGGTCCCGTGTCCTTTCCCATAACAGTGTTC
GCTATGAAAGAACTTACTTTGTTTGGTTCATTTCGTTATGGTTTCAAC
GACTATAAGACAGCCGTGGGTATCTTTGATACTAACTACCAGAACGGT
AGAGAGAATGCTCCCATTGACTTTGAACAGCTTATCACGCACAGATAC
AAATTCAAAGACGCCATTGAAGCCTACGACCTAGTAAGAGCAGGTAAA
GGGGCTGTCAAGTGTTTGATTGATGGTCCAGAATAA
```

(SEQ ID NO: 53)

```
MTANPSLVLNKIDDISFETYDAPEISEPTDVLVQVKKTGICGSDIHFY
AHGRIGNFVLTKPMVLGHESAGTVVQVGKGVTSLKVGDNVAIEPGIPS
RFSDEYKSGHYNLCPHMAFAATPNSKEGEPNPPGTLCKYFKSPEDFLV
KLPDHVSLELGALVEPLSVGVHASKLGSVAFGDYVAVFGAGPVGLLAA
AVAKTFGAKGVIVVDISDKKLKMAKDIGAATHTFNSKTGGSEELIKAF
GGNVPNVVLECTGAEPCIKLGVDAIAPGGRFVQVGNAAGPVSFPITVF
AMKELTLFGSFRYGFNDYKTAVGIFDTNYQNGRENAPIDFEQLITHRY
KFKDAIEAYDLVRAGKGAVKCLIDGPE
```

The DNA and amino acid sequences of variant 152 (P2T/A49G/R276W in XR) are provided below (SEQ ID NOS:54 and 55).

(SEQ ID NO: 54)

```
ATGACCTCTATTAAGTTGAACTCTGGTTACGACATGCCAGCCGTCGGTT
TCGGCTGTTGGAAAGTTGACGTTGACACCTGTTCTGAACAGGTCTACCG
TGCTATCAAGACCGGTTACAGATTGTTCGACGGTGCCGAAGATTACGGC
AACGAAAAGTTAGTTGGTGCCGGTGTCAAGAAGGCCATTGACGAAGGTA
TCGTCAAGCGTGAAGACTTGTTCCTTACCTCCAAGTTGTGGAACAACTA
CCACCACCCAGACAACGTCGAAAAGGCCTTGAACAGAACCCTTTCTGAC
TTGCAAGTTGACTACGTTGACTTGTTCTTGATCCACTTCCCAGTCACCT
TCAAGTTCGTTCCATTAGAAGAAAAGTACCCACCAGGATTCTACTGTGG
TAAGGGTGACAACTTCGACTACGAAGATGTTCCAATTTTAGAGACCTGG
AAGGCTCTTGAAAAGTTGGTCAAGGCCGGTAAGATCAGGTCTATCGGTG
TTTCTAACTTCCCAGGTGCTTTGCTCTTGGACTTGTTGAGAGGTGCTAC
CATCAAGCCATCTGTCTTGCAAGTTGAACACCACCCATACTTGCAACAA
CCAAGATTGATCGAGTTCGCTCAATCCCGTGGTATTGCTGTCACCGCTT
ACTCTTCGTTCGGTCCTCAATCTTTCGTTGAATTGAACCAAGGTAGAGC
TTTGAACACTTCTCCATTGTTCGAGAACGAAACTATCAAGGCTATCGCT
GCTAAGCACGGTAAGTCTCCAGCTCAAGTCTTGTTGAGATGGTCTTCCC
AAAGAGGCATTGCCATCATTCCAAAGTCCAACACTGTCCCATGGTTGTT
GGAAAACAAGGATGTCAACAGCTTCGACTTGGACGAACAAGATTTCGCT
GACATTGCCAAGTTGGACATCAACTTGAGATTCAACGACCCATGGGACT
GGGACAAGATTCCTATCTTCGTCTAA
```

(SEQ ID NO: 55)

```
MTSIKLNSGYDMPAVGFGCWKVDVDTCSEQVYRAIKTGYRLFDGAEDYG
NEKLVGAGVKKAIDEGIVKREDLFLTSKLWNNYHHPDNVEKALNRTLSD
LQVDYVDLFLIHFPVTFKFVPLEEKYPPGFYCGKGDNFDYEDVPILETW
KALEKLVKAGKIRSIGVSNFPGALLLDLLRGATIKPSVLQVEHHPYLQQ
PRLIEFAQSRGIAVTAYSSFGPQSFVELNQGRALNTSPLFENETIKAIA
AKHGKSPAQVLLRWSSQRGIAIIPKSNTVPWLLENKDVNSFDLDEQDFA
DIAKLDINLRFNDPWDWDKIPIFV
```

The DNA and amino acid sequences of variant 272 (P2T/A49G/K132N/S233K/I267V/R276W in XR) are provided below (SEQ ID NOS:56 and 57).

(SEQ ID NO: 56)

```
ATGACCTCTATTAAGTTGAACTCTGGTTACGACATGCCAGCCGTCGGT
TTCGGCTGTTGGAAAGTTGACGTTGACACCTGTTCTGAACAGGTCTAC
```

-continued

```
CGAGCTATCAAGACCGGTTACAGATTGTTCGACGGTGCCGAAGATTAC
GGCAACGAAAAATTAGTTGGTGCCGGTGTCAAGAAGGCCATTGACGAA
GGTATCGTCAAGCGTGAAGACTTGTTCCTTACCTCCAAGTTGTGGAAC
AACTACCACCACCCAGACAACGTCGAAAAGGCCTTGAACAGAACCCTT
TCTGACTTGCAAGTTGACTACGTTGACTTGTTCTTGATCCACTTCCCA
GTCACCTTCAAGTTCGTTCCATTAGAAGAAAAGTACCCACCAGGATTC
TACTGTGGTAACGGTGACAACTTCGACTACGAAGATGTTCCAATTTTA
GAGACCTGGAAGGCTCTTGAAAAGTTGGTCAAGGCCGGTAAGATCAGG
TCTATCGGTGTTTCTAACTTCCCAGGTGCTTTGCTCTTGGACTTGTTG
AGAGGTGCTACCATCAAGCCATCTGTCTTGCAAGTTGAACACCACCCA
TACTTGCAACAACCAAGATTGATCGAGTTCGCTCAATCCCGTGGTATT
GCTGTCACCGCTTACTCTTCGTTCGGTCCTCAATCTTTCGTTGAATTG
AACCAAGGTAGAGCTTTGAACACTAAGCCATTGTTCGAGAACGAAACT
ATCAAGGCTATCGCTGCTAAGCACGGCAAGAGCCCAGCTCAAGTCTTG
TTGAGATGGTCTTCCCAAAGAGGCATTGCCGTTATTCCAAAGTCCAAC
ACTGTCCCATGGTTGTTGGAAAACAAGGATGTCAACAGCTTCGACTTG
GACGAACAAGATTTCGCTGACATTGCCAAGTTGGACATCAACTTGAGA
TTCAACGACCCATGGGACTGGGACAAGATTCCTATCTTCGTCTAA
```

(SEQ ID NO: 57)

```
MTSIKLNSGYDMPAVGFGCWKVDVDTCSEQVYRAIKTGYRLFDGAEDY
GNEKLVGAGVKKAIDEGIVKREDLFLTSKLWNNYHHPDNVEKALNRTL
SDLQVDYVDLFLIHFPVTFKFVPLEEKYPPGFYCGNGDNFDYEDVPIL
ETWKALEKLVKAGKIRSIGVSNFPGALLLDLLRGATIKPSVLQVEHHP
YLQQPRLIEFAQSRGIAVTAYSSFGPQSFVELNQGRALNTKPLFENET
IKAIAAKHGKSPAQVLLRWSSQRGIAVIPKSNTVPWLLENKDVNSFDL
DEQDFADIAKLDINLRFNDPWDWDKIPIFV
```

The DNA and amino acid sequences of variant 377 (P2T/E46C/A49G/F107Y/K132N/S233K/I267V/R276W in XR) are provided below (SEQ ID NOS:58 and 59).

(SEQ ID NO: 58)

```
ATGACCTCTATTAAGTTGAACTCTGGTTACGACATGCCAGCCGTCGGT
TTCGGCTGTTGGAAAGTTGACGTTGACACCTGTTCTGAACAGGTCTAC
CGAGCTATCAAGACCGGTTACAGATTGTTCGACGGTGCCGAAGATTAC
GGCAACGAAAAATTAGTTGGTGCCGGTGTCAAGAAGGCCATTGACGAA
GGTATCGTCAAGCGTGAAGACTTGTTCCTTACCTCCAAGTTGTGGAAC
AACTACCACCACCCAGACAACGTCGAAAAGGCCTTGAACAGAACCCTT
TCTGACTTGCAAGTTGACTACGTTGACTTGTTCTTGATCCACTTCCCA
GTCACCTTCAAGTTCGTTCCATTAGAAGAAAAGTACCCACCAGGATTC
TACTGTGGTAACGGTGACAACTTCGACTACGAAGATGTTCCAATTTTA
GAGACCTGGAAGGCTCTTGAAAAGTTGGTCAAGGCCGGTAAGATCAGG
TCTATCGGTGTTTCTAACTTCCCAGGTGCTTTGCTCTTGGACTTGTTG
AGAGGTGCTACCATCAAGCCATCTGTCTTGCAAGTTGAACACCACCCA
TACTTGCAACAACCAAGATTGATCGAGTTCGCTCAATCCCGTGGTATT
GCTGTCACCGCTTACTCTTCGTTCGGTCCTCAATCTTTCGTTGAATTG
AACCAAGGTAGAGCTTTGAACACTAAGCCATTGTTCGAGAACGAAACT
ATCAAGGCTATCGCTGCTAAGCACGGCAAGAGCCCAGCTCAAGTCTTG
TTGAGATGGTCTTCCCAAAGAGGCATTGCCGTTATTCCAAAGTCCAAC
ACTGTCCCATGGTTGTTGGAAAACAAGGATGTCAACAGCTTCGACTTG
GACGAACAAGATTTCGCTGACATTGCCAAGTTGGACATCAACTTGAGA
TTCAACGACCCATGGGACTGGGACAAGATTCCTATCTTCGTCTAA
```

(SEQ ID NO: 59)

```
MTSIKLNSGYDMPAVGFGCWKVDVDTCSEQVYRAIKTGYRLFDGAEDY
GNEKLVGAGVKKAIDEGIVKREDLFLTSKLWNNYHHPDNVEKALNRTL
SDLQVDYVDLFLIHFPVTFKFVPLEEKYPPGFYCGNGDNFDYEDVPIL
ETWKALEKLVKAGKIRSIGVSNFPGALLLDLLRGATIKPSVLQVEHHP
YLQQPRLIEFAQSRGIAVTAYSSFGPQSFVELNQGRALNTKPLFENET
IKAIAAKHGKSPAQVLLRWSSQRGIAVIPKSNTVPWLLENKDVNSFDL
DEQDFADIAKLDINLRFNDPWDWDKIPIFV
```

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of the present invention.

We claim:

1. An isolated xylose reductase variant, wherein said variant has xylose reductase activity and comprises a substitution at at least two positions selected from 46, 47, and 49, in SEQ ID NO:2.

2. The isolated xylose reductase variant of claim 1, wherein said variant has xylose reductase activity and further comprises a substitution at one or more positions selected from P2T, S3H, S3R, S3W, S3X, N7L, D11K, A14V, F17W, C19L, W20X, D23E, V24G, R33L, R33V, K36Q, E46C, E46K, D47G, D47N, A49G, K52R, A56E, A56Y, I62V, D63X, K68G, K68M, K68R, D86N, E89N, E89V, S97R, S97T, D102T, F107Y, L108Y, T114S, K116Q, K123C, K132A, K132N, D134E, D134H, D134V, I143L, K152A, K152E, K152H, K152Q, K155A, K155D, K155I, K155R, K155Y, G157R, I162L, P168S, S184A, R206S, R206V, Q219H, Q219L, Q219T, L224A, L224S, L224V, N225D, N225E, N225K, N225S, N225Y, Q226D, Q226E, Q226S, Q226V, G227D, R228T, N231G, N231H, N231L, N231S, T232A, T232C, T232S, T232V, S233C, S233F, S233G, S233I, S233K, S233V, S233X, F236L, T240V, K242L, A245S, A246L, A246S, G249D, P252C, V255I, S261A, S261C, S261N, S261T, G264D; A266V, A266C, I267V, I267X, K270R, S271G, N272P, P275A, R276M, R276F, R276W, E279Q, K281L, K281V, D282C, D282G, D282R, V283H, S285E, S285T, A297H, A297S, L299X, I301C, I301Y, N302D, N302G, N302S, L303I, L303V, and V318C, in SEQ ID NO:2.

3. The isolated xylose reductase variant of claim 1, wherein said variant has xylose reductase activity and further comprises at least one of the following substitutions and/or substitution sets P2T/S3H/A49G/P168S/S233K/R276W; P2T/

S3X/A49G/S233X/I267X/R276W/L299X; P2T/C19L/E46C/A49G/F107Y/K132N/S233K/1267V/R276W; P2T/C19L/E46C/A49G/K132N/S233K/I267V/R276W; P2T/W20X/A49G/D63X/R276W; P2T/V24G/A49G; P2T/V24G/A49G/R276W; P2T/K36Q/A49G/G227D/R276W; P2T/E46C/A49G/F107Y/K132N/S233K/I267V/R276W; P2T/E46C/A49G/K132N/V164I/S233K/I267V/R276W; P2T/A49G; P2T/A49G/K52R/K152E/S233K/I267V/R276W; P2T/A49G/K52R/R206S/I267V/R276W; P2T/A49G/K52R/R276W; P2T/A49G/K68G/S261N/R276W/V318C; P2T/A49G/K68G/S261N/V318C; P2T/A49G/D86N/K132N/R276W; P2T/A49G/K132N; P2T/A49G/K132N/P168S/S233K/I267V/R276W; P2T/A49G/K132N/G227D/P252C/R276W; P2T/A49G/K132N/G227D/R276W; P2T/A49G/K132N/S233K/I267V/R276W; P2T/A49G/K132N/S233K/R276W; P2T/A49G/K132N/I267V/R276W; P2T/A49G/K132N/R276W; PT2/A49G/K152E; P2T/A49G/K152E/P168S/S233V/I267V/R276W; P2T/A49G/K152E/I267V/R276W; P2T/A49G/K152E/R276W; P2T/A49G/P168S/R206S/I267V/R276W; P2T/A49G/P168S/S233K/R276W; P2T/A49G/P168S/R276W; P2T/A49G/R206S/S233K/I267V/R276W; P2T/A49G/R206S; P2T/A49G/R206S/R276W; P2T/A49G/G227D/P252C/G264D/R276W; P2T/A49G/G227D/P252C/R276W; P2T/A49G/G227D/I267V/R276W; P2T/A49G/G227D/R276W; P2T/A49G/S233K/R276W; P2T/A49G/S233K/I267V/R276W; P2T/A49G/S233V/A246L/R276W/N302S; P2T/A49G/S233V/A246L/N302S; P2T/A49G/S233V/I267V/R276W; P2T/A49G/S233V/R276W; P2T/A49G/P252C/R276W; P2T/A49G/S261N; P2T/A49G/S261N/R276W; P2T/A49G/I267V/R276W; P2T/A49G/R276W; P2T/A46G/R276W/N302S; P2T/A49G/R276W/V318C; P2T/A49G/N302S; P2T/A49G/V319C; E46K/D47N; A49G/K132A; A49G/K132A/K152E; A49G/K132A/K152E/R276W; A49G/K132A/R206S; A49G/K132A/R276W; A49G/K132A/R206S/R276W; A49G/K132N/K152E/R276W; A49G/K132N/K152E/R276W/N302S; A49G/K132N/K152E/N302S; A49G/K132N/R206S/S233V/W276M/N302S; A49G/K132N/R206S/S233V/R276M/N302S; A49G/K152E; A49G/K152E/R276W; A49G/K152E; and A49G/R276W, in SEQ ID NO:2.

* * * * *

SEQUENCE LISTING

```
<160> NUMBER OF SEQ ID NOS: 59

<210> SEQ ID NO 1
<211> LENGTH: 960
<212> TYPE: DNA
<213> ORGANISM: Pichia stipitis

<400> SEQUENCE: 1

atgccttcta ttaagttgaa ctctggttac gacatgccag ccgtcggttt cggctgttgg      60

aaagtcgacg tcgacacctg ttctgaacag atctaccgtg ctatcaagac cggttacaga     120

ttgttcgacg gtgccgaaga ttacgccaac gaaaagttag ttggtgccgg tgtcaagaag     180

gccattgacg aaggtatcgt caagcgtgaa gacttgttcc ttacctccaa gttgtggaac     240

aactaccacc acccagacaa cgtcgaaaag gccttgaaca gaaccctttc tgacttgcaa     300

gttgactacg ttgacttgtt cttgatccac ttcccagtca ccttcaagtt cgttccatta     360

gaagaaaagt acccaccagg attctactgt ggtaagggtg acaacttcga ctacgaagat     420

gttccaattt tagagacctg gaaggctctt gaaaagttgg tcaaggccgg taagatcaga     480

tctatcggtg tttctaactt cccaggtgct ttgctcttgg acttgttgag aggtgctacc     540

atcaagccat ctgtcttgca agttgaacac cacccatact tgcaacaacc aagattgatc     600

gaattcgctc aatcccgtgg tattgctgtc accgcttact cttcgttcgg tcctcaatct     660

ttcgttgaat tgaaccaagg tagagctttg aacacttctc cattgttcga gaacgaaact     720

atcaaggcta tcgctgctaa gcacggtaag tctccagctc aagtcttgtt gagatggtct     780

tcccaaagag gcattgccat cattccaaag tccaacactg tcccaagatt gttggaaaac     840

aaggacgtca acagcttcga cttggacgaa caagatttcg ctgacattgc caagttggac     900

atcaacttga gattcaacga cccatgggac tgggacaaga ttcctatctt cgtctaataa     960


<210> SEQ ID NO 2
<211> LENGTH: 318
<212> TYPE: PRT
<213> ORGANISM: Pichia stipitis

<400> SEQUENCE: 2

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110
```

```
Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 3
<211> LENGTH: 960
<212> TYPE: DNA
<213> ORGANISM: Artificial sequence
<220> FEATURE:
<223> OTHER INFORMATION: Synthetic DNA which is codon optimized DNA sequence of xylose reductase from P. stipitis having sequence name XR.2

<400> SEQUENCE: 3

```
atgccctcca taaagctaaa ctctggttat gatatgcctg ccgttggatt cggttgttgg     60

aaagtagatg ttgatacctg ctcagaacag atttataggg ctattaaaac aggttacagg    120

ttgttcgacg gtgccgagga ctacgcgaat gagaagttag ttggagctgg tgttaagaag    180

gccatcgacg agggcattgt taagagggag gacctgttct taacgtctaa actgtggaat    240

aactatcacc acccagacaa tgttgaaaaa gccctgaata gaactttgag tgatttgcag    300

gtggattacg ttgacttgtt tctaatccat ttccccgtta ctttcaagtt cgtcccttta    360

gaggagaagt atccaccagg tttctattgt ggtaagggcg acaacttcga ctatgaagat    420

gttcctattc tggagacctg gaaggctctg gagaaactgg tcaaggcagg caaaataagg    480

tccataggcg tctctaactt cccaggagca ctactgcttg acttgttgag gggagctacc    540

atcaaacctt cagtcttgca agttgaacac cacccctatt tgcaacaacc caggctgata    600

gagtttgctc aatccagagg tatagctgtt actgcatact cttcctttgg acctcaatcc    660

ttcgtcgaac ttaaccaagg tagagcgttg aatacttccc ccttgttcga gaatgaaact    720

atcaaggcta ttgcggctaa gcacggtaag tcaccagctc aagtgttact tagatggtct    780

tcccaaaggg gtatcgcaat cattccaaag tctaacactg ttcccagatt gttggagaat    840
```

```
aaagatgtta attctttcga tttggacgaa caagactttg cagacatagc caaactagat    900

attaatctga gattcaatga tccctgggat tgggacaaga taccaatctt cgtttaataa    960


<210> SEQ ID NO 4
<211> LENGTH: 942
<212> TYPE: DNA
<213> ORGANISM: Artificial sequence
<220> FEATURE:
<223> OTHER INFORMATION: Synthetic DNA which is codon optimized DNA
      sequence of xylose reductase from P. stipitis having sequence
      name XR.3

<400> SEQUENCE: 4

atgccatcta ttaagttgaa ctctggttac gacatgccag ctgtcggttt cggttgtaag     60

gttgacgttg acacctgttc tgaacaaatt tacagagcta ttaagaccgg ttacagattg    120

ttcgacggtg ctgaagacta cgctaacgaa aagttggttg gtgctggtgt caagaaggct    180

attgacgaag gtattgtcaa gagagaagac ttgttcttga cctctaagtt gaacaactac    240

caccacccag acaacgtcga aaaggctttg aacagaacct tgtctgactt gcaagttgac    300

tacgttgact tgttcttgat tcacttccca gtcaccttca agttcgtccc attggaagaa    360

aagtacccac caggtttcta ctgtggtaag ggtgacaact tcgactacga agacgttcca    420

attttggaaa ccaaggcttt ggaaaagttg gttaaggctg gtaagattag gtctattggt    480

gtttctaact tcccaggtgc tttgttgttg gacttgttga gaggtgctac cattaagcca    540

tctgttttgc aagttgaaca ccacccatac ttgcaacaac caagattgat tgagttcgct    600

caatctaggg gtattgctgt caccgcttac tcttctttcg gtccacaatc tttcgtcgaa    660

ttgaaccaag gtagagcttt gaacacctct ccattgttcg aaaacgaaac cattaaggct    720

attgctgcta agcacggtaa gtctccagct caagtcttgt tgaggtcttc tcaaagaggt    780

attgctatta ttccaaagtc taacaccgtc ccaagattgt tggaaaacaa ggacgttaac    840

tctttcgact tggacgaaca agacttcgct gacattgcta agttggacat taacttgaga    900

ttcaacgacc cagacgacaa gattccaatt ttcgtttaat aa                       942


<210> SEQ ID NO 5
<211> LENGTH: 1095
<212> TYPE: DNA
<213> ORGANISM: Pichia stipitis

<400> SEQUENCE: 5

atgactgcta acccttcctt ggtgttgaac aagatcgacg acatttcgtt cgaaacttac     60

gatgccccag aaatctctga acctaccgat gtcctcgtcc aggtcaagaa aaccggtatc    120

tgtggttccg acatccactt ctacgcccat ggtagaatcg gtaacttcgt tttgaccaag    180

ccaatggtct tgggtcacga atccgccggt actgttgtcc aggttggtaa gggtgtcacc    240

tctcttaagg ttggtgacaa cgtcgctatc gaaccaggta ttccatccag attctccgac    300

gaatacaaga gcggtcacta caacttgtgt cctcacatgg ccttcgccgc tactcctaac    360

tccaaggaag gcgaaccaaa cccaccaggt accttatgta agtacttcaa gtcgccagaa    420

gacttcttgg tcaagttgcc agaccacgtc agcttggaac tcggtgctct tgttgagcca    480

ttgtctgttg gtgtccacgc ctctaagttg ggttccgttg ctttcggcga ctacgttgcc    540

gtctttggtg ctggtcctgt tggtcttttg gctgctgctg tcgccaagac cttcggtgct    600

aagggtgtca tcgtcgttga cattttcgac aacaagttga agatggccaa ggacattggt    660

gctgctactc acaccttcaa ctccaagacc ggtggttctg aagaattgat caaggctttc    720
```

```
ggtggtaacg tgccaaacgt cgttttggaa tgtactggtg ctgaaccttg tatcaagttg    780

ggtgttgacg ccattgcccc aggtggtcgt ttcgttcaag tcggtaacgc tgctggtcca    840

gtcagcttcc caatcaccgt tttcgccatg aaggaattga ctttgttcgg ttctttcaga    900

tacggattca acgactacaa gactgctgtt ggaatctttg acactaacta ccaaaacggt    960

agagaaaatg ctccaattga ctttgaacaa ttgatcaccc acagatacaa gttcaaggac   1020

gctattgaag cctacgactt ggtcagagcc ggtaagggtg ctgtcaagtg tctcattgac   1080

ggccctgagt aataa                                                     1095
```

<210> SEQ ID NO 6
<211> LENGTH: 363
<212> TYPE: PRT
<213> ORGANISM: Pichia stipitis

<400> SEQUENCE: 6

```
Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300
```

```
Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360
```

<210> SEQ ID NO 7
<211> LENGTH: 1095
<212> TYPE: DNA
<213> ORGANISM: Artificial sequence
<220> FEATURE:
<223> OTHER INFORMATION: Synthetic DNA which is codon optimized DNA sequence of xylitol dehydrogenase from P. stipitis having sequence name XD.2

<400> SEQUENCE: 7

```
atgaccgcta atccctctct tgttttgaat aagattgacg acatttcttt tgaaacttac     60

gatgctcccg aaattagcga acccacagac gttttagttc aagttaaaaa aactggtatc    120

tgcggttctg acatccactt ctacgctcat ggaaggatcg gcaacttcgt cttaacaaag    180

ccaatggttc tgggtcatga aagcgcgggt actgttgttc aagtcggtaa aggtgttact    240

tcactgaagg ttggtgataa cgtcgcaatc gagcccggta ttccatctag gttcagtgat    300

gagtacaaat ctggtcacta caacctgtgt ccacacatgg catttgctgc tactcccaat    360

tctaaagagg gtgaaccaaa cccaccagga actctatgta agtacttcaa atctccagaa    420

gacttcctgg ttaagttacc cgatcatgtt tctttggagt tgggtgcttt ggtcgagcca    480

ctatctgttg gggtccatgc tagtaaatta ggctccgttg catttggcga ttacgttgct    540

gtttttggtg ctggtccagt aggattactg gctgccgctg tcgctaagac atttggtgcc    600

aagggtgtga ttgtcgttga tatatttgac aacaagctga agatggccaa agacataggt    660

gccgctacac ataccttcaa ctccaagacg ggaggtagtg aagaattgat caaagccttc    720

ggtggtaatg taccaaatgt tgtcttggaa tgtactgggg ctgaaccatg tattaagcta    780

ggtgttgatg ccatcgcacc aggtggtaga ttcgtgcaag ttggtaatgc tgctggtccc    840

gtgtcctttc ccataacagt gttcgctatg aaagaactta ctttgtttgg ttcatttcgt    900

tatggtttca acgactataa gacagccgtg ggtatctttg atactaacta ccagaacggt    960

agagagaatg ctcccattga ctttgaacag cttatcacgc acagatacaa attcaaagac   1020

gccattgaag cctacgacct agtaagagca ggtaaagggg ctgtcaagtg tttgattgat   1080

ggtccagaat aataa                                                    1095
```

<210> SEQ ID NO 8
<211> LENGTH: 1095
<212> TYPE: DNA
<213> ORGANISM: Artificial sequence
<220> FEATURE:
<223> OTHER INFORMATION: Synthetic DNA which is codon optimized DNA sequence of xylitol dehydrogenase from P. stipitis having sequence name XD.3

<400> SEQUENCE: 8

```
atgaccgcta acccatcttt ggtcttgaac aagattgacg acatttcttt cgaaacctac     60

gacgctccag aaatttctga accaaccgac gttttggttc aagtcaagaa gaccggtatt    120
```

```
tgtggttctg acattcactt ctacgctcac ggtagaattg gtaacttcgt cttgaccaag    180

ccaatggtct tgggtcacga atctgctggt accgttgttc aagtcggtaa gggtgtcacc    240

tctttgaagg tcggtgacaa cgtcgctatt gaaccaggta ttccaagtag attctctgac    300

gaatacaagt ctggtcacta caacttgtgt ccacacatgg ctttcgctgc taccccaaac    360

tctaaggaag gtgaaccaaa cccaccaggt accttgtgta agtacttcaa gtctccagaa    420

gacttcttgg ttaagttgcc agaccacgtt tctttggaat tgggtgcttt ggttgaacca    480

ttgtctgttg gtgttcacgc ttctaagttg ggttctgttg ctttcggtga ctacgttgct    540

gttttcggtg ctggtccagt tggtttgttg gctgctgctg ttgctaagac cttcggtgct    600

aagggtgtca ttgtcgttga cattttcgac aacaagttga agatggctaa ggacattggt    660

gctgctaccc acaccttcaa ctctaagacc ggtggttctg aagaattgat taaggctttc    720

ggtggtaacg tcccaaacgt cgtcttggaa tgtaccggtg ctgaaccatg tattaagttg    780

ggtgttgacg ctattgctcc aggtggtaga ttcgtccaag ttggtaacgc tgctggtcca    840

gtttctttcc caattaccgt tttcgctatg aaggaattga ccttgttcgg ttctttcaga    900

tacggtttca acgactacaa gaccgctgtt ggtattttcg acaccaacta ccaaaacggt    960

agagaaaacg ctccaattga cttcgaacaa ttgattaccc acagatacaa gttcaaggac   1020

gctattgaag cttacgactt ggttagagct ggtaagggtg ctgttaagtg tttgattgac   1080

ggtccagaat aataa                                                    1095
```

<210> SEQ ID NO 9
<211> LENGTH: 1803
<212> TYPE: DNA
<213> ORGANISM: Saccharomyces cerevisiae

<400> SEQUENCE: 9

```
atgttgtgtt cagtaattca gagacagaca agagaggttt ccaacacaat gtctttagac     60

tcatactatc ttgggtttga tctttcgacc caacaactga aatgtctcgc cattaaccag    120

gacctaaaaa ttgtccattc agaaacagtg gaatttgaaa aggatcttcc gcattatcac    180

acaaagaagg gtgtctatat acacggcgac actatcgaat gtcccgtagc catgtggtta    240

gaggctctag atctggttct ctcgaaatat cgcgaggcta aatttccatt gaacaaagtt    300

atggccgtct cagggtcctg ccagcagcac gggtctgtct actggtcctc ccaagccgaa    360

tctctgttag agcaattgaa taagaaaccg gaaaaagatt tattgcacta cgtgagctct    420

gtagcatttg caaggcaaac cgcccccaat tggcaagacc acagtactgc aaagcaatgt    480

caagagtttg aagagtgcat aggtgggcct gaaaaaatgg ctcaattaac agggtccaga    540

gcccatttta gatttactgg tcctcaaatt ctgaaaattg cacaattaga accagaagct    600

tacgaaaaaa caaagaccat ttctttagtg tctaattttt tgacttctat cttagtgggc    660

catcttgttg aattagagga ggcagatgcc tgtggtatga acctttatga tatacgtgaa    720

agaaaattca gtgatgagct actacatcta attgatagtt cttctaagga taaaactatc    780

agacaaaaat taatgagagc acccatgaaa aatttgatag cgggtaccat ctgtaaatat    840

tttattgaga agtacggttt caatacaaac tgcaaggtct ctcccatgac tggggataat    900

ttagccacta tatgttcttt acccctgcgg aagaatgacg ttctcgtttc cctaggaaca    960

agtactacag ttcttctggt caccgataag tatcacccct ctccgaacta tcatcttttc   1020

attcatccaa ctctgccaaa ccattatatg ggtatgattt gttattgtaa tggttctttg   1080

gcaagggaga ggataagaga cgagttaaac aaagaacggg aaaataatta tgagaagact   1140
```

```
aacgattgga ctctttttaa tcaagctgtg ctagatgact cagaaagtag tgaaaatgaa   1200

ttaggtgtat attttcctct gggggagatc gttcctagcg taaaagccat aaacaaaagg   1260

gttatcttca atccaaaaac gggtatgatt gaaagagagg tggccaagtt caaagacaag   1320

aggcacgatg ccaaaaatat tgtagaatca caggctttaa gttgcagggt aagaatatct   1380

cccctgcttt cggattcaaa cgcaagctca caacagagac tgaacgaaga tacaatcgtg   1440

aagtttgatt acgatgaatc tccgctgcgg gactacctaa ataaaaggcc agaaaggact   1500

tttttgtag gtggggcttc taaaaacgat gctattgtga agaagtttgc tcaagtcatt   1560

ggtgctacaa agggtaattt taggctagaa acaccaaact catgtgccct tggtggttgt   1620

tataaggcca tgtggtcatt gttatatgac tctaataaaa ttgcagttcc ttttgataaa   1680

tttctgaatg acaattttcc atggcatgta atggaaagca tatccgatgt ggataatgaa   1740

aattgggatc gctataattc caagattgtc cccttaagcg aactggaaaa gactctcatc   1800

taa                                                                 1803
```

<210> SEQ ID NO 10
<211> LENGTH: 600
<212> TYPE: PRT
<213> ORGANISM: Saccharomyces cerevisiae

<400> SEQUENCE: 10

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
```

```
                245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
        275                 280                 285

Thr Asn Cys Lys Val Ser Pro Met Thr Gly Asp Asn Leu Ala Thr Ile
    290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
        355                 360                 365

Leu Asn Lys Glu Arg Glu Asn Asn Tyr Glu Lys Thr Asn Asp Trp Thr
    370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
            420                 425                 430

Glu Val Ala Lys Phe Lys Asp Lys Arg His Asp Ala Lys Asn Ile Val
        435                 440                 445

Glu Ser Gln Ala Leu Ser Cys Arg Val Arg Ile Ser Pro Leu Leu Ser
    450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
        515                 520                 525

Leu Glu Thr Pro Asn Ser Cys Ala Leu Gly Gly Cys Tyr Lys Ala Met
    530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
        595                 600
```

<210> SEQ ID NO 11
<211> LENGTH: 1806
<212> TYPE: DNA
<213> ORGANISM: Artificial sequence
<220> FEATURE:
<223> OTHER INFORMATION: Synthetic DNA which is codon optimized DNA sequence of xylulokinase from *S. cerevisiae* having sequence name XK.2

<400> SEQUENCE: 11

```
atgctgtgct ccgttataca aaggcaaaca agagaagtat ccaacactat gtctttagat      60
agttattatc taggattcga tttaagtaca caacaattga aatgtcttgc tataaaccag     120
gatctaaaga tcgtccattc cgaaactgtc gagttcgaga aggacttacc acattatcac     180
accaagaaag gcgtctacat tcatggtgac accatcgaat gcccagttgc tatgtggtta     240
gaagccctgg atcttgtcct gtccaaatat agggaggcaa agttcccact gaacaaggtc     300
atggctgttt ccggttcttg tcagcagcat ggctccgtct actggtcatc acaggctgaa     360
tctctgttag aacaactgaa caagaagcca gagaaggacc tgttacacta cgtctcctct     420
gttgcatttg ccagacaaac tgctcctaat tggcaagacc attccactgc taaacaatgt     480
caggagttcg aagagtgtat tggtggacca gagaaaatgg cccagttaac tggttcccgt     540
gctcatttca ggttcacagg cccacaaatc ctgaagattg ctcagttaga accagaggct     600
tatgaaaaga ctaagaccat ctctttggtc tctaatttct taacttccat tctggttggt     660
cacttggtcg aactggaaga agctgatgcg tgtggtatga acctgtacga catccgtgag     720
aggaagttct ctgacgaact gctgcatctt atcgactcct cctctaagga caagaccatc     780
aggcagaaac tgatgagggc accaatgaag aacctgattg ccggtactat ttgcaagtac     840
ttcatcgaaa agtatggctt caacaccaac tgcaaagtct cccctatgac tggcgataac     900
ctagccacca tttgtagctt gcccttaaga aaaaacgatg ttcttgtgtc tttgggtact     960
tccacaaccg tcttgttggt taccgacaaa tatcaccctt caccaaacta ccacctgttc    1020
atccacccga cgttgcctaa ccactacatg ggcatgatct gctactgcaa tggcagttta    1080
gcaagggaaa ggataaggga cgagttgaac aaggagaggg agaacaacta cgagaagacc    1140
aacgattgga ccctgttcaa ccaagctgtc ctggatgata gcgaatcctc cgagaatgaa    1200
ctgggcgttt actttccact aggcgagatc gttccatctg tcaaggccat caacaagaga    1260
gtaatcttca accccaagac tggcatgatc gaaagggaag tcgccaagtt caaggacaag    1320
agacatgacg ccaagaacat cgttgaatct caagccttat cttgccgtgt taggatttct    1380
cccctactaa gcgactccaa tgcttcttcc cagcaacgtt tgaacgagga tacgattgtt    1440
aaattcgact acgacgagag tccattgaga gactacttga acaaacgtcc tgagaggaca    1500
ttctttgttg gtggcgcatc caagaacgat gctattgtta agaagtttgc tcaggtcata    1560
ggagcaacca aaggtaactt tcgtttagaa actccaaact catgcgcttt aggtggttgc    1620
tacaaggcta tgtggtcttt gttgtatgat agcaataaaa tcgctgttcc tttcgacaag    1680
ttcctaaacg ataacttccc ttggcacgtc atggaatcca tcagcgatgt agacaacgag    1740
aattgggata gatacaattc taaaatagtt ccccttgtctg agttagagaa gaccttgatt   1800
taataa                                                               1806
```

<210> SEQ ID NO 12
<211> LENGTH: 1785
<212> TYPE: DNA
<213> ORGANISM: Artificial sequence
<220> FEATURE:
<223> OTHER INFORMATION: Synthetic DNA which is codon optimized DNA sequence of xylulokinase from S. cerevisiae having sequence name XK.3

<400> SEQUENCE: 12

```
atgttgtgtt ctgtcattca aagacaaacc agagaagttt ctaacaccat gtctttggac      60
tcttactact tgggtttcga cttgtctacc caacaattga agtgtttggc tattaaccaa     120
```

```
gacttgaaga ttgtccactc tgaaaccgtt gagttcgaaa aggacttgcc acactaccac    180

accaagaagg gtgtctacat tcacggtgac accattgaat gtccagtcgc tatgttggaa    240

gctttggact tggttttgtc taagtacaga gaagctaagt tcccattgaa caaggtcatg    300

gctgtctctg gttcttgtca acaacacggt tctgtctact cttctcaagc tgaatctttg    360

ttggaacaat tgaacaagaa gccagaaaag gacttgttgc actacgtctc ttctgtcgct    420

ttcgctagac aaaccgctcc aaaccaagac cactctaccg ctaagcaatg tcaagagttc    480

gaagaatgta ttggtggtcc agaaaagatg gctcaattga ccggtagtag agcacacttc    540

agattcaccg gtccacaaat tttgaagatt gctcaattgg aaccagaagc ttacgaaaag    600

accaagacca tttctttggt ctctaacttc ttgacctcta ttttggtcgg tcacttggtc    660

gaattggaag aagctgacgc ttgtggtatg aacttgtacg acattagaga aagaaagttc    720

tctgacgaat tgttgcactt gattgactct tcttctaagg acaagaccat tagacaaaag    780

ttgatgaggg ctccaatgaa gaacttgatt gctggtacca tttgtaagta cttcattgaa    840

aagtacggtt tcaacaccaa ctgtaaggtc tctccaatga ccggtgacaa cttggctacc    900

atttgttctt tgccattgag aaagaacgac gttttggttt ctttgggtac ctctaccacc    960

gtcttgttgg ttaccgacaa gtaccaccca tctccaaact accacttgtt cattcaccca   1020

accttgccaa accactacat gggtatgatt tgttactgta acggttcttt ggctagagaa   1080

agaattagag acgaattgaa caaggaaaga gaaaacaact acgaaaagac caacgacacc   1140

ttgttcaacc aagctgtttt ggacgactct gaatcttctg aaaacgaatt gggtgtctac   1200

ttcccattgg gtgaaattgt tccatctgtc aaggctatta acaagagagt cattttcaac   1260

ccaaagaccg gtatgattga aagagaagtc gctaagttca aggacaagag acacgacgct   1320

aagaacattg tcgaatctca agctttgtct tgtagagtta gaatttctcc attgttgtct   1380

gactctaacg cttcttctca acaaagattg aacgaagaca ccattgtcaa gttcgactac   1440

gacgaatctc cattgagaga ctacttgaac aagagaccag aaagaacctt cttcgttggt   1500

ggtgcttcta agaacgacgc tattgttaag aagttcgctc aagtcattgg tgctaccaag   1560

ggtaacttca gattggaaac cccaaactct tgtgctttgg gtggttgtta caaggctatg   1620

tctttgttgt acgactctaa caagattgct gttccattcg acaagttctt gaacgacaac   1680

ttcccacacg tcatggaatc tatttctgac gttgacaacg aaaacgacag atacaactct   1740

aagattgttc cattgtctga attggaaaag accttgattt aataa                   1785
```

<210> SEQ ID NO 13
<211> LENGTH: 14
<212> TYPE: DNA
<213> ORGANISM: Artificial sequence
<220> FEATURE:
<223> OTHER INFORMATION: Synthetic DNA 5' flanking sequence to introduce specific restriction enzyme sites

<400> SEQUENCE: 13

```
ggatcccaaa caaa                                                       14
```

<210> SEQ ID NO 14
<211> LENGTH: 6
<212> TYPE: DNA
<213> ORGANISM: Artificial sequence
<220> FEATURE:
<223> OTHER INFORMATION: Synthetic DNA 3' flanking sequence to introduce specific restriction enzyme sites

<400> SEQUENCE: 14

```
catatg                                                                  6


<210> SEQ ID NO 15
<211> LENGTH: 14
<212> TYPE: DNA
<213> ORGANISM: Artificial sequence
<220> FEATURE:
<223> OTHER INFORMATION: Synthetic DNA 5' flanking sequence to introduce
      specific restriction enzyme sites

<400> SEQUENCE: 15

actagtcaaa caaa                                                        14


<210> SEQ ID NO 16
<211> LENGTH: 6
<212> TYPE: DNA
<213> ORGANISM: Artificial sequence
<220> FEATURE:
<223> OTHER INFORMATION: Synthetic DNA 3' flanking sequence to introduce
      specific restriction enzyme sites

<400> SEQUENCE: 16

gacgtc                                                                  6


<210> SEQ ID NO 17
<211> LENGTH: 16
<212> TYPE: DNA
<213> ORGANISM: Artificial sequence
<220> FEATURE:
<223> OTHER INFORMATION: Synthetic DNA 5' flanking sequence to introduce
      specific restriction enzyme sites

<400> SEQUENCE: 17

gcggccgcca aacaaa                                                      16


<210> SEQ ID NO 18
<211> LENGTH: 6
<212> TYPE: DNA
<213> ORGANISM: Artificial sequence
<220> FEATURE:
<223> OTHER INFORMATION: Synthetic DNA 3' flanking sequence to introduce
      specific restriction enzyme sites

<400> SEQUENCE: 18

ctcgag                                                                  6


<210> SEQ ID NO 19
<211> LENGTH: 88
<212> TYPE: DNA
<213> ORGANISM: Artificial sequence
<220> FEATURE:
<223> OTHER INFORMATION: Synthetic DNA to introduce a new multiple
      cloning site

<400> SEQUENCE: 19

gagctcacgg atccgtcata tgctagatct ctgaattctt actagttcga cgtctaccta      60

ggcagtcgac acgcggccgc ttctcgag                                         88


<210> SEQ ID NO 20
<211> LENGTH: 60
<212> TYPE: DNA
<213> ORGANISM: Artificial sequence
<220> FEATURE:
<223> OTHER INFORMATION: Synthetic DNA primer

<400> SEQUENCE: 20
```

gcatagcaat ctaatctaag ttttggatcc gtcatatggc ggatctctta tgtctttacg 60

<210> SEQ ID NO 21
<211> LENGTH: 54
<212> TYPE: DNA
<213> ORGANISM: Artificial sequence
<220> FEATURE:
<223> OTHER INFORMATION: Synthetic DNA primer

<400> SEQUENCE: 21
ttgtatgtac ctgtctgaat tcagagatct agccctgaga aactatatga gggt 54

<210> SEQ ID NO 22
<211> LENGTH: 54
<212> TYPE: DNA
<213> ORGANISM: Artificial sequence
<220> FEATURE:
<223> OTHER INFORMATION: Synthetic DNA primer

<400> SEQUENCE: 22
accctcatat agtttctcag ggctagatct ctgaattcag acaggtacat acaa 54

<210> SEQ ID NO 23
<211> LENGTH: 62
<212> TYPE: DNA
<213> ORGANISM: Artificial sequence
<220> FEATURE:
<223> OTHER INFORMATION: Synthetic DNA primer

<400> SEQUENCE: 23
tcataaatca taagaaattc gcgacgtcga actagttgta tatgagatag ttgattgtat 60
gc 62

<210> SEQ ID NO 24
<211> LENGTH: 62
<212> TYPE: DNA
<213> ORGANISM: Artificial sequence
<220> FEATURE:
<223> OTHER INFORMATION: Synthetic DNA primer

<400> SEQUENCE: 24
gcatacaatc aactatctca tatacaacta gttcgacgtc gcgaatttct tatgatttat 60
ga 62

<210> SEQ ID NO 25
<211> LENGTH: 47
<212> TYPE: DNA
<213> ORGANISM: Artificial sequence
<220> FEATURE:
<223> OTHER INFORMATION: Synthetic DNA primer

<400> SEQUENCE: 25
tgataaactc gaagtcgact gcctaggcat gccggtagag gtgtggt 47

<210> SEQ ID NO 26
<211> LENGTH: 47
<212> TYPE: DNA
<213> ORGANISM: Artificial sequence
<220> FEATURE:
<223> OTHER INFORMATION: Synthetic DNA primer

<400> SEQUENCE: 26
accacacctc taccggcatg cctaggcagt cgacttcgag tttatca 47

<210> SEQ ID NO 27
<211> LENGTH: 58
<212> TYPE: DNA
<213> ORGANISM: Artificial sequence
<220> FEATURE:
<223> OTHER INFORMATION: Synthetic DNA primer

<400> SEQUENCE: 27
gcgtgacata actaattaca tgactcgaga agcggccgct ttgtttgttt atgtgtgt 58

<210> SEQ ID NO 28
<211> LENGTH: 6
<212> TYPE: DNA
<213> ORGANISM: Artificial sequence
<220> FEATURE:
<223> OTHER INFORMATION: Synthetic DNA of sequence within the ADH2 terminator

<400> SEQUENCE: 28 gacgtc 6

<210> SEQ ID NO 29
<211> LENGTH: 6
<212> TYPE: DNA
<213> ORGANISM: Artificial sequence
<220> FEATURE:
<223> OTHER INFORMATION: Synthetic DNA

<400> SEQUENCE: 29 gatgtc 6

<210> SEQ ID NO 30
<211> LENGTH: 67
<212> TYPE: DNA
<213> ORGANISM: Artificial sequence
<220> FEATURE:
<223> OTHER INFORMATION: Synthetic DNA primer

<400> SEQUENCE: 30
cttgctcatt agaaagaaag catagcaatc taatctaagt tttggatccc aaacaaaatg 60
ccctcca 67

<210> SEQ ID NO 31
<211> LENGTH: 61
<212> TYPE: DNA
<213> ORGANISM: Artificial sequence
<220> FEATURE:
<223> OTHER INFORMATION: Synthetic DNA primer

<400> SEQUENCE: 31
ctataaatcg taaagacata agagatccgc catatgttat taaacgaaga ttggtatctt 60
g 61

<210> SEQ ID NO 32
<211> LENGTH: 61
<212> TYPE: DNA
<213> ORGANISM: Artificial sequence
<220> FEATURE:
<223> OTHER INFORMATION: Synthetic DNA primer

<400> SEQUENCE: 32
caagatacca atcttcgttt aataacatat ggcggatctc ttatgtcttt acgatttata 60
g 61

<210> SEQ ID NO 33
<211> LENGTH: 63
<212> TYPE: DNA
<213> ORGANISM: Artificial sequence
<220> FEATURE:
<223> OTHER INFORMATION: Synthetic DNA primer

<400> SEQUENCE: 33
gagggattag cggtcatttt gtttgactag ttgtatatga gatagttgat tgtatgcttg 60
gta 63

<210> SEQ ID NO 34
<211> LENGTH: 63
<212> TYPE: DNA
<213> ORGANISM: Artificial sequence
<220> FEATURE:
<223> OTHER INFORMATION: Synthetic DNA primer

<400> SEQUENCE: 34
taccaagcat acaatcaact atctcatata caactagtca aacaaaatga ccgctaatcc 60
ctc 63

<210> SEQ ID NO 35
<211> LENGTH: 60
<212> TYPE: DNA
<213> ORGANISM: Artificial sequence
<220> FEATURE:
<223> OTHER INFORMATION: Synthetic DNA primer

<400> SEQUENCE: 35
taataaaaat cataaatcat aagaaattcg cgacgtctta ttattctgga ccatcaatca 60

<210> SEQ ID NO 36
<211> LENGTH: 60
<212> TYPE: DNA
<213> ORGANISM: Artificial sequence
<220> FEATURE:
<223> OTHER INFORMATION: Synthetic DNA primer

<400> SEQUENCE: 36
tgattgatgg tccagaataa taagacgtcg cgaatttctt atgatttatg atttttatta 60

<210> SEQ ID NO 37
<211> LENGTH: 61
<212> TYPE: DNA
<213> ORGANISM: Artificial sequence
<220> FEATURE:
<223> OTHER INFORMATION: Synthetic DNA primer

<400> SEQUENCE: 37
tttgtataac ggagcacagc attttgtttg gcggccgctt tgtttgttta tgtgtgttta 60
t 61

<210> SEQ ID NO 38
<211> LENGTH: 61
<212> TYPE: DNA
<213> ORGANISM: Artificial sequence
<220> FEATURE:
<223> OTHER INFORMATION: Synthetic DNA primer

<400> SEQUENCE: 38
ataaacacac ataaacaaac aaagcggccg ccaaacaaaa tgctgtgctc cgttatacaa 60
a 61

<210> SEQ ID NO 39
<211> LENGTH: 70
<212> TYPE: DNA
<213> ORGANISM: Artificial sequence
<220> FEATURE:
<223> OTHER INFORMATION: Synthetic DNA primer

<400> SEQUENCE: 39

```
ggggagggcg tgaatgtaag cgtgacataa ctaattacat gactcgagtt attaaatcaa     60

ggtcttctct                                                           70
```

<210> SEQ ID NO 40
<211> LENGTH: 957
<212> TYPE: DNA
<213> ORGANISM: Artificial sequence
<220> FEATURE:
<223> OTHER INFORMATION: Synthetic DNA

<400> SEQUENCE: 40

```
atgccttcta ttaagttgaa ctctggttac gacatgccag ccgtcggttt cggctgttgg     60

aaagttgacg ttgacacctg ttctgaacag gtctaccgtg ctatcaagac cggttacaga    120

ttgttcgacg gtgccgaaga ttacgccaac gaaaagttag ttggtgccgg tgtcaagaag    180

gccattgacg aaggtatcgt caagcgtgaa gacttgttcc ttacctccaa gttgtggaac    240

aactaccacc acccagacaa cgtcgaaaag gccttgaaca gaaccctttc tgacttgcaa    300

gttgactacg ttgacttgtt cttgatccac ttcccagtca ccttcaagtt cgttccatta    360

gaagaaaagt acccaccagg attctactgt ggtaagggtg acaacttcga ctacgaagat    420

gttccaattt tagagacctg gaaggctctt gaaaagttgg tcaaggccgg taagatcagg    480

tctatcggtg tttctaactt cccaggtgct ttgctcttgg acttgttgag aggtgctacc    540

atcaagccat ctgtcttgca agttgaacac cacccatact tgcaacaacc aagattgatc    600

gagttcgctc aatcccgtgg tattgctgtc accgcttact cttcgttcgg tcctcaatct    660

ttcgttgaat tgaaccaagg tagagctttg aacacttctc cattgttcga gaacgaaact    720

atcaaggcta tcgctgctaa gcacggtaag tctccagctc aagtcttgtt gagatggtct    780

tcccaaagag gcattgccat cattccaaag tccaacactg tcccatggtt gttggaaaac    840

aaggatgtca acagcttcga cttggacgaa caagatttcg ctgacattgc caagttggac    900

atcaacttga gattcaacga cccatgggac tgggacaaga ttcctatctt cgtctaa       957
```

<210> SEQ ID NO 41
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 41

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60
```

```
Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 42
<211> LENGTH: 957
<212> TYPE: DNA
<213> ORGANISM: Artificial sequence
<220> FEATURE:
<223> OTHER INFORMATION: Synthetic DNA

<400> SEQUENCE: 42

```
atgacctcta ttaagttgaa ctctggttac gacatgccag ccgtcggttt cggctgttgg     60

aaagttgacg ttgacacctg ttctgaacag gtctaccgtg ctatcaagac cggttacaga    120

ttgttcgacg gtgccgaaga ttacggcaac gaaaagttag ttggtgccgg tgtcaagaag    180

gccattgacg aaggtatcgt caagcgtgaa gacttgttcc ttacctccaa gttgtggaac    240

aactaccacc acccagacaa cgtcgaaaag gccttgaaca gaaccctttc tgacttgcaa    300

gttgactacg ttgacttgtt cttgatccac ttcccagtca ccttcaagtt cgttccatta    360

gaagaaaagt acccaccagg attctactgt ggtaagggtg acaacttcga ctacgaagat    420

gttccaattt tagagacctg gaaggctctt gaaaagttgg tcaaggccgg taagatcagg    480

tctatcggtg tttctaactt cccaggtgct ttgctcttgg acttgttgag aggtgctacc    540

atcaagccat ctgtcttgca agttgaacac cacccatact tgcaacaacc aagattgatc    600

gagttcgctc aatcccgtgg tattgctgtc accgcttact cttcgttcgg tcctcaatct    660
```

```
ttcgttgaat tgaaccaagg tagagctttg aacacttctc cattgttcga gaacgaaact    720

atcaaggcta tcgctgctaa gcacggtaag tctccagctc aagtcttgtt gagatggtct    780

tcccaaagag gcattgccat cattccaaag tccaacactg tcccatggtt gttggaaaac    840

aaggatgtca acagcttcga cttggacgaa caagatttcg ctgacattgc caagttggac    900

atcaacttga gattcaacga cccatgggac tgggacaaga ttcctatctt cgtctaa       957
```

```
<210> SEQ ID NO 43
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 43

Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
```

305 310 315

<210> SEQ ID NO 44
<211> LENGTH: 957
<212> TYPE: DNA
<213> ORGANISM: Artificial sequence
<220> FEATURE:
<223> OTHER INFORMATION: Synthetic DNA

<400> SEQUENCE: 44

```
atgacctcta ttaagttgaa ctctggttac gacatgccag ccgtcggttt cggctgttgg      60

aaagttgacg ttgacacctg ttctgaacag gtctaccgag ctatcaagac cggttacaga     120

ttgttcgacg gtgccgaaga ttacggcaac gaaaaattag ttggtgccgg tgtcaagaag     180

gccattgacg aaggtatcgt caagcgtgaa gacttgttcc ttacctccaa gttgtggaac     240

aactaccacc acccagacaa cgtcgaaaag gccttgaaca gaaccctttc tgacttgcaa     300

gttgactacg ttgacttgtt cttgatccac ttcccagtca ccttcaagtt cgttccatta     360

gaagaaaagt acccaccagg attctactgt ggtaacggtg acaacttcga ctacgaagat     420

gttccaattt tagagacctg gaaggctctt gaaaagttgg tcaaggccgg taagatcagg     480

tctatcggtg tttctaactt cccaggtgct ttgctcttgg acttgttgag aggtgctacc     540

atcaagccat ctgtcttgca agttgaacac cacccatact tgcaacaacc aagattgatc     600

gagttcgctc aatcccgtgg tattgctgtc accgcttact cttcgttcgg tcctcaatct     660

ttcgttgaat tgaaccaagg tagagctttg aacactaagc cattgttcga gaacgaaact     720

atcaaggcta tcgctgctaa gcacggcaag agcccagctc aagtcttgtt gagatggtct     780

tcccaaagag gcattgccgt tattccaaag tccaacactg tcccatggtt gttggaaaac     840

aaggatgtca acagcttcga cttggacgaa caagatttcg ctgacattgc caagttggac     900

atcaacttga gattcaacga cccatgggac tgggacaaga ttcctatctt cgtctaa        957
```

<210> SEQ ID NO 45
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 45

```
Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Asn Gly Asp Asn Phe Asp Tyr Glu Asp Val Pro Ile Leu
```

```
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Lys Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Val Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315


<210> SEQ ID NO 46
<211> LENGTH: 957
<212> TYPE: DNA
<213> ORGANISM: Artificial sequence
<220> FEATURE:
<223> OTHER INFORMATION: Synthetic DNA

<400> SEQUENCE: 46

atgccttcta ttaagttgaa ctctggttac gacatgccag ccgtcggttt cggctgttgg      60

aaagttgacg ttgacacctg ttctgaacag gtctaccgtg ctatcaagac cggttacaga     120

ttgttcgacg gtgccgaaga ttacgccaac gaaaagttag ttggtgccgg tgtcaagaag     180

gccattgacg aaggtatcgt caagcgtgaa gacttgttcc ttacctccaa gttgtggaac     240

aactaccacc acccagacaa cgtcgaaaag gccttgaaca gaaccctttc tgacttgcaa     300

gttgactacg ttgacttgtt cttgatccac ttcccagtca ccttcaagtt cgttccatta     360

gaagaaaagt acccaccagg attctactgt ggtaagggtg acaacttcga ctacgaagat     420

gttccaattt tagagacctg gaaggctctt gaaaagttgg tcaaggccgg taagatcagg     480

tctatcggtg tttctaactt cccaggtgct ttgctcttgg acttgttgag aggtgctacc     540

atcaagccat ctgtcttgca agttgaacac cacccatact tgcaacaacc aagattgatc     600

gagttcgctc aatcccgtgg tattgctgtc accgcttact cttcgttcgg tcctcaatct     660

ttcgttgaat tgaaccaagg tagagctttg aacacttctc cattgttcga gaacgaaact     720

atcaaggcta tcgctgctaa gcacggtaag tctccagctc aagtcttgtt gagatggtct     780

tcccaaagag gcattgccat cattccaaag agcaatactg tcccattctt gttggaaaac     840

aaggatgtca acagcttcga cttggacgaa caagatttcg ctgacattgc caagttggac     900

atcaacttga gattcaacga cccatgggac tgggacaaga ttcctatctt cgtctaa        957


<210> SEQ ID NO 47
```

```
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 47

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Phe Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315


<210> SEQ ID NO 48
<211> LENGTH: 1092
<212> TYPE: DNA
<213> ORGANISM: Artificial sequence
<220> FEATURE:
<223> OTHER INFORMATION: Synthetic DNA

<400> SEQUENCE: 48

atgaccgcta atccctctct tgttttgaat aagattgacg acatttcttt tgaaacttac      60
```

```
gatgctcccg aaattagcga acccacagac gttttagttc aagttaaaaa aactggtatc    120

tgcggttctg acatccactt ctacgctcat ggaaggatcg gcaacttcgt cttaacaaag    180

ccaatggttc tgggtcatga aagcgcgggt actgttgttc aagtcggtaa aggtgttact    240

tcactgaagg ttggtgataa cgtcgcaatc gagcccggta ttccatctag gttcagtgat    300

gagtacaaat ctggtcacta caacctgtgt ccacacatgg catttgctgc tactcccaat    360

tctaaagagg gtgaaccaaa cccaccagga actctatgta agtacttcaa atctccagaa    420

gacttcctgg ttaagttacc cgatcatgtt tctttggagt tgggtgcttt ggtcgagcca    480

ctatctgttg gggtccatgc tagtaaatta ggctccgttg catttggcga ttacgttgct    540

gtttttggtg ctggtccagt aggattactg gctgccgctg tcgctaagac atttggtgcc    600

aagggtgtga ttgtcgttga tatatctgac aagaagctga agatggccaa agacataggt    660

gccgctacac ataccttcaa ctccaagacg ggaggtagtg aagaattgat caaagccttc    720

ggtggtaatg taccaaatgt tgtcttggaa tgtactgggg ctgaaccatg tattaagcta    780

ggtgttgatg ccatcgcacc aggtggtaga ttcgtgcaag ttggtaatgc tgctggtccc    840

gtgtcctttc ccataacagt gttcgctatg aaagaactta ctttgtttgg ttcatttcgt    900

tatggtttca acgactataa gacagccgtg ggtatctttg atactaacta ccagaacggt    960

agagagaatg ctcccattga ctttgaacag cttatcacgc acagatacaa attcaaagac   1020

gccattgaag cctacgacct agtaagagca ggtaaagggg ctgtcaagtg tttgattgat   1080

ggtccagaat aa                                                       1092
```

```
<210> SEQ ID NO 49
<211> LENGTH: 363
<212> TYPE: PRT
<213> ORGANISM: Artificial sequence
<220> FEATURE:
<223> OTHER INFORMATION: Synthetic polypeptide

<400> SEQUENCE: 49

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175
```

```
Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Ser Asp Lys Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360
```

<210> SEQ ID NO 50
<211> LENGTH: 957
<212> TYPE: DNA
<213> ORGANISM: Artificial sequence
<220> FEATURE:
<223> OTHER INFORMATION: Synthetic DNA

<400> SEQUENCE: 50

```
atgccttcta ttaagttgaa ctctggttac gacatgccag ccgtcggttt cggctgttgg     60

aaagttgacg ttgacacctg ttctgaacag gtctaccgtg ctatcaagac cggttacaga    120

ttgttcgacg gtgccgaaga ttacgccaac gaaaagttag ttggtgccgg tgtcaagaag    180

gccattgacg aaggtatcgt caagcgtgaa gacttgttcc ttacctccaa gttgtggaac    240

aactaccacc acccagacaa cgtcgaaaag gccttgaaca gaacccttc tgacttgcaa     300

gttgactacg ttgacttgtt cttgatccac ttcccagtca ccttcaagtt cgttccatta    360

gaagaaaagt acccaccagg attctactgt ggtaagggtg acaacttcga ctacgaagat    420

gttccaattt tagagacctg gaaggctctt gaaaagttgg tcaaggccgg taagatcagg    480

tctatcggtg tttctaactt cccaggtgct ttgctcttgg acttgttgag aggtgctacc    540

atcaagccat ctgtcttgca agttgaacac cacccatact tgcaacaacc aagattgatc    600

gagttcgctc aatcccgtgg tattgctgtc accgcttact cttcgttcgg tcctcaatct    660

ttcgttgaat tgaaccaagg tagagctttg aacacttctc cattgttcga gaacgaaact    720

atcaaggcta tcgctgctaa gcacggtaag tctccagctc aagtcttgtt gagatggtct    780

tcccaaagag gcattgccat cattccaaag agcaatactg tcccattctt gttggaaaac    840

aaggatgtca acagcttcga cttggacgaa caagatttcg ctgacattgc caagttggac    900

atcaacttga gattcaacga cccatgggac tgggacaaga ttcctatctt cgtctaa       957
```

<210> SEQ ID NO 51
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 51

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Phe Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 52
<211> LENGTH: 1092
<212> TYPE: DNA
<213> ORGANISM: Artificial sequence
<220> FEATURE:
<223> OTHER INFORMATION: Synthetic DNA

<400> SEQUENCE: 52

```
atgaccgcta atccctctct tgttttgaat aagattgacg acatttcttt tgaaacttac      60

gatgctcccg aaattagcga acccacagac gttttagttc aagttaaaaa aactggtatc     120

tgcggttctg acatccactt ctacgctcat ggaaggatcg gcaacttcgt cttaacaaag     180

ccaatggttc tgggtcatga aagcgcgggt actgttgttc aagtcggtaa aggtgttact     240

tcactgaagg ttggtgataa cgtcgcaatc gagcccggta ttccatctag gttcagtgat     300

gagtacaaat ctggtcacta caacctgtgt ccacacatgg catttgctgc tactcccaat     360

tctaaagagg gtgaaccaaa cccaccagga actctatgta agtacttcaa atctccagaa     420

gacttcctgg ttaagttacc cgatcatgtt tctttggagt tgggtgcttt ggtcgagcca     480

ctatctgttg ggtccatgc  tagtaaatta ggctccgttg catttggcga ttacgttgct     540

gtttttggtg ctggtccagt aggattactg gctgccgctg tcgctaagac atttggtgcc     600

aagggtgtga ttgtcgttga tatatctgac aagaagctga agatggccaa agacataggt     660

gccgctacac ataccttcaa ctccaagacg ggaggtagtg aagaattgat caaagccttc     720

ggtggtaatg taccaaatgt tgtcttggaa tgtactgggg ctgaaccatg tattaagcta     780

ggtgttgatg ccatcgcacc aggtggtaga ttcgtgcaag ttggtaatgc tgctggtccc     840

gtgtcctttc ccataacagt gttcgctatg aaagaactta ctttgtttgg ttcatttcgt     900

tatggtttca acgactataa gacagccgtg ggtatctttg atactaacta ccagaacggt     960

agagagaatg ctcccattga ctttgaacag cttatcacgc acagatacaa attcaaagac    1020

gccattgaag cctacgacct agtaagagca ggtaaagggg ctgtcaagtg tttgattgat    1080

ggtccagaat aa                                                        1092
```

```
<210> SEQ ID NO 53
<211> LENGTH: 363
<212> TYPE: PRT
<213> ORGANISM: Artificial sequence
<220> FEATURE:
<223> OTHER INFORMATION: Synthetic polypeptide

<400> SEQUENCE: 53

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160
```

```
Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Ser Asp Lys Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360
```

<210> SEQ ID NO 54
<211> LENGTH: 957
<212> TYPE: DNA
<213> ORGANISM: Artificial sequence
<220> FEATURE:
<223> OTHER INFORMATION: Synthetic DNA

<400> SEQUENCE: 54

```
atgacctcta ttaagttgaa ctctggttac gacatgccag ccgtcggttt cggctgttgg     60

aaagttgacg ttgacacctg ttctgaacag gtctaccgtg ctatcaagac cggttacaga    120

ttgttcgacg gtgccgaaga ttacggcaac gaaaagttag ttggtgccgg tgtcaagaag    180

gccattgacg aaggtatcgt caagcgtgaa gacttgttcc ttacctccaa gttgtggaac    240

aactaccacc acccagacaa cgtcgaaaag gccttgaaca gaaccctttc tgacttgcaa    300

gttgactacg ttgacttgtt cttgatccac ttcccagtca ccttcaagtt cgttccatta    360

gaagaaaagt acccaccagg attctactgt ggtaagggtg acaacttcga ctacgaagat    420

gttccaattt tagagacctg gaaggctctt gaaaagttgg tcaaggccgg taagatcagg    480

tctatcggtg tttctaactt cccaggtgct ttgctcttgg acttgttgag aggtgctacc    540

atcaagccat ctgtcttgca agttgaacac cacccatact tgcaacaacc aagattgatc    600

gagttcgctc aatcccgtgg tattgctgtc accgcttact cttcgttcgg tcctcaatct    660

ttcgttgaat tgaaccaagg tagagctttg aacacttctc cattgttcga gaacgaaact    720

atcaaggcta tcgctgctaa gcacggtaag tctccagctc aagtcttgtt gagatggtct    780

tcccaaagag gcattgccat cattccaaag tccaacactg tcccatggtt gttggaaaac    840

aaggatgtca acagcttcga cttggacgaa caagatttcg ctgacattgc caagttggac    900
```

atcaacttga gattcaacga cccatgggac tgggacaaga ttcctatctt cgtctaa 957

<210> SEQ ID NO 55
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 55

```
Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 56
<211> LENGTH: 957
<212> TYPE: DNA
<213> ORGANISM: Artificial sequence
<220> FEATURE:
<223> OTHER INFORMATION: Synthetic DNA

<400> SEQUENCE: 56
atgacctcta ttaagttgaa ctctggttac gacatgccag ccgtcggttt cggctgttgg 60
aaagttgacg ttgacacctg ttctgaacag gtctaccgag ctatcaagac cggttacaga 120
ttgttcgacg gtgccgaaga ttacggcaac gaaaaattag ttggtgccgg tgtcaagaag 180
gccattgacg aaggtatcgt caagcgtgaa gacttgttcc ttacctccaa gttgtggaac 240
aactaccacc acccagacaa cgtcgaaaag gccttgaaca gaacccttc tgacttgcaa 300 gttgactacg ttgacttgtt cttgatccac ttcccagtca ccttcaagtt cgttccatta 360
gaagaaaagt acccaccagg attctactgt ggtaacggtg acaacttcga ctacgaagat 420
gttccaattt tagagacctg gaaggctctt gaaaagttgg tcaaggccgg taagatcagg 480
tctatcggtg tttctaactt cccaggtgct ttgctcttgg acttgttgag aggtgctacc 540
atcaagccat ctgtcttgca agttgaacac cacccatact tgcaacaacc aagattgatc 600
gagttcgctc aatcccgtgg tattgctgtc accgcttact cttcgttcgg tcctcaatct 660
ttcgttgaat tgaaccaagg tagagctttg aacactaagc cattgttcga gaacgaaact 720
atcaaggcta tcgctgctaa gcacggcaag agcccagctc aagtcttgtt gagatggtct 780
tcccaaagag gcattgccgt tattccaaag tccaacactg tcccatggtt gttggaaaac 840
aaggatgtca acagcttcga cttggacgaa caagatttcg ctgacattgc caagttggac 900
atcaacttga gattcaacga cccatgggac tgggacaaga ttcctatctt cgtctaa 957

<210> SEQ ID NO 57
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 57

Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Asn Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro

```
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Lys Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Val Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 58
<211> LENGTH: 957
<212> TYPE: DNA
<213> ORGANISM: Artificial sequence
<220> FEATURE:
<223> OTHER INFORMATION: Synthetic DNA

<400> SEQUENCE: 58

```
atgacctcta ttaagttgaa ctctggttac gacatgccag ccgtcggttt cggctgttgg      60

aaagttgacg ttgacacctg ttctgaacag gtctaccgag ctatcaagac cggttacaga     120

ttgttcgacg gtgccgaaga ttacggcaac gaaaaattag ttggtgccgg tgtcaagaag     180

gccattgacg aaggtatcgt caagcgtgaa gacttgttcc ttacctccaa gttgtggaac     240

aactaccacc acccagacaa cgtcgaaaag gccttgaaca gaacccttc tgacttgcaa     300

gttgactacg ttgacttgtt cttgatccac ttcccagtca ccttcaagtt cgttccatta     360

gaagaaaagt acccaccagg attctactgt ggtaacggtg acaacttcga ctacgaagat     420

gttccaattt tagagacctg gaaggctctt gaaaagttgg tcaaggccgg taagatcagg     480

tctatcggtg tttctaactt cccaggtgct ttgctcttgg acttgttgag aggtgctacc     540

atcaagccat ctgtcttgca agttgaacac cacccatact tgcaacaacc aagattgatc     600

gagttcgctc aatcccgtgg tattgctgtc accgcttact cttcgttcgg tcctcaatct     660

ttcgttgaat tgaaccaagg tagagctttg aacactaagc cattgttcga gaacgaaact     720

atcaaggcta tcgctgctaa gcacggcaag agcccagctc aagtcttgtt gagatggtct     780

tcccaaagag gcattgccgt tattccaaag tccaacactg tcccatggtt gttggaaaac     840

aaggatgtca acagcttcga cttggacgaa caagatttcg ctgacattgc caagttggac     900

atcaacttga gattcaacga cccatgggac tgggacaaga ttcctatctt cgtctaa        957
```

<210> SEQ ID NO 59
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 59

```
Met Thr Ser Ile Lys Leu Asn Ser Gly Tyr Asp Met Pro Ala Val Gly
```

-continued

```
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Asn Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Lys Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Val Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```